United States Patent
Kiani et al.

(10) Patent No.: US 10,939,878 B2
(45) Date of Patent: Mar. 9, 2021

(54) OPIOID OVERDOSE MONITORING

(71) Applicant: Masimo Corporation, Irvine, CA (US)

(72) Inventors: Massi Joe E. Kiani, Laguna Niguel, CA (US); Bilal Muhsin, San Clemente, CA (US); Ammar Al-Ali, San Juan Capistrano, CA (US); Keith Ward Indorf, Riverside, CA (US); Omar Ahmed, Mission Viejo, CA (US); Jerome Novak, Lake Forest, CA (US); Walter M. Weber, Laguna Hills, CA (US)

(73) Assignee: Masimo Corporation, Irvine, CA (US)

(*) Notice: Subject to any disclaimer, the term of this patent is extended or adjusted under 35 U.S.C. 154(b) by 0 days.

(21) Appl. No.: 16/432,703

(22) Filed: Jun. 5, 2019

(65) Prior Publication Data

US 2019/0374139 A1    Dec. 12, 2019

Related U.S. Application Data

(60) Provisional application No. 62/681,309, filed on Jun. 6, 2018, provisional application No. 62/716,469, filed
(Continued)

(51) Int. Cl.
*A61B 5/00* (2006.01)
*G16H 40/67* (2018.01)
(Continued)

(52) U.S. Cl.
CPC ............ *A61B 5/746* (2013.01); *A61B 5/0064* (2013.01); *A61B 5/02416* (2013.01);
(Continued)

(58) Field of Classification Search
CPC ..... A61B 5/746; A61B 5/4551; A61B 5/6816; A61B 5/6826; A61B 5/0064;
(Continued)

(56) References Cited

U.S. PATENT DOCUMENTS 4,960,128 A    10/1990    Gordon et al.
4,964,408 A    10/1990    Hink et al.
(Continued)

FOREIGN PATENT DOCUMENTS

WO    WO 2018/110510 A1    6/2018
WO    WO 2018/020911 A1    7/2018
WO    WO 2019/236759    12/2019

OTHER PUBLICATIONS

Partial International Search Report, dated Sep. 10, 2019, for PCT Application No. PCT/US2019/035664, 11 pages.
(Continued)

*Primary Examiner* — Hirdepal Singh
(74) *Attorney, Agent, or Firm* — Knobbe, Martens, Olson & Bear, LLP

(57) ABSTRACT

An overdose of opioids can cause the user to stop breathing, resulting in death. A physiological monitoring system monitors respiration based on oxygen saturation readings from a fingertip pulse oximeter in communication with a smart mobile device and sends opioid monitoring information from the smart mobile device to an opioid overdose monitoring service. The opioid overdose monitoring service notifies a first set of contacts when the opioid monitoring information.

20 Claims, 56 Drawing Sheets

Related U.S. Application Data on Aug. 9, 2018, provisional application No. 62/733,314, filed on Sep. 19, 2018, provisional application No. 62/745,031, filed on Oct. 12, 2018, provisional application No. 62/792,998, filed on Jan. 16, 2019, provisional application No. 62/810,156, filed on Feb. 25, 2019, provisional application No. 62/836,855, filed on Apr. 22, 2019, provisional application No. 62/745,243, filed on Oct. 12, 2018.

(51) Int. Cl.

| | | |
|---|---|---|
| *A61B 5/024* | (2006.01) | |
| *A61B 5/08* | (2006.01) | |
| *A61B 7/00* | (2006.01) | |
| *G08B 21/04* | (2006.01) | |
| *A61M 5/142* | (2006.01) | |
| *A61M 5/172* | (2006.01) | |
| *A61B 5/1455* | (2006.01) | |
| *A61K 31/485* | (2006.01) | |
| *G06T 7/00* | (2017.01) | |

(52) U.S. Cl.
CPC ........ *A61B 5/0806* (2013.01); *A61B 5/14551* (2013.01); *A61B 5/4839* (2013.01); *A61B 5/6816* (2013.01); *A61B 5/6826* (2013.01); *A61B 5/7405* (2013.01); *A61B 5/747* (2013.01); *A61B 5/748* (2013.01); *A61B 7/003* (2013.01); *A61M 5/14248* (2013.01); *A61M 5/1723* (2013.01); *G08B 21/0415* (2013.01); *G08B 21/0469* (2013.01); *G08B 21/0476* (2013.01); *G08B 21/0492* (2013.01); *G16H 40/67* (2018.01); *A61B 5/6823* (2013.01); *A61B 5/6829* (2013.01); *A61B 5/6898* (2013.01); *A61B 5/7203* (2013.01); *A61K 31/485* (2013.01); *A61M 2205/18* (2013.01); *A61M 2205/3553* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/8206* (2013.01); *A61M 2230/06* (2013.01); *A61M 2230/20* (2013.01); *A61M 2230/42* (2013.01); *G06T 7/0012* (2013.01); *G06T 2207/30076* (2013.01)

(58) Field of Classification Search
CPC . A61B 5/02416; A61B 5/0806; A61B 5/4839; A61B 5/7405; A61B 5/747; A61B 5/748; A61B 7/003; A61B 5/6823; A61B 5/6829; A61B 5/6898; A61B 5/7203; A61B 5/68; A61B 5/14542; A61B 5/024; A61B 5/0205; A61B 5/4848; A61B 5/0022; A61B 5/4845; G08B 21/0415; G08B 21/0469; G08B 21/0476; G08B 21/0492; A61K 31/485; G06T 7/0012; G06T 2207/30076; A61M 2005/14272; A61M 2005/14252; A61M 2005/1726; A61M 5/14276; A61M 5/14248; A61M 5/1723; A61M 2205/18; A61M 2205/3553; A61M 2205/3592; A61M 2205/50; A61M 2205/502; A61M 2205/505; A61M 2205/52; A61M 2205/581; A61M 2205/8206; A61M 2230/06; A61M 2230/20; A61M 2230/42; G16H 10/60; G16H 20/17; G16H 40/67
USPC .................................................. 340/539.12
See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |

(56) References Cited

U.S. PATENT DOCUMENTS

| | | |
|---|---|---|
| 6,152,754 A | 11/2000 | Gerhardt et al. |
| 6,157,850 A | 12/2000 | Diab et al. |
| 6,163,281 A | 12/2000 | Torch |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,611,206 B2 | 8/2003 | Eshelman et al. |
| 6,611,707 B1 | 8/2003 | Prausnitz et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,723,046 B2 | 4/2004 | Lichtenstein |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,767,341 B2 | 7/2004 | Cho |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,936,007 B2 | 8/2005 | Quy |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,976,958 B2 | 12/2005 | Quy |
| 6,979,812 B2 | 12/2005 | Al-Ali |
| 6,985,524 B1 | 1/2006 | Borchers |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,156,809 B2 | 1/2007 | Quy |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,220,000 B2 | 5/2007 | Alster et al. |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |

(56) References Cited

U.S. PATENT DOCUMENTS

| | | |
|---|---|---|
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,733,224 B2 | 6/2010 | Tran |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 7,999,685 B2 | 8/2011 | Sanchez et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,135,227 B2 | 3/2012 | Lewis et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |

(56) References Cited

U.S. PATENT DOCUMENTS

| | | |
|---|---|---|
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani |
| 8,390,694 B2 | 3/2013 | Ryan et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,591,430 B2 | 11/2013 | Amurthur et al. |
| 8,600,467 B2 | 12/2013 | Al-Ali et al. |
| 8,603,384 B2 | 12/2013 | Luttge et al. |
| 8,606,342 B2 | 12/2013 | Diab |
| 8,615,408 B2 | 12/2013 | Ryan |
| 8,622,922 B2 | 1/2014 | Banet et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,968,195 B2 | 3/2015 | Tran |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |

(56) References Cited

U.S. PATENT DOCUMENTS

| | | |
|---|---|---|
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,075 B2 * | 11/2015 | Baker, Jr. ............ A61B 5/02416 |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,283,150 B2 | 3/2016 | Bujalski et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,405,135 B2 | 8/2016 | Sweis et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,706 B2 | 1/2017 | Soomro et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,597,004 B2 | 3/2017 | Hughes et al. |
| 9,615,792 B2 | 4/2017 | Raptis et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,700,222 B2 | 7/2017 | Quinlan et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,820,699 B2 | 11/2017 | Bingley et al. |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,887,650 B2 | 2/2018 | Maekawa et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |

(56) References Cited

U.S. PATENT DOCUMENTS

| | | |
|---|---|---|
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| 10,008,091 B2 | 6/2018 | Mason et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,445 B1 | 8/2018 | Torch |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,623 B2 | 6/2019 | Edwards et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0106858 A1 | 6/2004 | Say et al. |
| 2004/0147824 A1 | 7/2004 | Diab et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0140502 A1 | 6/2006 | Tseng et al. |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0293781 A1 | 12/2007 | Sims et al. |
| 2008/0008745 A1 | 1/2008 | Stinchcomb et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0125060 A1 | 5/2011 | Telfort et al. |

(56) References Cited

U.S. PATENT DOCUMENTS

| | | |
|---|---|---|
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0041279 A1 | 2/2012 | Freeman et al. |
| 2012/0123231 A1 | 5/2012 | O'Reilly |
| 2012/0136232 A1 | 5/2012 | Jeong et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0033485 A1 | 2/2013 | Kollin et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0172759 A1* | 7/2013 | Melker ............... A61B 5/0002 600/476 |
| 2013/0243021 A1 | 9/2013 | Siskavich |
| 2013/0296672 A1 | 11/2013 | O'Neil et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0228657 A1 | 8/2014 | Palley et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0134107 A1 | 5/2015 | Hyde et al. |
| 2015/0141910 A1 | 5/2015 | Francis et al. |
| 2015/0173674 A1 | 6/2015 | Hayes et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank |
| 2015/0367071 A1 | 12/2015 | Donnellan et al. |
| 2016/0019360 A1 | 1/2016 | Pahwa et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0071392 A1 | 3/2016 | Hankey et al. |
| 2016/0081552 A1 | 3/2016 | Wojtczuk et al. |
| 2016/0095543 A1 | 4/2016 | Telfort et al. |
| 2016/0103598 A1 | 4/2016 | Al-Ali et al. |
| 2016/0129182 A1 | 5/2016 | Schuster et al. |
| 2016/0166183 A1 | 6/2016 | Poeze et al. |
| 2016/0166766 A1* | 6/2016 | Schuster ............... G01F 22/00 702/54 |
| 2016/0196388 A1 | 7/2016 | Lamego |
| 2016/0197436 A1 | 7/2016 | Barker et al. |
| 2016/0212404 A1 | 7/2016 | Maiello et al. |
| 2016/0213281 A1 | 7/2016 | Eckerbom et al. |
| 2016/0228043 A1 | 8/2016 | O'Neil et al. |
| 2016/0263317 A1 | 9/2016 | Arefieg |
| 2016/0270735 A1 | 9/2016 | Diab et al. |
| 2016/0283665 A1 | 9/2016 | Sampath et al. |
| 2016/0287786 A1 | 10/2016 | Kiani |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0328993 A1* | 11/2016 | Brogioli ............... A61B 5/0816 |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0084133 A1 | 3/2017 | Cardinali et al. |
| 2017/0086723 A1 | 3/2017 | Al-Ali et al. |
| 2017/0094450 A1 | 3/2017 | Tu et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0172522 A1* | 6/2017 | Insler ............... A61B 5/14551 |
| 2017/0173632 A1 | 6/2017 | Al-Ali |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0246390 A1 | 8/2017 | Tchao et al. |
| 2017/0251974 A1 | 9/2017 | Shreim et al. |
| 2017/0251975 A1 | 9/2017 | Shreim et al. |
| 2017/0293727 A1 | 10/2017 | Klaassen et al. |
| 2017/0311891 A1 | 11/2017 | Kiani et al. |
| 2017/0332952 A1 | 11/2017 | Desborough et al. |
| 2017/0332976 A1 | 11/2017 | Al-Ali et al. |
| 2017/0340293 A1 | 11/2017 | Al-Ali et al. |
| 2017/0358242 A1 | 12/2017 | Thompson et al. |
| 2017/0360310 A1 | 12/2017 | Kiani et al. |
| 2017/0366627 A1* | 12/2017 | Chan ............... H04L 67/12 |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0035101 A1 | 2/2018 | Osterhout |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0098698 A1 | 4/2018 | Marcus et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0110923 A1 | 4/2018 | Kaplan et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |

(56) References Cited

U.S. PATENT DOCUMENTS

| | | |
|---|---|---|
| 2018/0147343 A1 | 5/2018 | Tyson |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174261 A1* | 6/2018 | Brabazon .............. G16H 80/00 |
| 2018/0174679 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Lndorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1* | 7/2019 | Chandran .............. A61B 5/746 |
| 2019/0201623 A1 | 7/2019 | Kiani |
| 2019/0209025 A1 | 7/2019 | Al-Ali |
| 2019/0209084 A1* | 7/2019 | Bryant ................. A61B 5/0464 |
| 2019/0214778 A1 | 7/2019 | Scruggs et al. |
| 2019/0216317 A1 | 7/2019 | Grande |
| 2019/0216319 A1 | 7/2019 | Poeze et al. |
| 2019/0216321 A1 | 7/2019 | Grande |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0054250 A1* | 2/2020 | Joseph ................. A61B 5/4818 |
| 2020/0054278 A1 | 2/2020 | Joseph et al. |
| 2020/0060869 A1 | 2/2020 | Telfort et al. |
| 2020/0101166 A1 | 4/2020 | Jenkins et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0129117 A1* | 4/2020 | Henderson ........... A61B 5/4839 |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |

OTHER PUBLICATIONS

International Search Report and Written Opinion dated Nov. 6, 2019 for Application No. PCT/US2019/035664, in 20 pages.

Announcing the Winner of the 2016 FDA Naloxone App Competition, U.S. Food & Drug Administration, dated 2016, in 2 pages. https://www.fda.gov/news-events/public-health-focus/announcing-winner-2016-fda-naloxone-app-competition.

Blair, Andre, Monitoring for Opioid Overdoses: Hope Band Can Save People's Life, Advocator, dated Dec. 28, 2018 in 2 pages. https://advocator.ca/news/monitoring-for-opioid-overdoses-hopeband-can-save-peoples-life.

Hsu, Jeremy, Wristband That Detects Opioid Overdose Joins U.S. Race for Tech Solutions, IEEE Spectrum's Biomedical Engineering Blog, dated Dec. 26, 2018, in 2 pages.

A "Second Chance" to Prevent Opioid Deaths, Technology Networks, Informatics News, This App Uses Sonar to Detect Opioid Overdoses, University of Washington, Jan. 10, 2019, in 3 pages, https://www.technologynetworks.com/informatics/news/a-second-chance-to-prevent-opioid-deaths-313744.

McKibben, Justin, OD Help App Could Make Getting Naloxone Like Getting an Uber, Palm Partners Drug Rehab Center, 2018, in 7 pages. https://www.palmpartners.com/od-help-app-naloxone-uber/.

Muoio, Dave, "Robert Wood Johnson Foundation Names Winners of $50,000 AI, Opioid Challenges", Mobihealthnews, dated Sep. 19, 2018, in 13 pages. https://www.mobihealthnews.com/content/robert-wood-johnson-foundation-names-winners-50000-ai-opioid-challenges.

(56) References Cited

OTHER PUBLICATIONS

Middlebrook, Hailey, OD Help app wins FDA's competition to help fight heroin overdose, CNN, dated Dec. 19, 2016, in 4 pages. http:www.cnn.com/2016/09/22/health/fda-heroin-app-competition/index.html.

Grace Young. (Nov. 7, 2016). NALNOW—2016 FDA Naloxone App Competition. Retrieved from https://www.youtube.com/watch?v=DKsHBJm9uNc&feature=youtu.be.

Opioid Overdose, SAMHSA—Substance Abuse and Mental Health Services Administration, retrieved Jul. 2, 2019, in 2 pages. http://www.samhsa.gov/medication-assisted-treatment/treatment/opioid-overdose.

PwrdBy. (Nov. 7, 2016). PwrdBy—OD Help. Retrieved from https://www.youtube.com/watch?v=wiiNvSLbUgo.

Singer, "Pill dispenser that's set by timer may stop opioid addiction before it starts" https://www.democratandchronicle.com, May 8, 2018, in 6 pages.

England, Rachel, Wearable sensor can detect imminent opioid overdose, The low-cost device gives wearers the opportunity to administer life-saving drugs. Engadget, https://www.engadget.com/2018/12/28/wearable-sensor-opioid-overdose/?guccounter=1, Dec. 28, 2018, in 3 pages.

* cited by examiner

330

FIRST RESPONDER PROTOCOL

IF A PERSON IS UNRESPONSIVE AND IT IS NOT KNOWN WHETHER OPIOIDS ARE THE CAUSE, IT IS STANDARD PRACTICE TO ADMINISTER NALOXONE JUST IN CASE.

NOTIFY EMS AND KEEP THEM UPDATED.

IF THE PATIENT DOES NOT HAVE A PULSE, IMMEDIATELY BEGIN CPR ALONG WITH NALOXONE ADMINISTRATION.

IF THE PATIENT IS GASPING OR IN NOT BREATHING, INITIATE CPR/RESCUE BREATHING AS NECESSARY IN ADDITION TO NALOXONE ADMINISTRATION.

NALOXONE IS QUICK ACTING (1-3 MINUTES) AND TYPICALLY LASTS 30-90 MINUTES.

THERE ARE THREE WAYS TO ADMINISTER NALOXONE.

1. SPRAYING NALOXONE INTO THE NOSE.

2. GIVING A SHOT WITH A NEEDLE INTO THE MUSCLE.

3. USING AN AUTO-INJECTOR, A PREFILLED READY-TO-USE DOSE THAT IS PRESSED AGAINST A PERSON'S THIGH.

FIG. 3D

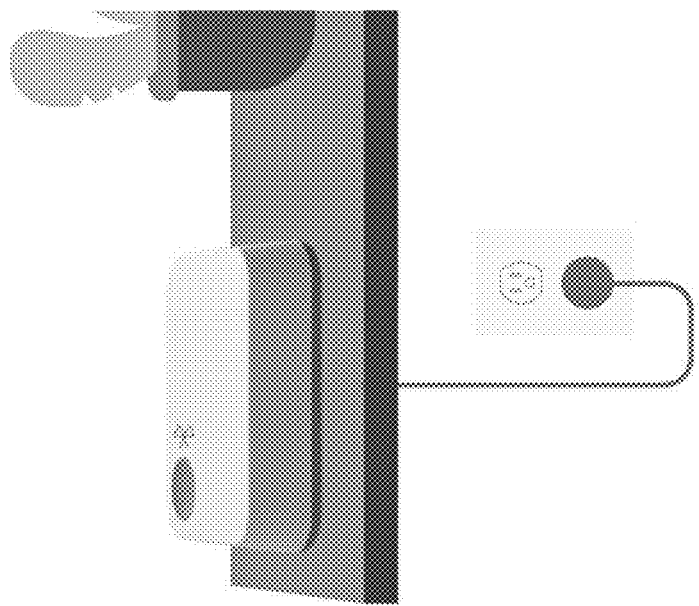
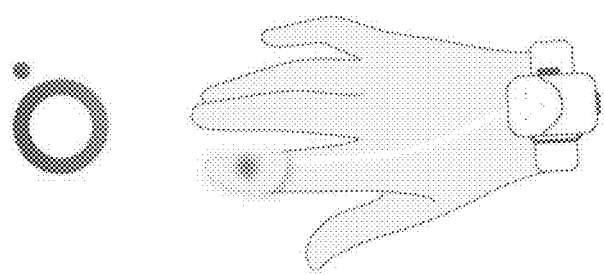
FIG. 18A1
FIG. 18A2

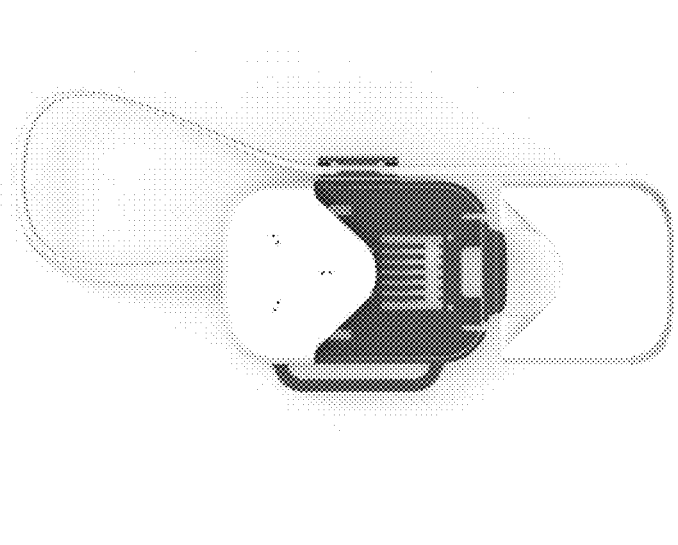
FIG. 18A4
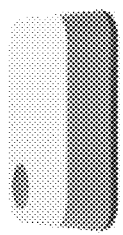
FIG. 18A3

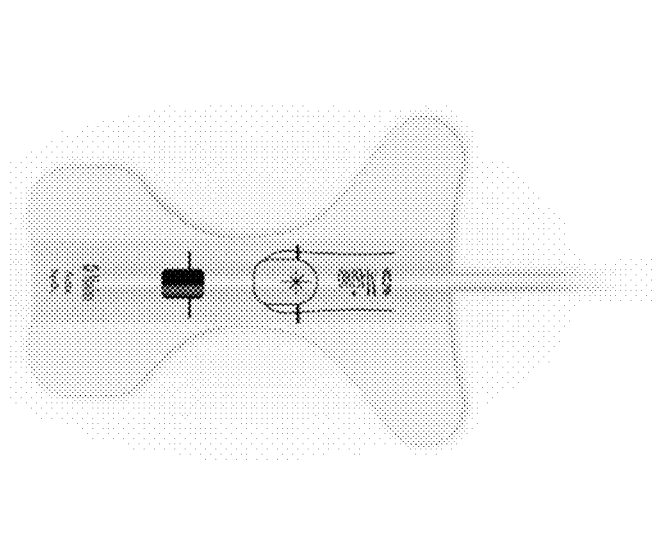
STEP 2
Check the Light
You should now see a green light blinking from your sensor.
FIG. 18A6
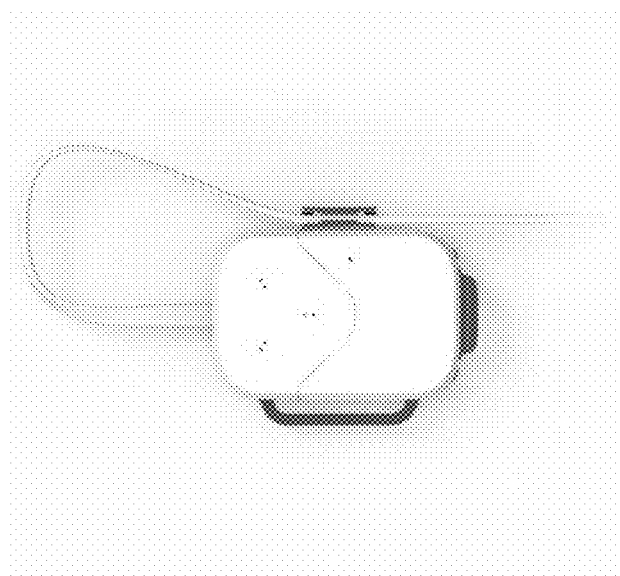
STEP 1
Turn On Sensor
Attach chip to your disposable sensor.
FIG. 18A5

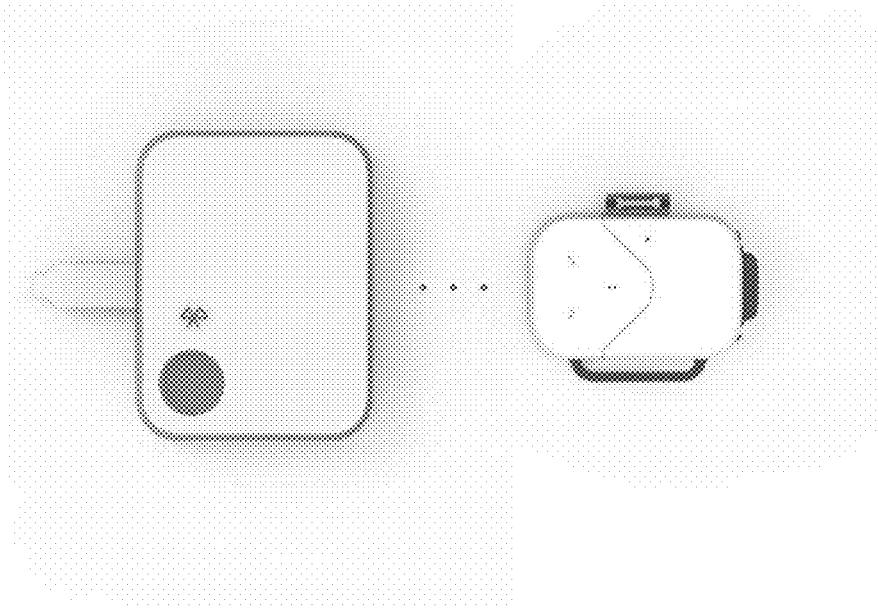
FIG. 18A8
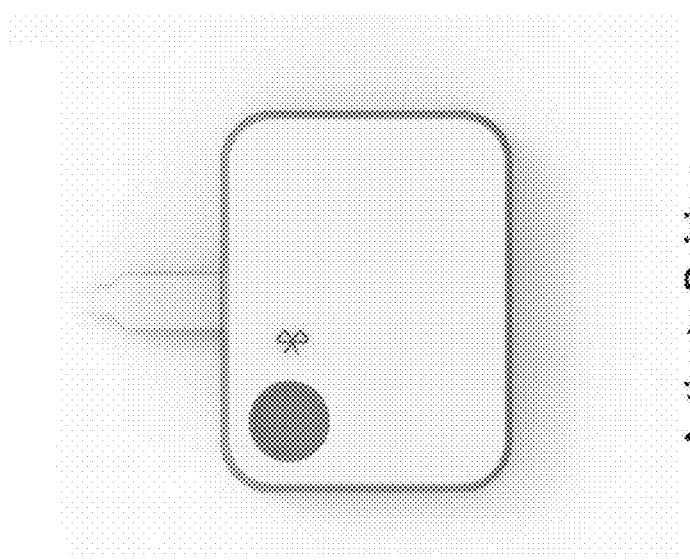
FIG. 18A7

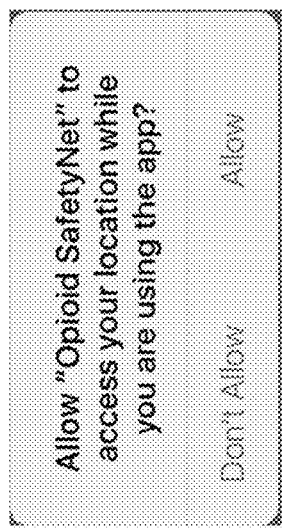
FIG. 18A10
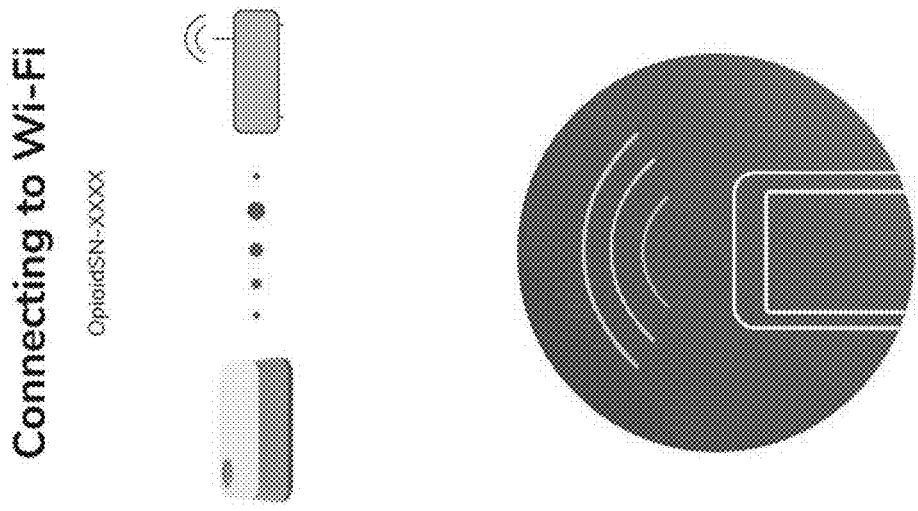
FIG. 18A9

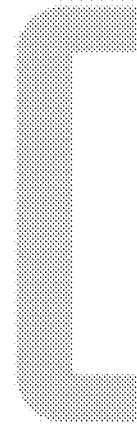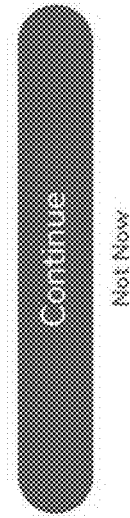
FIG. 18A12
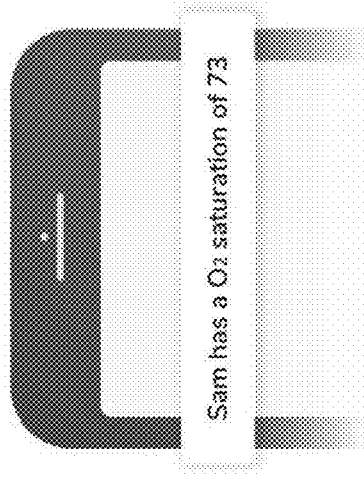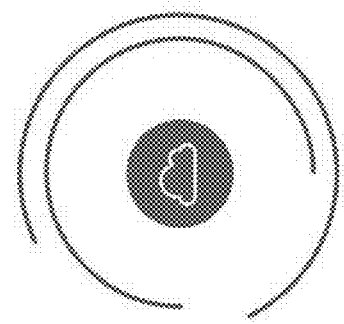
FIG. 18A11

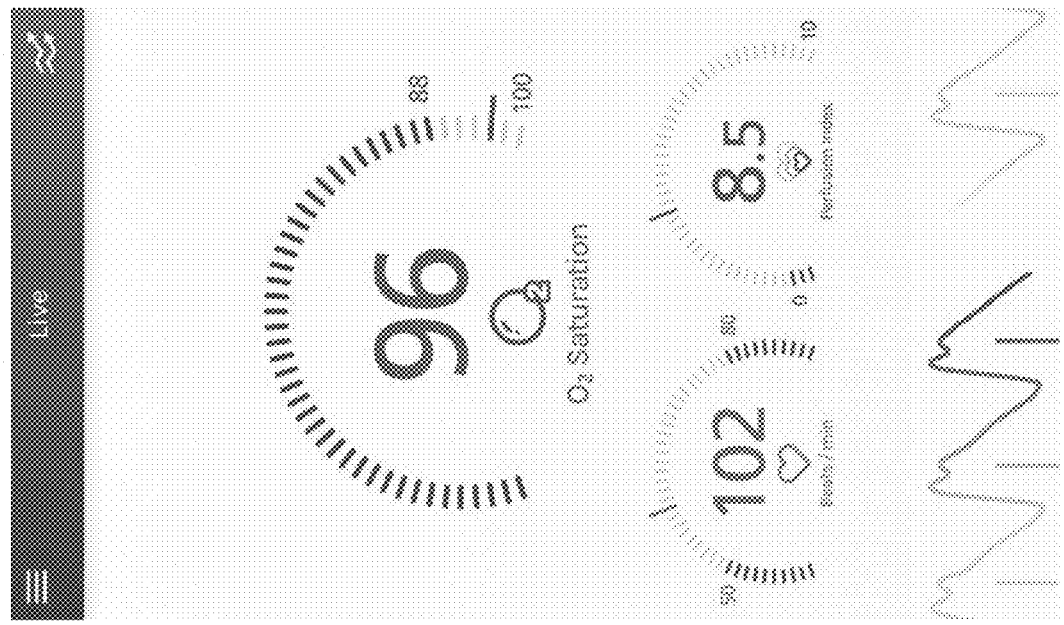
FIG. 18A14
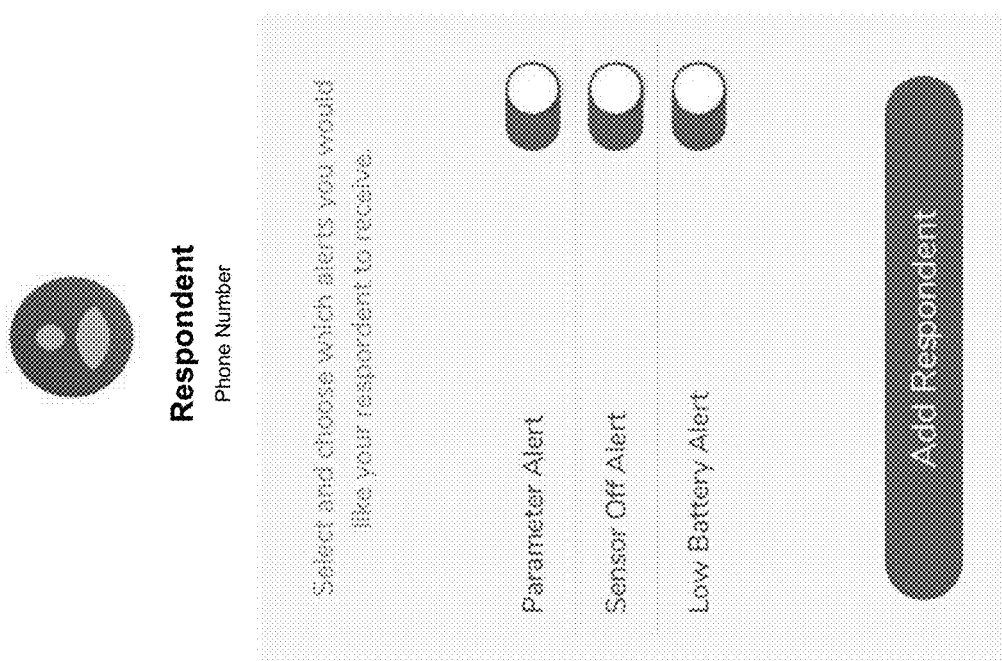
FIG. 18A13

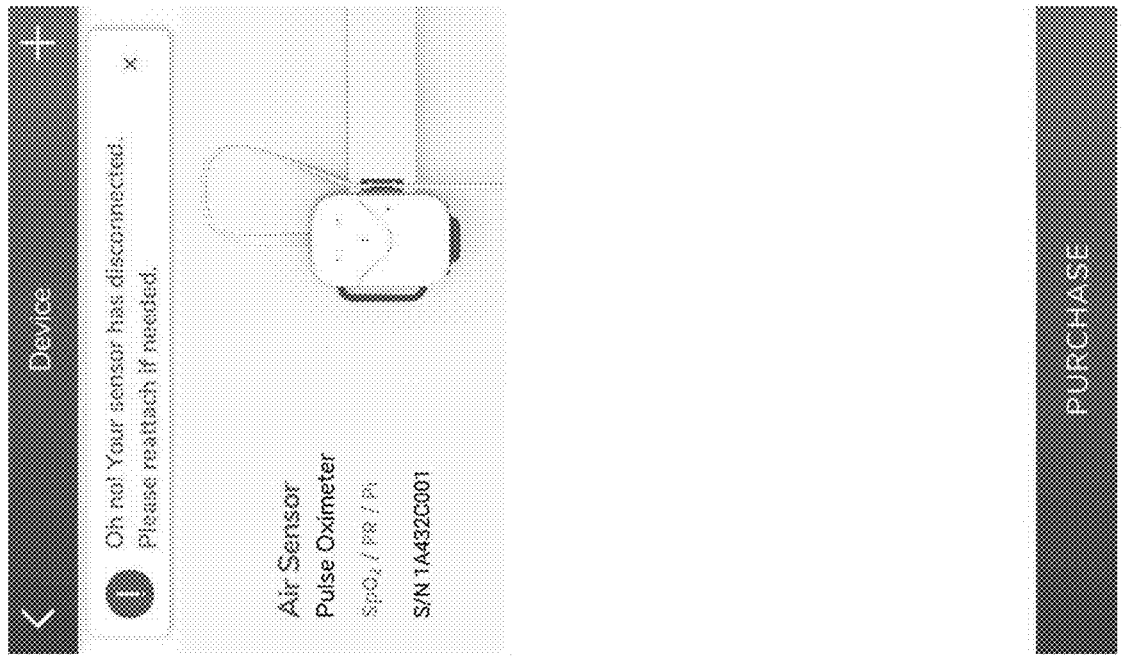
FIG. 18A16
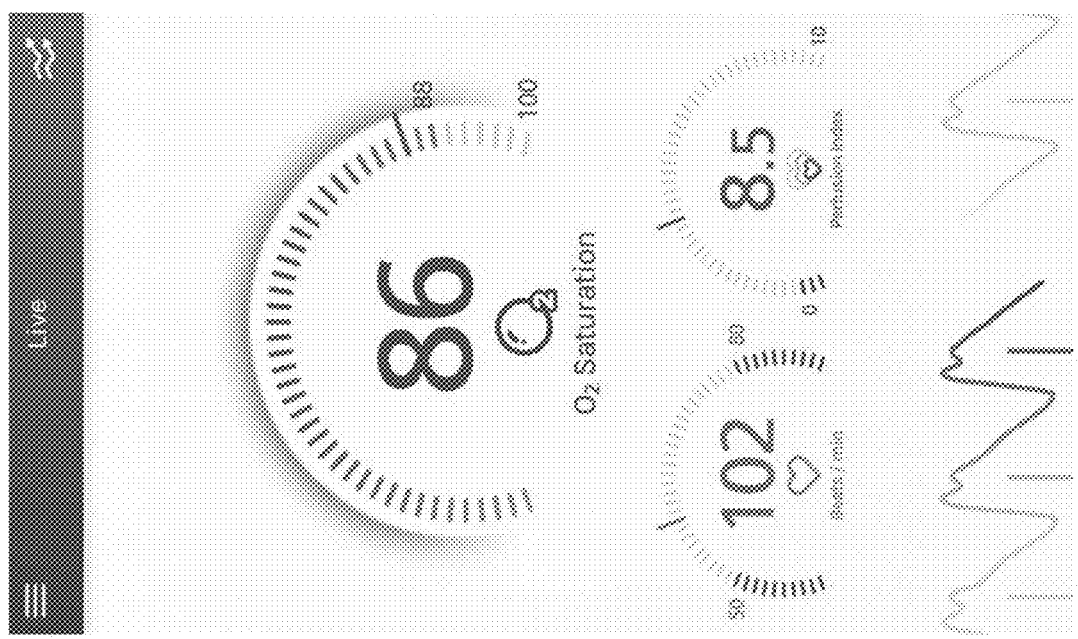
FIG. 18A15

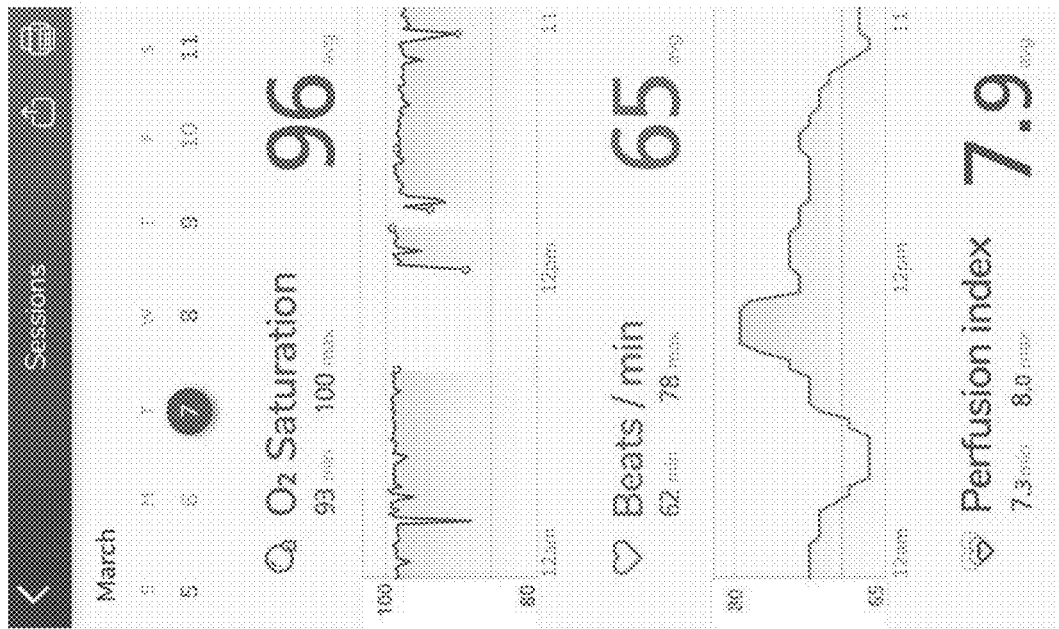
FIG. 18A18
FIG. 18A17

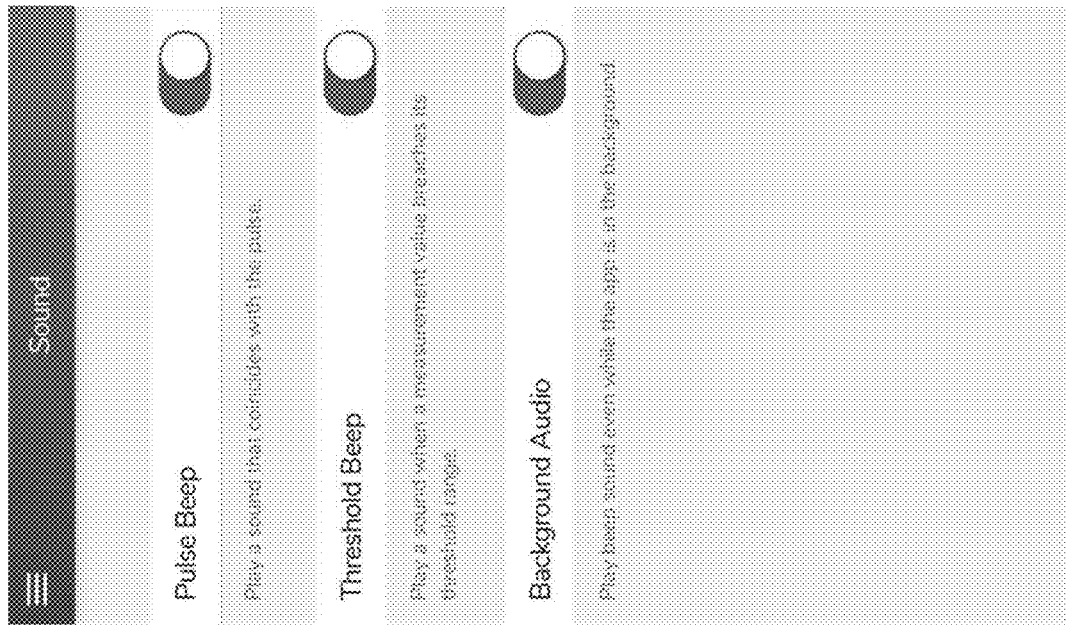
FIG. 18A20
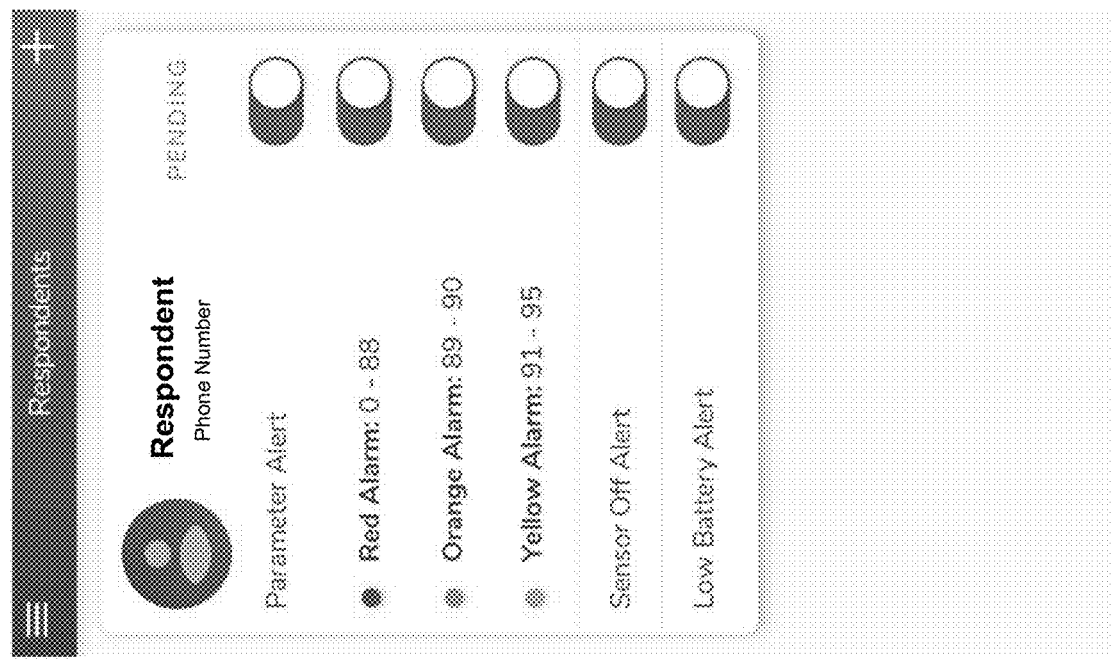
FIG. 18A19

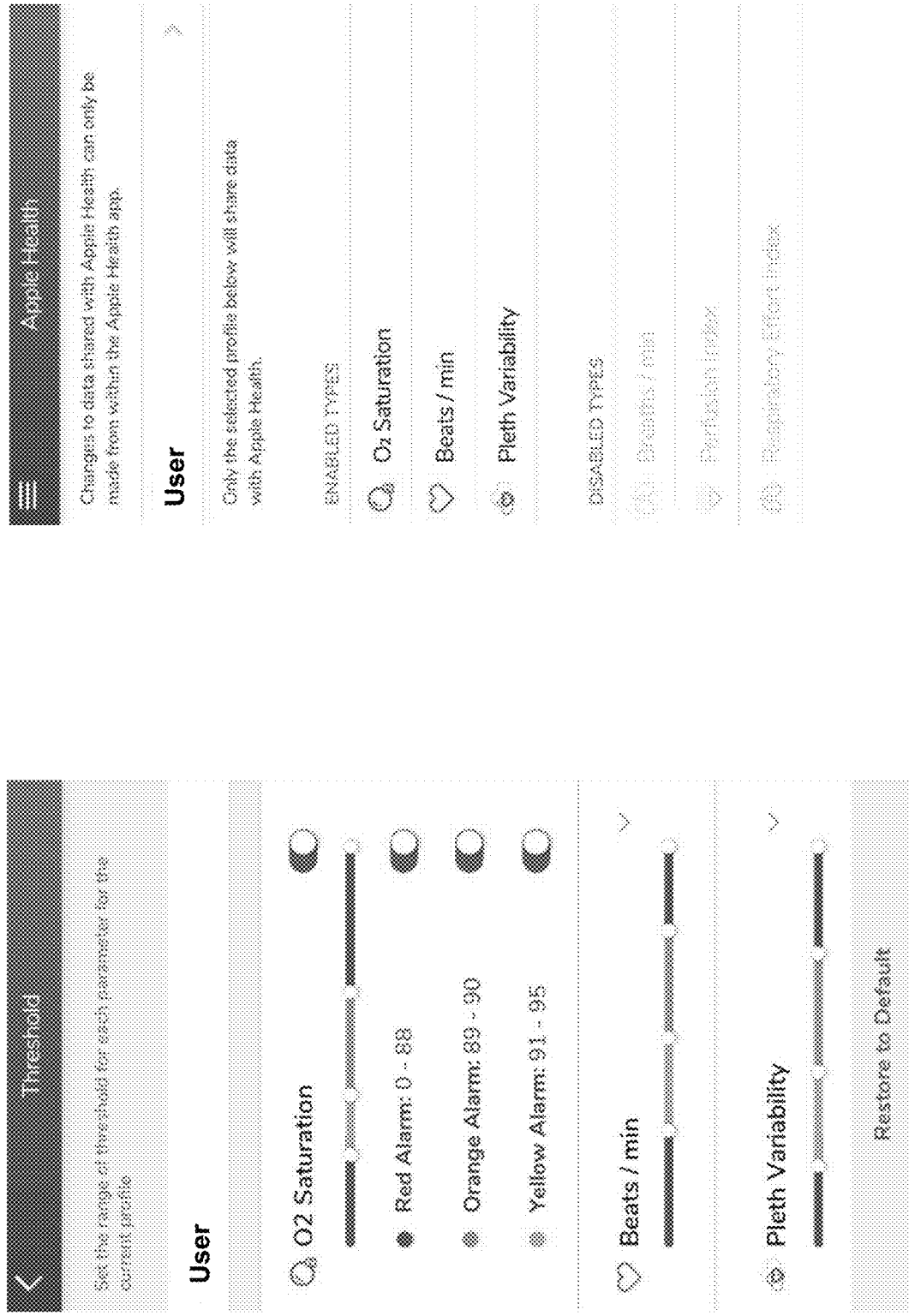
FIG. 18A22
FIG. 18A21

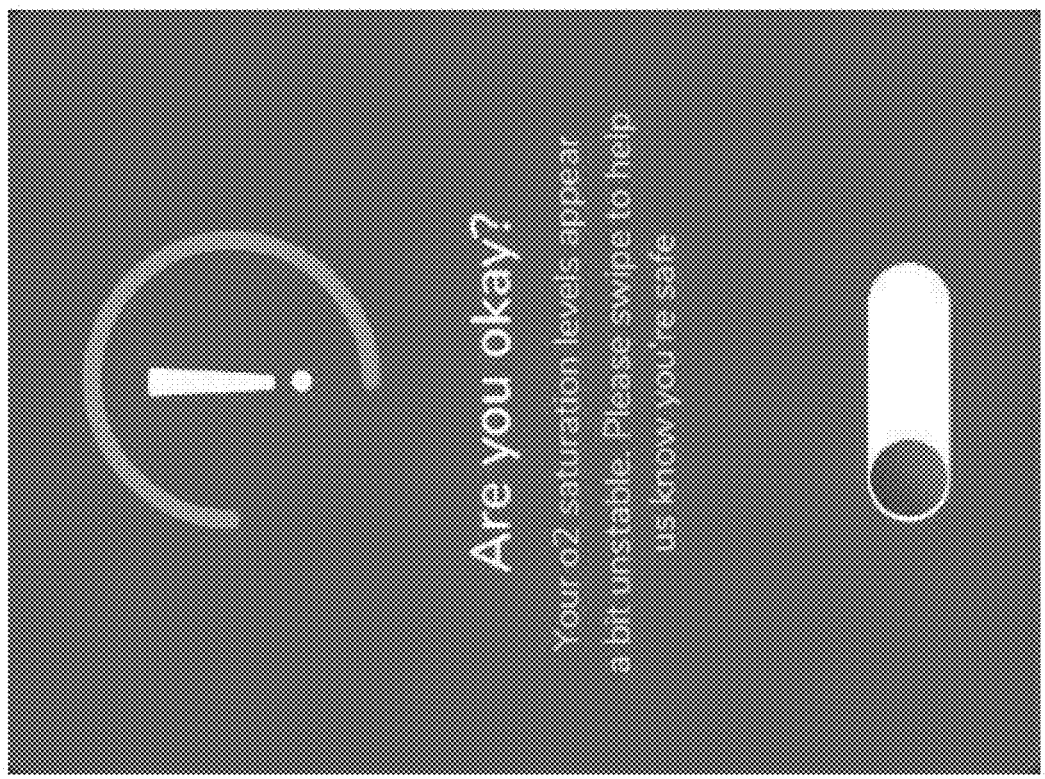
FIG. 18A24
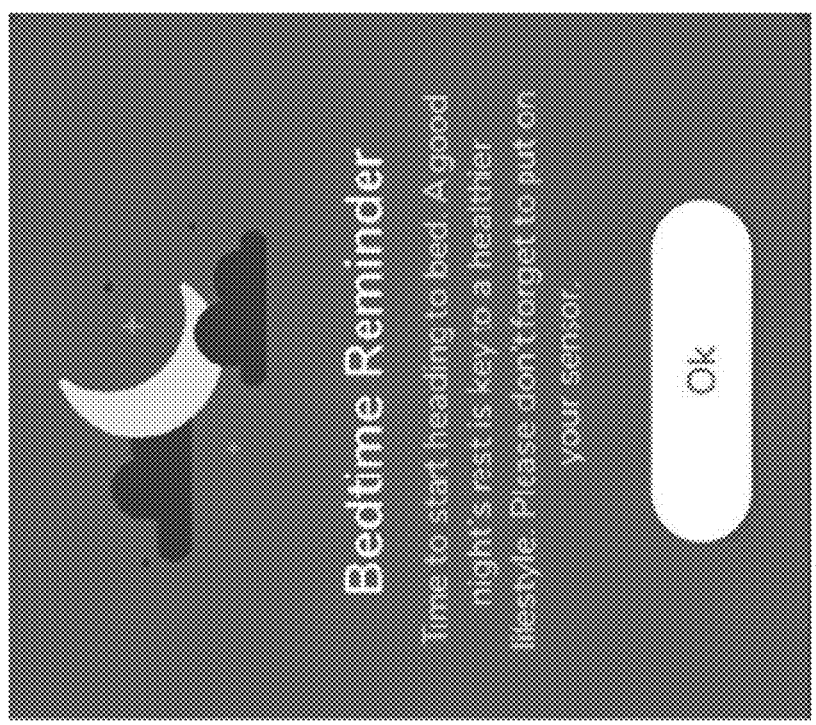
FIG. 18A23

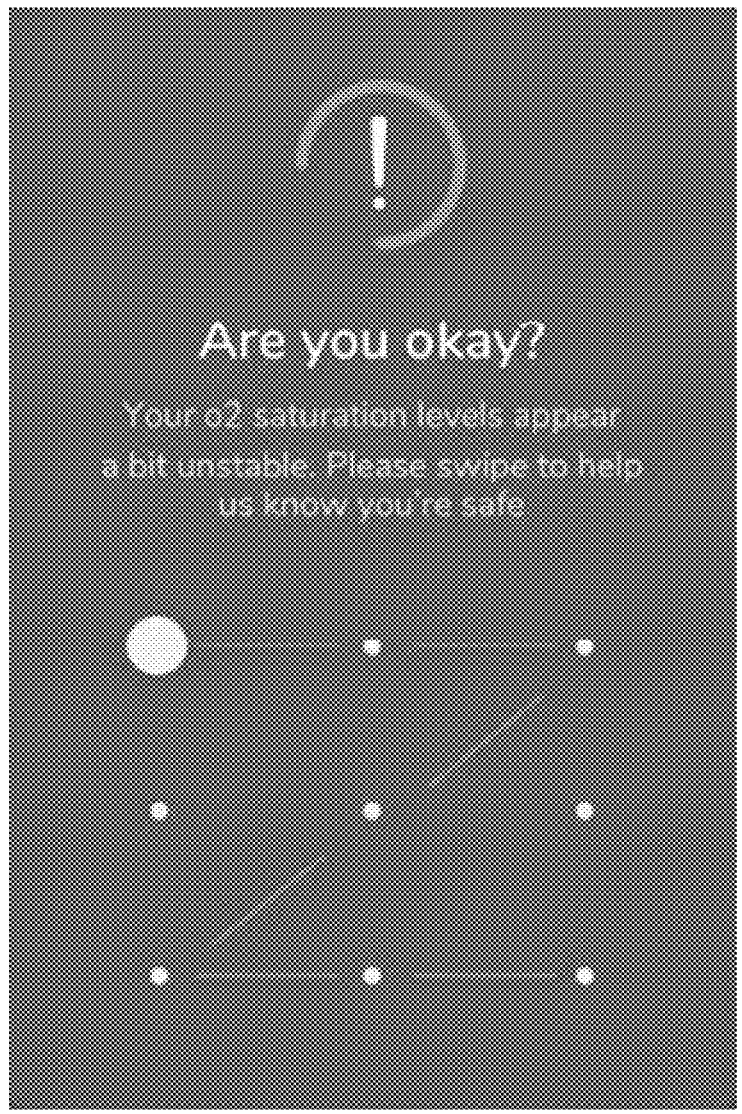
FIG. 18A25

OPIOID OVERDOSE MONITORING

FIELD

The present disclosure relates generally to the field of detecting an opioid overdose, and in particular, to detecting low saturation of oxygen in the blood of an opioid user, and automatically notifying a responder.

BACKGROUND

Substance abuse disorders impact the lives of millions of people. An opioid overdose can occur when a person overdoses on an illicit opioid drug, such as heroin or morphine. Many controlled substances are prescribed by physicians for medical use. Patients can accidentally take an extra dose or deliberately misuse a prescription opioid. Mixing a prescription opioid with other prescription drugs, alcohol, or over-the-counter-medications can cause an overdose. Children are particularly susceptible to accidental overdoses if they take medication that is not intended for them. Opioid overdose is life-threatening and requires immediate emergency attention.

SUMMARY

An opioid overdose is toxicity due to an excess or opioids. Symptoms of an opioid overdose include marked confusion, delirium, or acting drunk; frequent vomiting; pinpoint pupils; extreme sleepiness, or the inability to wake up; intermittent loss of consciousness; breathing problems, including slowed or irregular breathing; respiratory arrest (absence of breathing); respiratory depression (a breathing disorder characterized by slow and ineffective breathing); and cold, clammy skin, or bluish skin around the lips or under the fingernails.

Depressed breathing is the most dangerous side effect of opioid overdose. Lack of oxygen to the brain can not only result in permanent neurologic damage, but may also be accompanied by the widespread failure of other organ systems, including the heart and kidneys. If a person experiencing an opioid overdose is left alone and asleep, the person could easily die as their respiratory depression worsens.

Oximetry can be used to detect depressed breathing. Oximetry utilizes a noninvasive optical sensor to measure physiological parameters of a person. In general, the sensor has light emitting diodes (LEDs) that transmit optical radiation into a tissue site and a detector that responds to the intensity of the optical radiation after absorption (e.g., by transmission or transreflectance) by, for example, pulsatile arterial blood flowing within the tissue site. Based on this response, a processor can determine measurements for peripheral oxygen saturation ($SpO_2$), which is an estimate of the percentage of oxygen bound to hemoglobin in the blood, pulse rate, plethysmograph waveforms, which indicate changes in the volume of arterial blood with each pulse beat, and perfusion quality index (e.g., an index that quantifies pulse strength at the sensor site), among many others.

It is noted that "oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood.

An oximeter that is compatible with a hand held monitor, such as a mobile computing device, can be used to monitor physiological parameters. The oximeter can detect decreased oxygen saturation in the blood of the user. Decreased oxygen saturation in the blood of the user is an indication of respiratory distress, which can be an indication of opioid overdose. Once the oxygen saturation of the user falls below an acceptable threshold, a software application in the mobile computing device can alert others to provide emergency help. The threshold can be set to provide an early indication of an overdose event. If the overdose is caught early, emergency treatment can be provided before irreparable harm occurs.

A system to monitor for indications of opioid overdose and to deliver therapeutic drugs can comprise a sensor wearable by a user configured to obtain data indicative of at least one physiological parameter of the user; a signal processor configured to process the data to provide the at least one physiological parameter; and a drug delivery apparatus wearable by the user and configured to deliver one or more doses of a therapeutic drug. The drug delivery apparatus can comprise a delivery device that includes a dose of a therapeutic drug stored in a reservoir, a drug delivery channel, a dispensing device to dispense the therapeutic drug from the reservoir through the drug delivery channel, and activation circuitry to activate the dispensing device.

The system can further comprise a medical monitoring hub configured to monitor the at least one physiological parameter. The medical monitoring hub can comprise memory storing instructions and one or more computer processors configured to execute the instructions to at least compare the at least one physiological parameter to a threshold that is indicative of opioid overdose; determine that an overdose event is occurring or likely to occur based on the comparison; and send at least one activation signal to the drug delivery apparatus to dispense at least one dose of the therapeutic drug based on the determination.

The one or more computer processors of the medical monitoring hub can be further configured to provide an alarm in response to determining that the overdose event is occurring or likely to occur; wait a period of time after providing the alarm before sending the at least one activation signal; where receiving user input during the period of time stops the sending of the at least one activation signal. The one or more computer processors of the medical monitoring hub can be further configured to receive an indication of medical distress of the user; and send a notification of the medical distress to one or more contacts, wherein the one or more contacts include medical professionals, relatives, friends, and neighbors.

The system can further comprise a housing that houses the sensor, the signal processor, and the drug delivery device. The drug delivery apparatus can further include a first antenna and a first processor in communication with the first antenna, where the sensor can further include a second antenna and a second processor in communication with the second antenna, and where the first and second processors can be configured to provide wireless communication between the drug delivery device and the sensor. The drug delivery apparatus can be a single use drug delivery apparatus. The drug delivery device can further include an antenna to receive an activation signal. The drug delivery apparatus can include at least two drug delivery devices.

The medical monitoring hub can be in communication with a remote server comprising a user database, memory storing instructions, and one or more computing devices configured to execute the instructions to cause the remote server to access user information associated with the user in the user database. The user information can include contact information of contacts to notify with overdose status of the user.

The one or more computing devices of the remote server can be further configured to send notification of the overdose event to at least one contact. The notification can include one or more of a location of the user, a location of an opioid receptor antagonist drug, and an indication of the at least one physiological parameter. The notification can be one or more of a text message, an email, a message on social media, and a phone call.

The system can further comprise a smart device in communication with the signal processor to receive the at least one physiological parameter and in communication with the medical monitoring hub. The smart device can comprise memory storing instructions, and one or more microprocessors configured to execute the instructions to at least compare the at least one physiological parameter to the threshold that is indicative of opioid overdose; determine that the overdose event is occurring or likely to occur based on the comparison; determine that the medical monitoring hub failed to send the at least one activation signal; and send the at least one activation signal to the drug delivery apparatus to dispense at least one dose of the therapeutic drug in response to the determination that that the medical monitoring hub failed to send the at least one activation signal. The memory of the smart device can further store the contact information and the one or more microprocessors of the smart device can be further configured to notify the contacts of the overdose event.

The drug delivery apparatus can comprises a patch and can include an adhesive layer for adhesion to the user. The at least one physiological parameter can comprise one or more of oxygen saturation, heart rate, respiration rate, pleth variability, and perfusion index. The medical monitoring hub can further comprise an input to receive user input, a speaker, and alarm circuitry, and where the one or more computer processors of the medical monitoring hub can be further configured to produce an alarm based on the determination. Volume of the alarm can increase until user input is received. A kit can comprising any of the systems disclosed herein.

A medical monitoring hub to monitor for indications of opioid overdose can comprise memory storing instructions and one or more computer processors configured to execute the instructions to at least receive data indicative of at least one physiological parameter of a user that is obtained by a user-wearable sensor; process the data to provide the at least one physiological parameter; compare the at least one physiological parameter to a threshold that is indicative of opioid overdose; determine that an overdose event is occurring or likely to occur based on the comparison; and send at least one activation signal to a drug delivery apparatus to dispense at least one dose of the therapeutic drug based on the determination. The drug delivery apparatus wearable by the user can be configured to deliver one or more doses of a therapeutic drug.

The drug delivery apparatus can comprises a delivery device that includes a dose of a therapeutic drug stored in a reservoir, a drug delivery channel, a dispensing device to dispense the therapeutic drug from the reservoir through the drug delivery channel, and activation circuitry to activate the dispensing device. The drug delivery apparatus can comprise one or more delivery devices. Each drug delivery device can comprise a dose of a therapeutic drug stored in a reservoir, a drug delivery channel, a dispensing device to dispense the therapeutic drug from the reservoir through the drug delivery channel, activation circuitry to activate the dispensing device, and an antenna to receive the at least one activation signal. Each antenna can be tuned to receive a corresponding activation signal at a different frequency. The one or more computer processors can be further configured to send two or more activation signals. Each of the two or more activation signals can have the different frequencies to cause corresponding two or more activation circuitry to activate to dispense two or more doses of the therapeutic drug at approximately the same time.

A method to monitor for indications of opioid overdose and to deliver therapeutic drugs can comprise obtaining, from a sensor wearable by a user, data indicative of at least one physiological parameter of the user; processing, with a signal processor, the data to provide the at least one physiological parameter; and delivering, from a drug delivery apparatus wearable by the user, one or more doses of a therapeutic drug. The delivering can comprise activating a dispensing device that is configured to dispense through a drug delivery channel a dose of therapeutic drug stored in a reservoir; and dispensing with the activated dispensing device, the dose of the therapeutic drug from the reservoir through the drug delivery channel.

The method can further comprise monitoring, with a medical monitoring hub that can comprise one or more computing devices, the at least one physiological parameter. The monitoring can comprise comparing the at least one physiological parameter to a threshold that is indicative of opioid overdose; determining that an overdose event is occurring or likely to occur based on the comparison; and sending at least one activation signal to the drug delivery apparatus to activate the dispensing device based on the determination. The method can further comprise providing an alarm in response to determining that the overdose event is occurring or likely to occur; and waiting a period of time after providing the alarm before sending the at least one activation signal, where receiving user input during the period of time can stop the sending of the at least one activation signal. The method can further comprise receiving an indication of medical distress of the user; and sending a notification of the medical distress to one or more contacts, wherein the one or more contacts include medical professionals, relatives, friends, and neighbors.

The sensor, the signal processor, and the drug delivery device can be housed in a single housing. The drug delivery apparatus can further include a first antenna and a first processor in communication with the first antenna, where the sensor can further include a second antenna and a second processor in communication with the second antenna. The first and second processors can be configured to provide wireless communication between the drug delivery device and the sensor. The drug delivery apparatus can be a single use drug delivery apparatus. The drug delivery device can further include an antenna to receive an activation signal. The drug delivery apparatus can include at least two drug delivery devices.

The medical monitoring hub can be in communication with a remote server that can comprise a user database, memory storing instructions, and one or more computing devices configured to execute the instructions to cause the remote server to access user information associated with the user in the user database. The user information can include contact information of contacts to notify with overdose status of the user.

The method can further comprise sending, with the remote server, notification of the overdose event to at least one contact. The notification can include one or more of a location of the user, a location of an opioid receptor antagonist drug, and an indication of the at least one physiological parameter. The notification can be one or more of a text message, an email, a message on social media, and a phone call.

A smart device can be in communication with the signal processor to receive the at least one physiological parameter and can be in communication with the medical monitoring hub. The smart device can comprise memory storing instructions, and one or more microprocessors configured to execute the instructions to at least compare the at least one physiological parameter to the threshold that is indicative of opioid overdose; determine that the overdose event is occurring or likely to occur based on the comparison; determine that the medical monitoring hub failed to send the at least one activation signal; and send the at least one activation signal to the drug delivery apparatus to dispense at least one dose of the therapeutic drug in response to the determination that that the medical monitoring hub failed to send the at least one activation signal. The memory of the smart device can further store the contact information and the one or more microprocessors of the smart device are can be further configured to notify the contacts of the overdose event.

The drug delivery apparatus can comprise a patch and can include an adhesive layer for adhesion to the user. The at least one physiological parameter can comprise one or more of oxygen saturation, heart rate, respiration rate, pleth variability, and perfusion index. The medical monitoring hub can further comprise an input to receive user input, a speaker, and alarm circuitry, where the one or more computer processors of the medical monitoring hub can be further configured to produce an alarm based on the determination. The method can further comprises increasing volume of the alarm until user input is received.

A method to monitor for indications of opioid overdose can comprise receiving data indicative of at least one physiological parameter of a user that is obtained by a user-wearable sensor; processing the data to provide the at least one physiological parameter; comparing the at least one physiological parameter to a threshold that is indicative of opioid overdose; determining that an overdose event is occurring or likely to occur based on the comparison; and sending at least one activation signal to a drug delivery apparatus to dispense at least one dose of a therapeutic drug based on the determination. The drug delivery apparatus wearable by the user can be configured to deliver one or more doses of the therapeutic drug.

The drug delivery apparatus can comprise a delivery device that includes a dose of a therapeutic drug stored in a reservoir, a drug delivery channel, a dispensing device to dispense the therapeutic drug from the reservoir through the drug delivery channel, and activation circuitry to activate the dispensing device. The drug delivery apparatus can comprise one or more delivery devices. Each drug delivery device can comprise a dose of a therapeutic drug stored in a reservoir, a drug delivery channel, a dispensing device to dispense the therapeutic drug from the reservoir through the drug delivery channel, activation circuitry to activate the dispensing device, and an antenna to receive the at least one activation signal.

The method can further comprise sending two or more activation signals, where each antenna can be tuned to receive a corresponding activation signal at a different frequency, and where each of the two or more activation signals can have the different frequencies to cause corresponding two or more activation circuitry to activate to dispense two or more doses of the therapeutic drug at approximately the same time.

A system to monitor a user for an opioid overdose event can comprise software instructions storable on a memory of a mobile computing device that includes one or more hardware processors, a touchscreen display, and a microphone. The software instructions can cause the one or more hardware processors to receive sounds from the microphone; determine an opioid overdose event is occurring or will soon occur based on the received sounds; present a request for user input on the touchscreen display based on the determination; and transmit wirelessly notifications of the opioid overdose event to one or more recipients based on a failure to receive user input.

The mobile computing device can further comprise a camera, and the one or more hardware processors can be further configured to receive images from the camera, and determine the opioid overdose event is occurring or will soon occur based on the received sounds and images. The one or more hardware processors can be further configured to receive monitoring data from a monitoring service that monitors the user and an environment local to the user; and transmit the notification of the opioid overdose event to the monitoring service. The monitoring service can be a security alarm service.

The monitoring data can include user data associated with a state of the user and environmental data associated with the environment local to the user. The one or more recipients can include friends and family having contact information stored in the memory of the mobile computing device. The one or more recipients can include one or more of a first responder, an emergency service, a local fire station, an ambulance service, a rehabilitation center, an addiction treatment center, and a rideshare network. The notification can include one or more of a text message, a phone call, and an email. The notification can include directions to a location of the mobile computing device.

The one or more hardware processors can further analyze representations of the sounds from the microphone to determine respiratory distress of the user local to the mobile computing device. The one or more hardware processors can further analyze representations of the images from the camera to determine respiratory distress of the user in the images. The one or more hardware processors can further analyze representations of the images from the camera to determine an unconscious state of the user in the images. The one or more processors further can cause the touchscreen display to display care instructions to care for a victim of an opioid overdose.

The mobile computing device can further comprise a speaker and the one or more hardware processors further can cause the speaker to output an audible alarm based on the determination. The one or more hardware processors can further cause the touchscreen display to flash, cause the touchscreen display to display directions to a location of the mobile computing device, or cause a speaker of the mobile computing to provide audible directions to the location of the user.

A system to monitor a user for an opioid overdose event can comprise software instructions storable on a memory of a mobile computing device that includes one or more hardware processors, a touchscreen display, and a camera, the software instructions causing the one or more hardware processors to receive images from the camera; determine an opioid overdose event is occurring or will soon occur based on the received images; present a request for user input on the touchscreen display based on the determination; and transmit wirelessly notifications of the overdose event to one or more recipients based on a failure to receive user input.

The one or more hardware processors can be further configured to receive monitoring data from a monitoring service that monitors the user and an environment local to the user; and transmit the notification of the opioid overdose event to the monitoring service. The monitoring service can be a security alarm service. The monitoring data can include user data associated with a state of the user and environmental data associated with the environment local to the user. The one or more recipients can include friends and family having contact information stored in the memory of the mobile computing device. The one or more recipients can include one or more of a first responder, an emergency service, a local fire station, an ambulance service, a rehabilitation center, an addiction treatment center, and a rideshare network. The notification can include one or more of a text message, a phone call, and an email. The notification can include directions to a location of the mobile computing device.

The one or more hardware processors can further analyze representations the sounds from the microphone to determine respiratory distress of the user local to the mobile computing device. The one or more hardware processors can further analyze representations of the images from the camera to determine respiratory distress of the user in the images. The one or more hardware processors can further analyze representations of the images from the camera to determine an unconscious state of the user in the images. The one or more processors further can cause the touchscreen display to display care instructions to care for a victim of an opioid overdose. The mobile computing device can further comprise a speaker and the one or more hardware processors further can cause the speaker to output an audible alarm based on the determination. The one or more hardware processors can further cause the touchscreen display to flash, cause the touchscreen display to display directions to a location of the mobile computing device, or cause a speaker of the mobile computing to provide audible directions to the location of the user.

A system to monitor a user for an opioid overdose event can comprise one or more sensors configured to sense indications of an overdose condition of a user from an environment local to the user; and a mobile computing device comprising a touchscreen display, memory storing software instructions, and one or more hardware processors configured to execute the software instructions to at least receive the sensed indications from the one or more sensors; determine an opioid overdose event is occurring or will soon occur based on the received indications; present a request for user input on the touchscreen display based on the determination; and transmit wirelessly notifications of the overdose event to one or more recipients based on a failure to receive user input.

The one or more hardware processors can be further configured to receive monitoring data from a monitoring service that monitors the user and an environment local to the user; and transmit the notification of the opioid overdose event to the monitoring service. The monitoring service is a security alarm service. The monitoring data can include user data associated with a state of the user and environmental data associated with the environment local to the user. The one or more recipients can include friends and family having contact information stored in the memory of the mobile computing device. The one or more recipients can include one or more of a first responder, an emergency service, a local fire station, an ambulance service, a rehabilitation center, an addiction treatment center, and a rideshare network. The notification can include one or more of a text message, a phone call, and an email. The notification can include directions to a location of the mobile computing device.

The one or more hardware processors can further analyze representations of the sounds from the microphone to determine respiratory distress of the user local to the mobile computing device. The one or more hardware processors can further analyze representations of the images from the camera to determine respiratory distress of the user in the images. The one or more hardware processors can further analyze representations of the images from the camera to determine an unconscious state of the user in the images. The one or more processors further can cause the touchscreen display to display care instructions to care for a victim of an opioid overdose. The mobile computing device can further comprise a speaker and the one or more hardware processors further can cause the speaker to output an audible alarm based on the determination. The one or more hardware processors can further cause the touchscreen display to flash, cause the touchscreen display to display directions to a location of the mobile computing device, or cause a speaker of the mobile computing to provide audible directions to the location of the user.

A method to monitor a user for an opioid overdose event can comprise receiving sounds from a microphone of a mobile computing device; determining, with one or more hardware processors of the mobile computing device, an opioid overdose event is occurring or will soon occur based on the received sounds; presenting, with one or more hardware processors, a request for user input on a touchscreen display of the mobile computing device, the request based on the determination; and transmitting wirelessly, with the mobile computing device, notifications of the overdose event to one or more recipients based on a failure to receive user input.

The method can further comprise receiving images from a camera of the mobile computing device; and determining, with the one or more hardware processors of the mobile computing device, the opioid overdose event is occurring or will soon occur based on the received sounds and images. The method can further comprise receive monitoring data from a monitoring service that monitors the user and an environment local to the user; and transmit the notification of the opioid overdose event to the monitoring service. The monitoring service is a security alarm service. The monitoring data can include user data associated with a state of the user and environmental data associated with the environment local to the user. The one or more recipients can include friends and family having contact information stored in the memory of the mobile computing device. The one or more recipients can include one or more of a first responder, an emergency service, a local fire station, an ambulance service, a rehabilitation center, an addiction treatment center, and a rideshare network. The notification can include one or more of a text message, a phone call, and an email. The notification can include directions to a location of the mobile computing device.

The method can further comprise analyzing representations of the sounds from the microphone to determine respiratory distress of the user local to the mobile computing device. The method can further comprise analyzing representations of the images from the camera to determine respiratory distress of the user in the images. The method can further comprise analyzing representations of the images from the camera to determine an unconscious state of the user in the images. The method can further comprise causing the touchscreen display to display care instructions to care for a victim of an opioid overdose. The method can further comprise outputting, from the mobile computing device, an audible alarm based on the determination.

The method can further comprise causing the touchscreen display to flash, cause the touchscreen display to display directions to a location of the mobile computing device, or cause a speaker of the mobile computing to provide audible directions to the location of the user.

A method to monitor a user for an opioid overdose event can further comprise receiving images from a camera of a mobile computing device; determining, with one or more hardware processors of the mobile computing device, an opioid overdose event is occurring or will soon occur based on the received images; presenting, with one or more hardware processors, a request for user input on a touchscreen display of the mobile computing device, the request based on the determination; and transmitting wirelessly, with the mobile computing device, notifications of the overdose event to one or more recipients based on a failure to receive user input.

The method can further comprise receiving monitoring data from a monitoring service that monitors the user and an environment local to the user; and transmitting the notification of the opioid overdose event to the monitoring service. The monitoring service can be a security alarm service. The monitoring data can include user data associated with a state of the user and environmental data associated with the environment local to the user. The one or more recipients can include friends and family having contact information stored in the memory of the mobile computing device. The one or more recipients can include one or more of a first responder, an emergency service, a local fire station, an ambulance service, a rehabilitation center, an addiction treatment center, and a rideshare network. The notification can include one or more of a text message, a phone call, and an email. The notification can include directions to a location of the mobile computing device. The method can further comprise analyzing representations the sounds from the microphone to determine respiratory distress of the user local to the mobile computing device.

A method to monitor a user for an opioid overdose event can comprise receiving sensed indications of an overdose condition of a user from one or more sensors configured to sense an environment local to the user; determine an opioid overdose event is occurring or will soon occur based on the received indications; present a request for user input on the touchscreen display based on the determination; and transmit wirelessly notifications of the overdose event to one or more recipients based on a failure to receive user input.

The method can further comprise receiving monitoring data from a monitoring service that monitors the user and an environment local to the user; and transmitting the notification of the opioid overdose event to the monitoring service. The monitoring service can be a security alarm service. The monitoring data can include user data associated with a state of the user and environmental data associated with the environment local to the user. The method can further comprise analyzing representations of the images from the camera to determine respiratory distress of the user in the images.

The method can further comprise analyzing representations of the images from the camera to determine an unconscious state of the user in the images. The method can further comprise causing the touchscreen display to display care instructions to care for a victim of an opioid overdose. The method can further comprise outputting, from the mobile computing device, an audible alarm based on the determination.

A system to monitor for indications of opioid overdose event can comprise software instructions storable in memory of a first mobile computing device. The software instructions executable by one or more hardware processors of the first mobile computing device can cause the one or more hardware processors to continuously receive data indicative of one or more physiological parameters of a first user that is being monitored by one or more sensors; continuously compare each of the one or more physiological parameters with a corresponding threshold; determine an opioid overdose event is occurring or will soon occur based on the comparisons; trigger an alarm on the first mobile computing device based on the determination; and notify a second user of the alarm by causing a display of a second mobile computing device associated with the second user to display a status of an alarming physiological parameter of the first user.

The one or more hardware processors can further cause a display of the first mobile computing device to continuously update graphical representations of the one or more physiological parameters in response to the continuously received data. The one or more hardware processors can further display a user-selectable input to view additional information associated with the first user.

Selecting the user-selectable input can cause the display of the second mobile computing device to display one or more of trends and current value of the alarming physiological parameter. Selecting the user-selectable input can cause the display of the second mobile computing device to display a location of the first mobile computing device on a map. Selecting the user-selectable input can cause the display of the second mobile computing device to display a time of an initial alarm. Selecting the user-selectable input can cause the display of the second mobile computing device to provide access to directions to the first mobile computing device from a location of the second mobile computing device. Selecting the user-selectable input can cause the display of the second mobile computing device to provide access to call the first mobile computing device.

The one or more physiological parameters can be represented as dials on the display. The one or more physiological parameters can include one or more of oxygen saturation, heart rate, respiration rate, pleth variability, perfusion index, and respiratory effort index. The alarm can be an audible and visual alarm. Each of the corresponding thresholds can be adjustable based on characteristics of the first user to inhibit false-positive alarms.

The one or more hardware processors can further transmit indications of the one or more physiological parameters to a remote server. The one or more hardware processors can further transmit indications of the one or more physiological parameters to a medical monitoring hub for storage in memory of the medical monitoring hub. The one or more hardware processors can communicate wirelessly with a local Internet of Things connected device to receive additional data for use in the determination of the opioid overdose event. The one or more hardware processors can further notify emergency services of the alarm. The first and second mobile computing devices can be smart phones.

A method to monitor for indications of an opioid overdose event can comprise continuously receiving, with a first mobile computing device, data indicative of one or more physiological parameters of a first user that is being actively monitored by one or more sensors; continuously comparing, with the first mobile computing device, each of the one or more physiological parameters with a corresponding threshold; determining, with the first mobile computing device, an opioid overdose event is occurring or will soon occur based on the comparisons; triggering, with the first mobile computing device, an alarm on the first mobile computing device based on the determination; and notifying, with the first mobile computing device, a second user of the alarm by causing a display of a second mobile computing device associated with the second user to display a status of an alarming physiological parameters of the first user.

The method can further comprise causing a display of the first mobile computing device to continuously update graphical representations of the one or more physiological parameters in response to the continuously received data. The method can further comprising displaying a user-selectable input to view additional information associated with the first user.

Selecting the user-selectable input can cause the display of the second mobile computing device to display one or more of trends and current value of the alarming physiological parameter. Selecting the user-selectable input can cause the display of the second mobile computing device to display a location of the first mobile computing device on a map. Selecting the user-selectable input can cause the display of the second mobile computing device to display a time of an initial alarm. Selecting the user-selectable input can cause the display of the second mobile computing device to provide access to directions to the first mobile computing device from a location of the second mobile computing device. Selecting the user-selectable input can cause the display of the second mobile computing device to provide access to call the first mobile computing device.

The one or more physiological parameters can be represented as dials on the display. The one or more physiological parameters can include one or more of oxygen saturation, heart rate, respiration rate, pleth variability, perfusion index, and respiratory effort index. The alarm can be an audible and visual alarm. Each of the corresponding thresholds can be adjustable based on characteristics of the first user to inhibit false-positive alarms.

The method can further comprise transmitting indications of the one or more physiological parameters to a remote server. The method can further comprise transmitting indications of the one or more physiological parameters to a medical monitoring hub for storage in memory of the medical monitoring hub. The method can further comprise communicating wirelessly with a local Internet of Things connected device to receive additional data for use in the determination of the opioid overdose event. The method can further comprise notifying emergency services of the alarm. The first and second mobile computing devices can be smart phones.

For purposes of summarizing the disclosure, certain aspects, advantages and novel features are discussed herein. It is to be understood that not necessarily all such aspects, advantages or features will be embodied in any particular embodiment of the invention, and an artisan would recognize from the disclosure herein a myriad of combinations of such aspects, advantages or features.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

FIGS. 3A-3E illustrate various example software applications to provide information, notifications, and alerts to opioid users, first responders, medical personnel, and friends.

FIGS. 18A1-18A25 illustrate various example software applications to trigger an alarm and notify a friend when an opioid overdose is indicated.

DETAILED DESCRIPTION

Figure 1A:
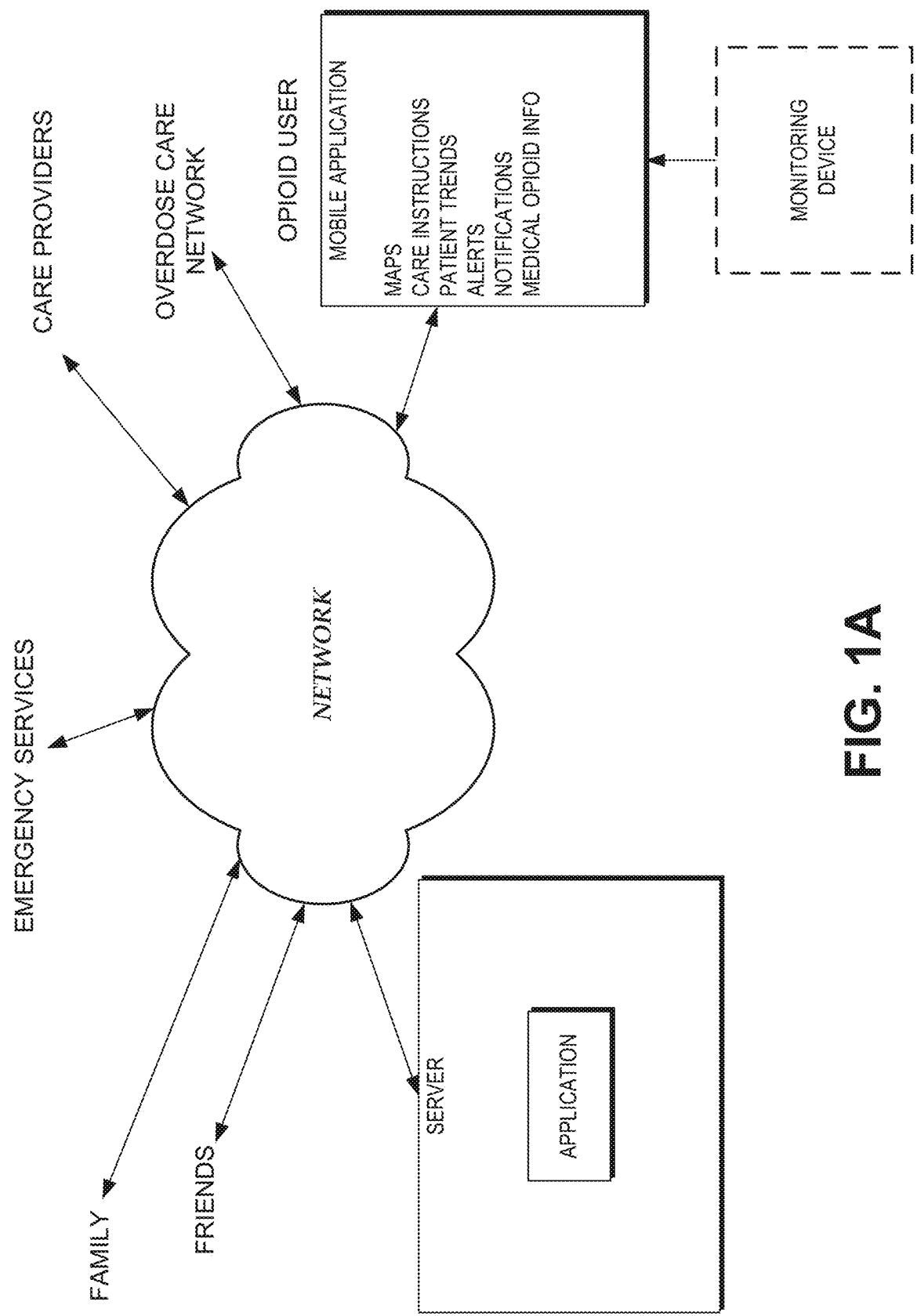
FIG. 1A is an overview of an example opioid use monitoring system.

Although certain embodiments and examples are described below, this disclosure extends beyond the specifically disclosed embodiments and/or uses and obvious modifications and equivalents thereof. Thus, it is intended that the scope of this disclosure should not be limited by any particular embodiments described below.

Overview

An application for a mobile computing device that is used in conjunction with a physiological parameter monitoring assembly to detect physiological parameters of an opioid user can comprise determining a physiological condition of the opioid user based at least in part on the physiological parameters, and providing notifications based at least in part on the physiological condition of the opioid user. The physiological parameter monitoring assembly can be a pulse oximeter that includes a sensor and a signal processing device. Examples of physiological parameters that can be monitored are peripheral oxygen saturation ($SpO_2$), respiration, and perfusion index (PI). The application can determine the physiological condition of the user based on the $SpO_2$ alone, respiration alone, PI alone, a combination of the $SpO_2$ and respiration, a combination of the $SpO_2$ and PI, a combination of the respiration and the PI, or a combination of the $SpO_2$, respiration, and PI.

The application can request user input and determine the physiological condition of the user based at least in part on the received user input and the physiological parameters from the pulse oximeter. The determination of the user's condition can be based on the user input and one or more of peripheral oxygen saturation ($SpO_2$), respiration, and perfusion index (PI). The application can learn, based at least in part on stored physiological parameters, trends in user's the physiological reaction to opioid use to better anticipate overdose events of the user.

The application can notify one or more of caregivers, loved ones, friends, and first responders of an overdose event. The application can provide "everything OK" notifications upon request or periodically to concerned family and friends. The application can provide detailed care instructions to first responders. The application can provide the location of the user, the location of the closest medication to reverse the effects of an opioid overdose, or the location of the closest medical personnel. The application can provide one or more of visual, audible, and sensory (vibration) alerts to the user with increasing frequency and intensity to the user.

An application for a mobile computing device that is used in conjunction with a sensor and a signal processing device to detect abnormally low blood oxygen saturation that is indicative of an overdose event in a user can comprise triggering an alarm, and notifying others of the overdose event. This increases the likelihood that opioid users, their immediate personal networks, and first responders are able to identify and react to an overdose by administrating medication to reverse the effects of the overdose. Such medication can be considered an opioid receptor antagonist or a partial inverse agonist. Naloxone or Narcan® is a medication that reverses the effect of an opioid overdose and is an opioid receptor antagonist. Buprenorphine or Subutex® is an opioid used to treat opioid addiction. Buprenorphine combined with naloxone or Suboxone® is a medication that may also be used to reverse the effect of an opioid overdose. Other example medications are naltrexone, nalorphine, and levallorphan. Administration can be accomplished by intravenous injection, intramuscular injection, and intranasally, where a liquid form of the medication is sprayed into the user's nostrils. Administration of the medication can also occur via an endotracheal tube, sublingually, where a gel or tablet of the medication is applied under the tongue, and transdermally, where the medication can be a gel applied directly to the skin or within a transdermal patch applied to the skin.

A system to monitor a user for an opioid overdose condition can comprise a sensor configured to monitor one or more physiological parameters of a user, a signal processing device configured to receive raw data representing the monitored one or more physiological parameters and to provide filtered parameter data; and a mobile computing device configured to receive the one or more physiological parameters from the signal processing device. The mobile computing device comprises a user interface, a display, network connectivity, memory storing an application as executable code, and one or more hardware processors. The application monitors the physiological parameters to determine a condition of the user and provides notifications to the user, to a crowd-sourced community of friends, family, and other opioid users that have also downloaded the application onto their computing devices, and to emergency providers and medical care personnel.

Home pulse oximetry monitoring systems for opioid users can include a pulse oximeter, such as a Masimo Rad-97 Pulse CO-Oximeter®, for example, and sensors, such as Masimo LNCS® adhesive sensors and the like, to detect blood oxygen levels and provide alerts and alarms when the opioid user's blood oxygen level drops below a threshold. The home monitoring system can provide alarm notifications that can alert a family member, remote caregiver, and a first responder, for example, to awaken the opioid user and to administer the antidote for an opioid overdose, such as an opioid receptor antagonist.

The mobile computing device can be configured to receive the filtered parameter data from the signal processing device; display representations of the filtered parameter data on the display, where the filtered parameter data includes at least oxygen saturation data for the oxygen level in the blood of the user; compare a current oxygen saturation value to a minimum oxygen saturation level; trigger an alarm when the current oxygen saturation value is below the minimum oxygen saturation level; and provide notifications over a network to another when the current oxygen saturation value is below the minimum oxygen saturation level.

The display can display the representations of the filtered parameter data as dials indicating acceptable and acceptable ranges. The filtered parameter data can include one or more of heart rate data, respiration rate data, pleth variability data, perfusion index data, and respiratory effort index data. The application can provide notifications to the user and can provide notifications to others. The notification can be one or more of a text message, an email, and a phone call. The notification can include a current value of oxygen saturation and a graph indicting a trend of the oxygen saturation levels. The notification can further include one or more of a phone number of the user, a location of the user, directions to the location of the user, a closest location of naloxone or other medication used to reverse the effects of an opioid overdose. The notification can be an automatic call to emergency responders.

A system to monitor a user for an opioid overdose condition can comprise one or more computing devices associated with an opioid overdose monitoring service. The opioid overdose monitoring service can be configured to identify opioid monitoring information from at least one physiological monitoring system associated with a user, where the opioid monitoring information comprises one of an overdose alert and a non-distress status, retrieve over a network notification information associated with the user, where the notification information includes first contact information associated with the overdose alert and second contact information associated with the non-distress status, send an overdose notification using the first contact information in response to the opioid monitoring information that indicates the overdose alert, and send a non-distress notification using the second contact information in response to the opioid monitoring information that indicates the non-distress status.

The system can further comprise a physiological monitoring system comprising a sensor configured to monitor one or more physiological parameters of the user and a signal processing board configured to receive raw data representing the monitored one or more physiological parameters and to provide filtered parameter data, and a mobile computing device comprising a display, network connectivity, memory storing executable code, and one or more hardware processors. The mobile computing device can be configured to receive the filtered parameter data from the signal processing board, display representations of the filtered parameter data on the display, where the filtered parameter data includes at least oxygen saturation data for the oxygen level in the blood of the user, compare a current oxygen saturation value to a minimum oxygen saturation level, and trigger an alarm when the current oxygen saturation value is below the minimum oxygen saturation level.

The mobile computing device can be configured to receive the filtered parameter data from the signal processing board, generate the opioid monitoring information based on the filtered parameter data, and send the opioid monitoring information over a network to the opioid overdose monitoring service. The filtered parameter data can include one or more of a current oxygen saturation value, heart rate data, respiration rate data, pleth variability data, perfusion index data, and respiratory effort index data. The overdose and non-distress notifications can comprise one or more of a text message, an email, and a phone call. The overdose and non-distress notifications can include a current value of oxygen saturation and a graph indicting a trend of the oxygen saturation levels. The overdose notification can comprise one or more of a phone number of the user, a location of the user, directions to the location of the user, a closest location of naloxone or other medication used to reverse the effects of an opioid overdose. The overdose notification can automatically calls emergency responders. The network can be the Internet.

A kit for monitoring for an opioid overdose event can comprise a sensor to sensor physiological parameters and a medical monitoring hub device to receive indications of the sensed physiological parameters and to receive an indication of an opioid overdose event. The kit can further comprise a delivery device to deliver medication in response to the indication of the opioid overdose event. The delivery device can automatically administers an opioid receptor antagonist in response to the indication of an opioid overdose event. The delivery device can comprise a patch that includes a reservoir with the medication, a needle, and a battery. The hub device can comprise memory for storage of the indication of the sensed physiological parameters. The hub device can receive and store data from monitoring devices other than the sensor. The data from the monitoring devices can comprise data associated with a well-being of a user. The kit may be available without a prescription.

FIG. 1A is an overview of an example opioid use monitoring/notification system. The opioid users' support network can include friends, family, emergency services, care providers, and overdose care networks, for example that communicate over a network, such as the Internet. The support network receives notifications and/or status updates of the opioid user's condition. An optional monitoring device can monitor the opioid user's respiration and other biological parameters, such as heart rate, blood oxygen saturation, perfusion index, for example, and provides the parameters to the smart device. An application running on the smart device can determine whether an opioid overdose event is imminent and/or occurring. The application can also provide additional information, such as care instructions, patient trends, medical opioid information, care instruction, user location, the location of naloxone, buprenorphine, buprenorphine in combination with naloxone, or other medication used to reverse the effects of an opioid overdose, and the like. The support network, after receiving a notification, can communicate with a central server to obtain the additional information.

Figure 1B:
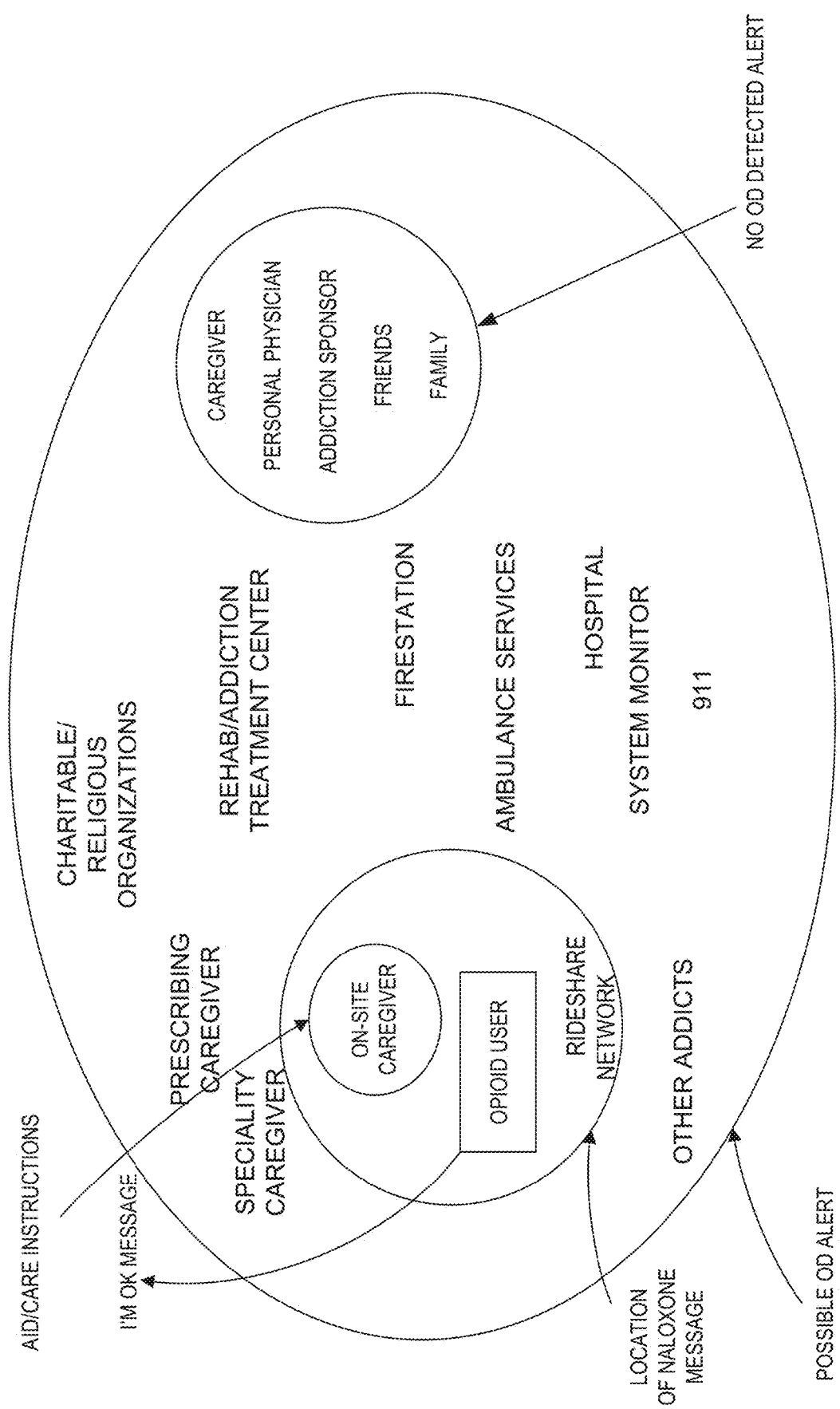
FIG. 1B is a diagrammatic representation of an example network associated with monitoring opioid.

FIG. 1B is a diagrammatic representation of an example support network associated with monitoring opioid use. The diagram illustrates an example of an opioid use support network. An opioid user may want to notify friends, family, and caregivers when they are in need of emergency care due to indications that an opioid overdose is imminent or occurring. The diagram illustrates an example of an opioid use support network. Subnetworks within the support network may receive different notifications. For example, caregivers, such as emergency 911 services, rideshare services, such as Uber® and Lyft®, for example, treatment centers, prescribing caregivers, specialty caregivers, ambulance services can receive possible overdose alerts in order to provide the immediate life-saving care to the user; an on-site caregiver can receive care instructions; friends and family can receive periodic status messages indicating no overdose event occurring; and transportation services can receive messages with the location of medications used to reverse the effects of an opioid overdose, such as naloxone, buprenorphine, a combination of buprenorphine and naloxone, and the like. Other subnetworks receiving different notifications are possible.

Figure 1C:
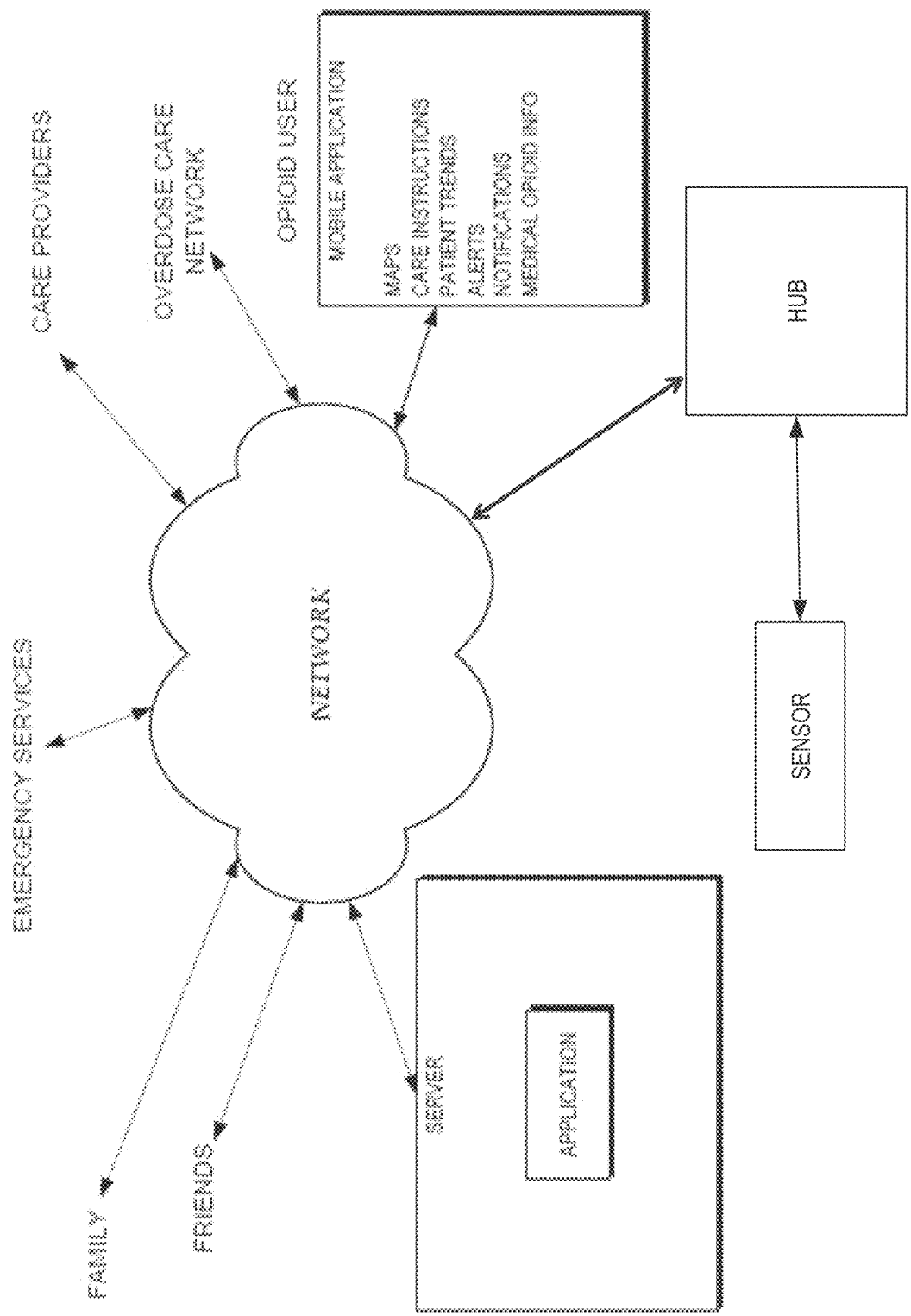
FIG. 1C is an overview of another example opioid use monitoring system.

FIG. 1C is an overview of another example opioid use monitoring system. As illustrated above in FIG. 1A, the opioid users' support network can include friends, family, emergency services, care providers, and overdose care networks, for example, that communicate over a network, such as the Internet. The support network receives notifications and/or status updates of the opioid user's condition. A monitoring device including a sensor can monitor the opioid user's respiration and other biological parameters, such as heart rate, blood oxygen saturation, perfusion index, for example, and provide the parameters to a HUB device that can communicate over the network. An example of a HUB device is illustrated in FIG. 6H. The HUB device receives the sensor data from the sensor. The HUB device can send the sensor data over the network to the server. The HUB device can at least partially processes the sensor data and sends that at least partially processed sensor data to the server. The server processes the sensor data or the at least partially processed sensor data and determines whether an overdose event is imminent and/or occurring. When an overdose event is imminent and/or occurring, the server notifies the support network and the mobile application on the opioid user's mobile device.

Instrumentation-Sensor and Signal Processing Device

Figure 2A:
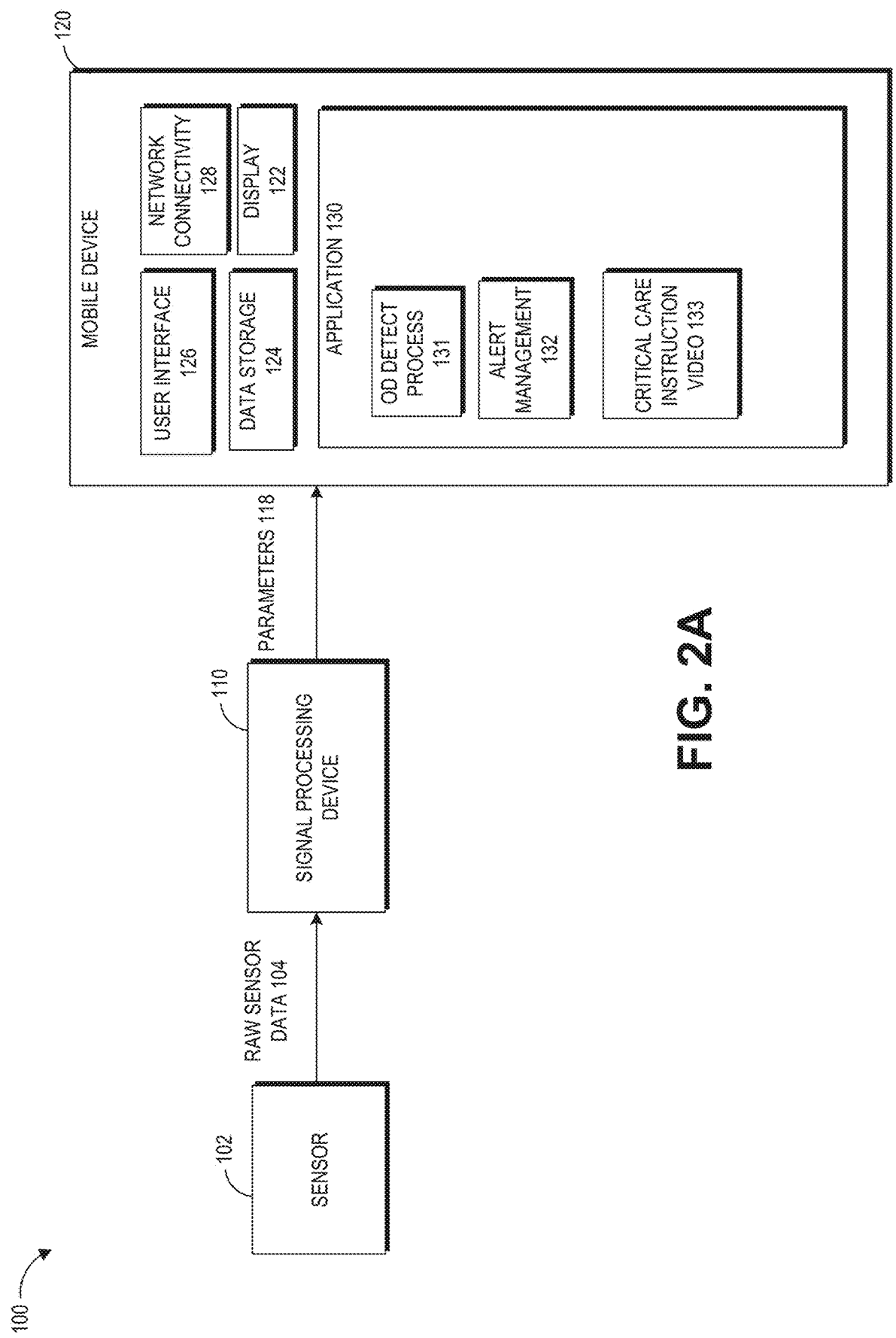
FIG. 2A is a block diagram of an example physiological monitoring system.

FIG. 2A illustrates an example physiological monitoring system 100. The illustrated physiological monitoring system 100 includes a sensor 102, a signal processing device 110, and a mobile computing device 120.

The sensor 102 and the signal processing device 110 can comprise a pulse oximeter. Pulse oximetry is a noninvasive method for monitoring a person's oxygen saturation. The sensor 102 is placed on the user's body and passes two wavelengths of light through the body part to a photodetector. The sensor 102 can provide raw data 104 to the signal processing device 110, which determines the absorbance's of the light due to pulsating arterial blood. The pulse oximeter generates a blood-volume plethysmograph waveform from which oxygen saturation of arterial blood, pulse rate, and perfusion index, among other physiological parameters, can be determined, and provides physiological parameters 118 to the mobile computing device 120.

The pulse oximeter can be transmissive, where the sensor 102 is placed across a thin part of the user's body, such as a fingertip or earlobe, for example, or reflective, where the sensor 102 can be placed on the user's forehead, foot, or chest, for example.

The sensor 102 and the signal processing device 110 can be packaged together. The sensor 102 can be not packaged with the signal processing device 110 and communicates wirelessly or via a cable with the signal processing device 110.

Examples of pulse oximeters are the MIGHTYSAT RX fingertip pulse Oximeter®, the Rad-57® handheld pulse CO-oximeter, and the Rainbow® CO-oximeter, all by Masimo Corporation, Irvine, Calif., which are capable of being secured to a digit, such as a finger.

Because opioid users may want to be discrete when monitoring opioid use for indications of an overdose event, sensors 102 that are not visible may provide additional confidentiality for the user. The sensor 102 can be applied to a toe and the signal processing device 110 can comprise an ankle brace. The sensor 102 can be a ring on the user's finger or a bracelet on the user's wrist, and the signal processing device 110 can be within an arm band hidden under the user's sleeve. The sensor 102 or the sensor 102 and the signal processing device 110 can be integrated into a fitness device worn on the user's wrist. Such pulse oximeters can be reflective or transmissive. The sensor 102 can be an ear sensor that is not readily visible.

Other varieties of sensors 102 can be used, for example adhesive sensors, combination reusable/disposable sensors, soft and/or flexible wrap sensors, infant or pediatric sensors, multisite sensors, or sensors shaped for measurement at a tissue site such as an ear.

Other sensors 102 can be used to measure physiological parameters of the user. For example, a modulated physiological sensor can be a noninvasive device responsive to a physiological reaction of the user to an internal or external perturbation that propagates to a skin surface area. The modulated physiological sensor has a detector, such as an accelerometer, configured to generate a signal responsive to the physiological reaction. A modulator varies the coupling of the detector to the skin so as to at least intermittently maximize the detector signal. A sensor processor controls the modulator and receives an effectively amplified detector signal, which is processed to calculate a physiological parameter indicative of the physiological reaction. A modulated physiological sensor and corresponding sensor processor are described in U.S. Publication No. 2013/0046204 to Lamego et al., filed Feb. 21, 2013, titled "MODULATED PHYSIOLOGICAL SENSOR" and assigned to Masimo Corporation, Irvine, Calif., which is hereby incorporated by reference herein.

The sensor 102 can include an electroencephalograph ("EEG") that can be configured to measure electrical activity along the scalp. The sensor 102 can include a capnometer or capnograph that can be configured to measure components of expired breath.

An acoustic sensor 102 can be used to determine the user's respiration rate. An acoustic sensor utilizing a piezoelectric device attached to the neck is capable of detecting sound waves due to vibrations in the trachea due to the inflow and outflow of air between the lungs and the nose and mouth. The sensor outputs a modulated sound wave envelope that can be demodulated so as to derive respiration rate. An acoustic respiration rate sensor and corresponding sensor processor is described in U.S. Publication No. 2011/0125060 to Telfort et al., filed Oct. 14, 2010, titled "ACOUSTIC RESPIRATORY MONITORING SYSTEMS AND METHODS" and assigned to Masimo Corporation, Irvine, Calif., which is hereby incorporated by reference herein.

The mobile computing device 120 can include an accelerometer that is configured to detect motion of the mobile computing device 120. When the user holds the mobile computing device 120 or attaches the mobile computing device 120 to his clothing in such a way that the accelerometer detects motion of the user, then the accelerometer can be used to detect lack of motion of the user. The lack of user motion can be used to determine the user's condition, as described below.

When the user holds the mobile computing device 120, the accelerometer can sense vibrations from the user indicative of the user's heart rate. A lack of vibrations sensed by the accelerometer can indicate no heart rate and reduced occurrences of vibrations sensed by the accelerometer can indicate cardiac distress. The indications of cardiac activity sensed by the accelerometer in the mobile computing device can be used to determine the user's condition, as described below.

The sensor 102 can be a centroid patch worn by the user that includes an accelerometer. Data indicative of the movement of the accelerometer can be transmitted wirelessly to the mobile computing device 120. Based on movement detected by the accelerometer, the application detects the respiration rate of the user. An oxygen sensor configured to monitor the user's breath can wirelessly transmit an indication of the oxygen present in the user's exhaled breath.

The physiological sensor 102 and the mobile computing device 120 can be connected via a cable or cables and the signal processing device 110 can be connected between the sensor 102 and the mobile computing device 120 to conduct signal processing of the raw data 104 before the physiological parameters 118 are transmitted to the mobile computing device 120. A mobile physiological parameter monitoring system is described in U.S. Pat. No. 9,887,650 to Muhsin et al., issued on Jan. 30, 2018, titled "PHYSIOLOGICAL MONITOR WITH MOBILE COMPUTING DEVICE CONNECTIVITY", and assigned to Masimo Corporation, Irvine, Calif., which is hereby incorporated by reference herein.

In various oximeter examples, the sensor 102 provides data 104 in the form of an output signal indicative of an amount of attenuation of predetermined wavelengths (ranges of wavelengths) of light by body tissues, such as, for example, a digit, portions of the nose or ear, a foot, or the like. The predetermined wavelengths often correspond to specific physiological parameter data desired, including for example, blood oxygen information such as oxygen content (SpOC), oxygen saturation (SpO$_2$), blood glucose, total hemoglobin (SbHb), methemoglobin (SbMet), carboxyhemoglobin (SpCO), bulk tissue property measurements, water content, pH, blood pressure, respiration related information, cardiac information, perfusion index (PI), pleth variability indices (PVI), or the like, which can be used by the mobile computing device 120 to determine the condition of the user. Sensor data 104 can provide information regarding physiological parameters 118 such as EEG, ECG, heart beats per minute, acoustic respiration rate (RRa), breaths per minute, end-tidal carbon dioxide (EtCO$_2$), respiratory effort index, return of spontaneous circulation (ROSC), or the like, which can be used to determine the physiological condition of the user.

Referring to FIG. 2A, the sensor 102 can transmit raw sensor data 104 to the signal processing device 110, and the signal processing device 110 can convert the raw sensor data 104 into data representing physiological parameters 118 for transmission to the mobile computing device 120 for display, monitoring and storage. The sensor data 104 can be transmitted wirelessly, using Bluetooth®, near field communication protocols, Wi-Fi, and the like or the sensor data 104 can be transmitted to the signal processing device 110 through a cable.

The sensor data 104 can be corrupted by noise due to patient movement, electromagnetic interference, or ambient light, for example. The physiological parameter monitoring system 100 can apply noise filtering and signal processing to provide the physiological parameters 118 for analysis and display on the mobile computing device 120. Such complex processing techniques can exceed the processing capabilities of the mobile computing device 120, and therefore the signal processing device 110 can handle signal processing of the raw sensor data 104 and transmit the processed physiological parameters 118 to the mobile computing device 120.

In the context of pulse oximetry, the signal processing device 110 can use adaptive filter technology to separate an arterial signal, detected by a pulse oximeter sensor 102, from the non-arterial noise (e.g. venous blood movement during motion). During routine patient motions (shivering, waving, tapping, etc.), the resulting noise can be quite substantial and can easily overwhelm a conventional ratio based oximetry system. This can provide accurate blood oxygenation measurements even during patient motion, low perfusion, intense ambient light, and electrocautery interference. Accordingly, false alarms can be substantially eliminated without sacrificing true alarms.

The signal processing device 110 can transmit the physiological parameters 118 wirelessly, using Bluetooth®, near field communication protocols, Wi-Fi, and the like to the mobile computing device 120, or the signal processing device 110 can transmit the physiological parameters 118 to the mobile computing device 120 through a cable.

Figure 6A:
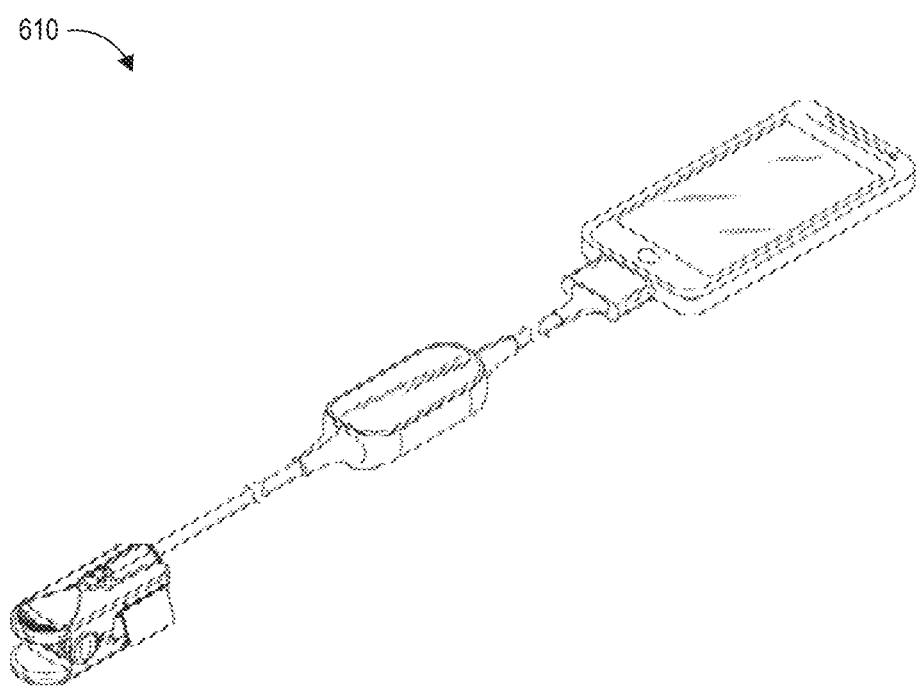
FIGS. 6A-6J illustrate various examples of physiological parameter sensors and signal processing devices.
Figure 6C:
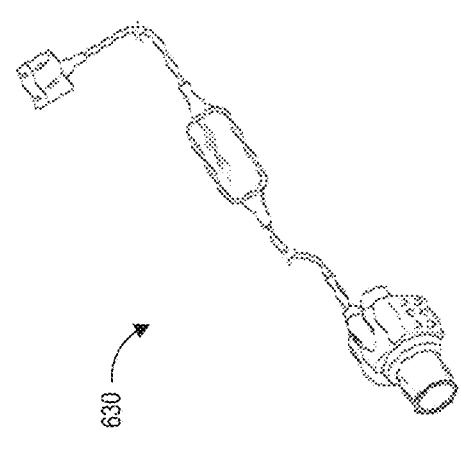
Figure 6D:
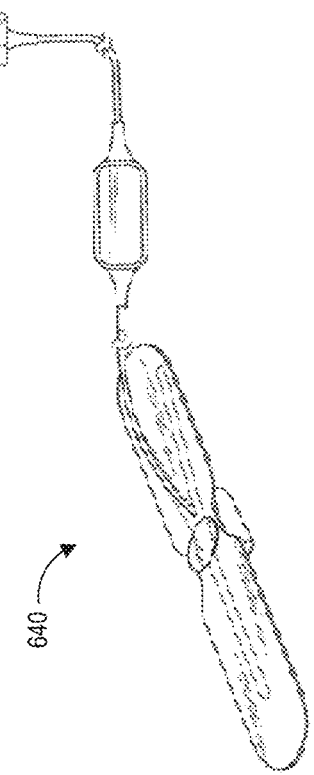
Figure 6B:
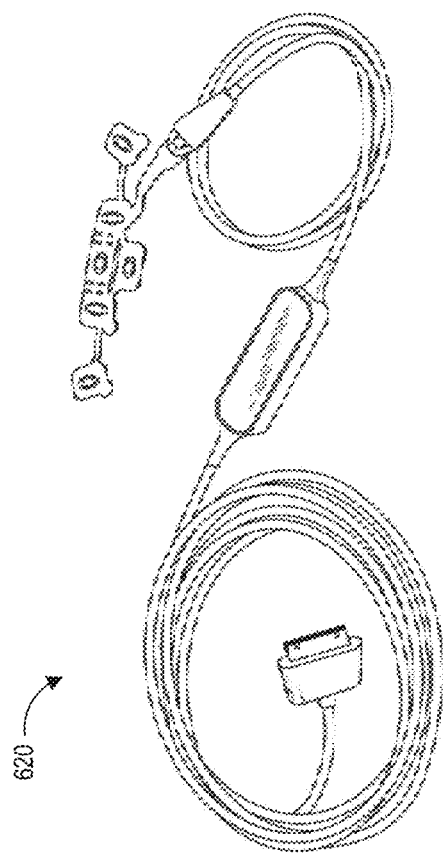
Figure 6E:
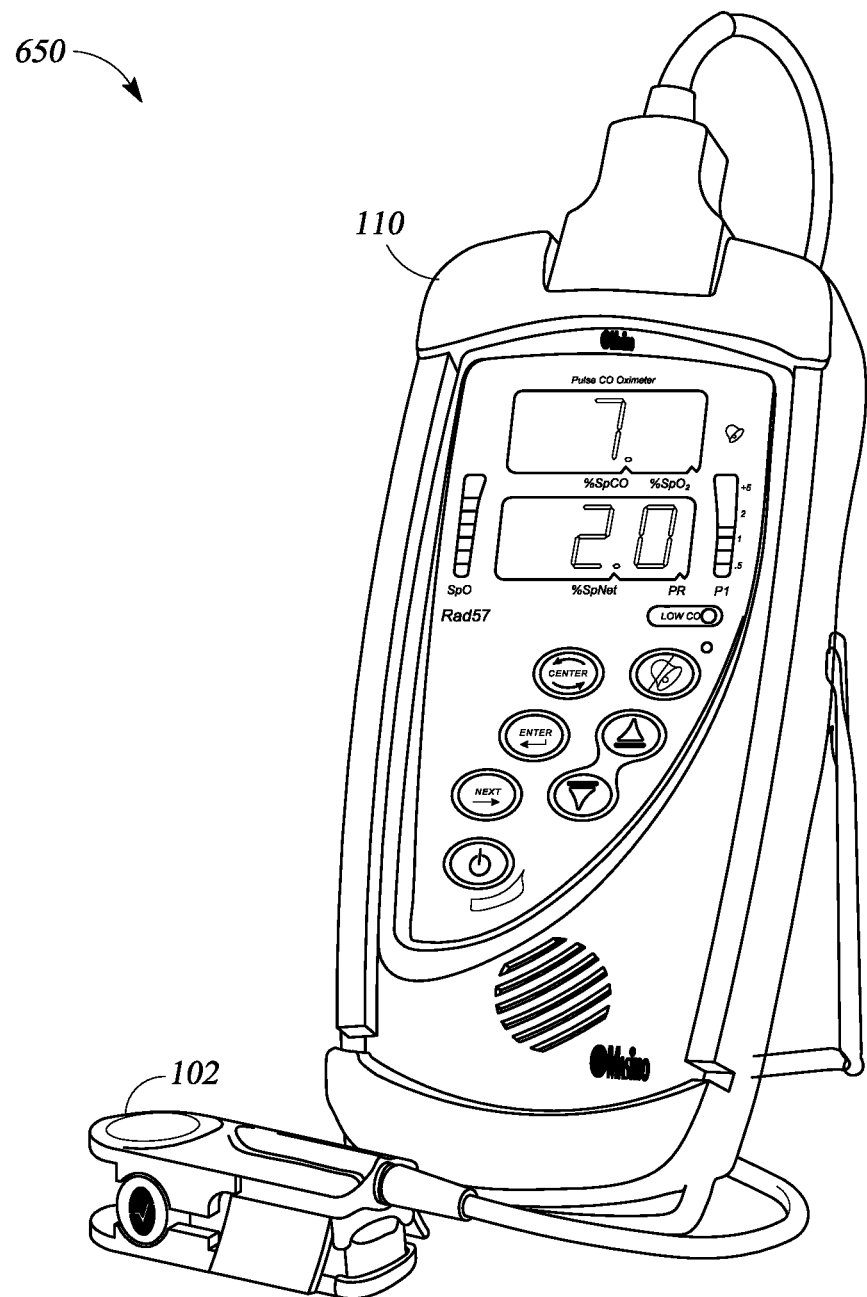
Figure 6F:
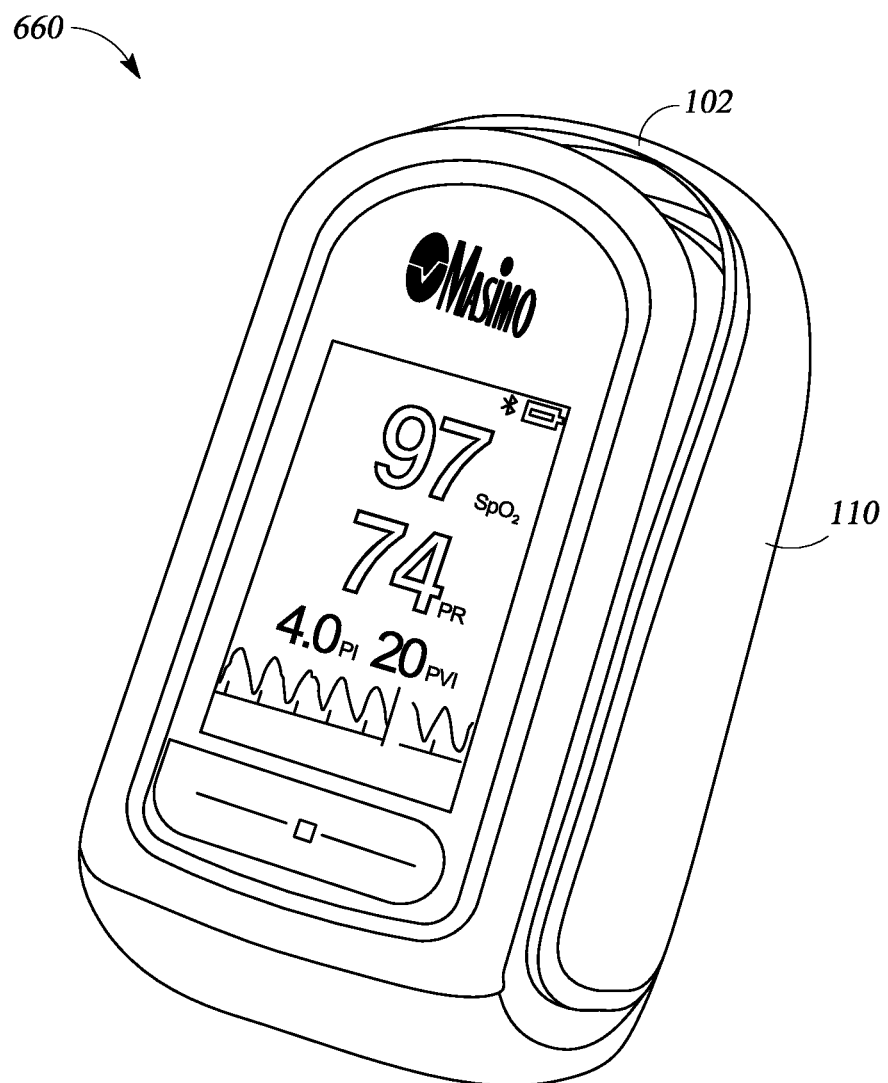
Figure 6G:
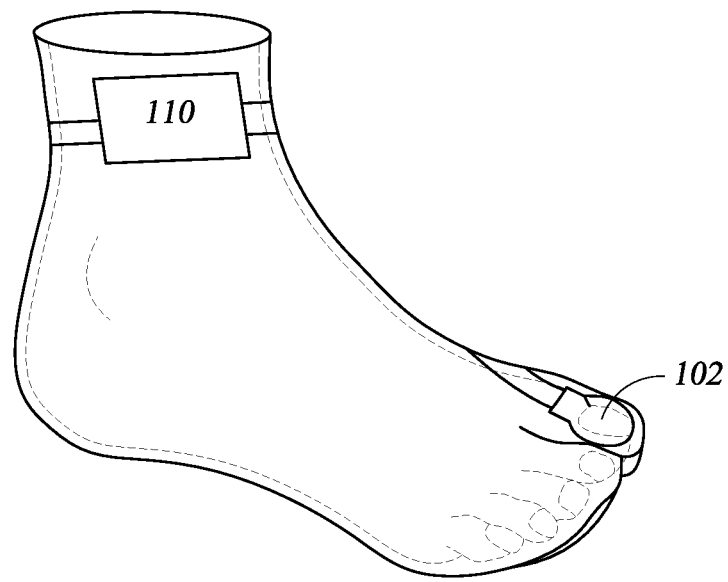
Figure 6G:
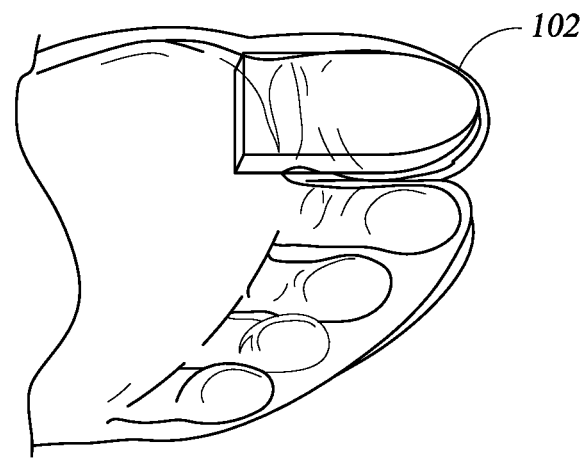
Figure 6H:
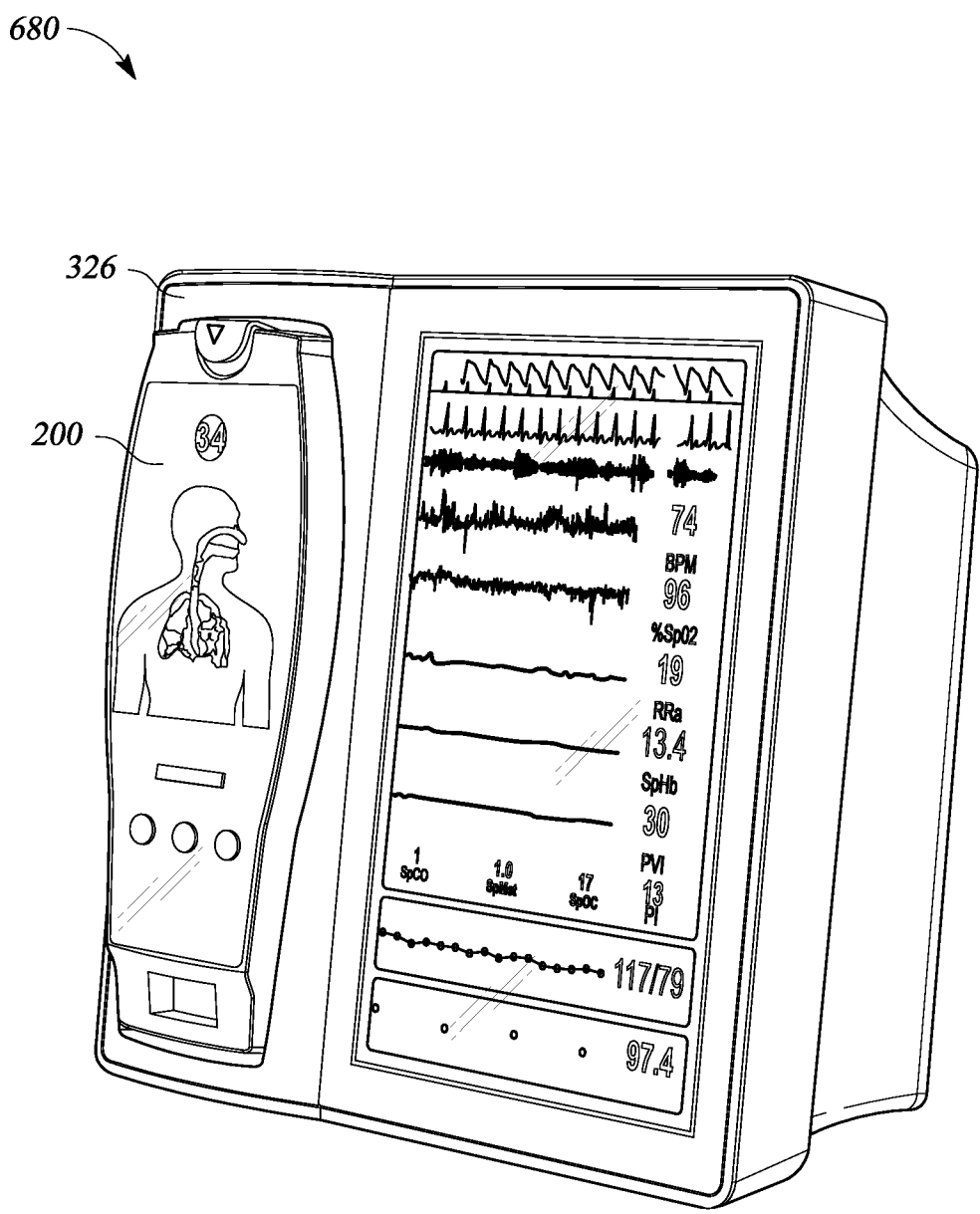

FIGS. 6A-6J illustrate various example sensors 102 and signal processing devices 110. FIG. 6A illustrates a mobile physiological monitoring system 610 that includes a fingertip pulse oximeter sensor 102 that is connected to the mobile computing device 120, which is illustrated as a smartphone, through a cable that includes the signal processing device 110.

FIGS. 6B-6D illustrate other example mobile physiological sensor assemblies that can be in physical communication with a user to collect the user's physiological data and send indications of the user's physiological parameters to the mobile computing device 120. FIG. 6B illustrates a mobile physiological sensor assembly 620 that includes an electroencephalograph ("EEG") that can be configured to measure electrical activity along the scalp. FIG. 6C illustrates a mobile physiological sensor assembly 630 that includes a capnometer or capnograph that can be configured to measure components of expired breath. FIG. 6D illustrates a mobile physiological sensor assembly 640 that includes an acoustic respiratory monitor sensor that can be configured to measure respiration rate using an adhesive sensor with an integrated acoustic transducer.

FIG. 6E illustrates the Rad-57® handheld pulse CO-oximeter 650 by Masimo Corporation, Irvine Calif. The oximeter 650 has a fingertip oximeter sensor 102 that communicates the raw data 104 through a cable to the signal processing device 110, which includes display capabilities.

FIG. 6F illustrates the MIGHTYSAT RX fingertip pulse Oximeter® 660 by Masimo Corporation, Irvine, Calif. The sensor 102 and the signal processing device 110 of the oximeter 660 are integrated into a single package.

FIG. 6G illustrates a physiological parameter assembly 670 comprising a sensor 102 applied to the toe and a signal processing device 110 in an ankle band for discreetly monitoring for opioid overdose conditions.

FIG. 6H illustrates a monitoring hub 680 comprising a ROOT® monitoring hub 326 with a Radical-7® pulse oximeter 200, both by Masimo Corporation, Irvine, Calif. The medical monitoring hub 680 can expand monitoring capabilities by bringing together signal processing and display for multiple physiological parameters, such as brain function monitoring, regional oximetry, and capnography measurements.

Figure 6I:
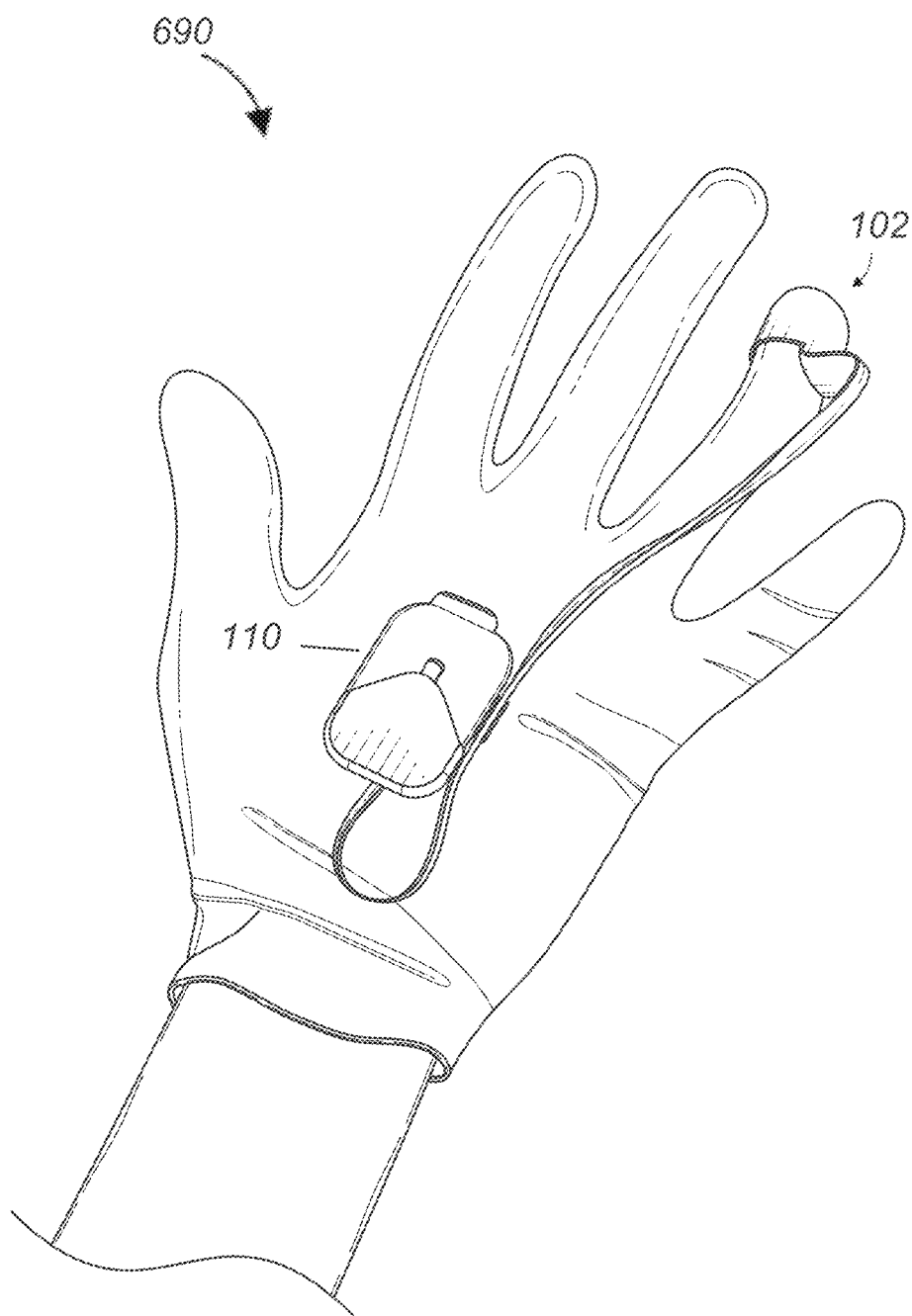

FIG. 6I illustrates a physiological parameter assembly 690 comprising a sensor 102 and a signal processing device 110 that can be worn as a glove. When the glove is placed on the user's hand, the sensor 102 can be placed on one of the fingertips. The sensor 102 can be a disposable sensor. The sensor 102 can be built inside or outside the fingers of the glove. The sensor 102 can be integrated to the fingers of the glove. The cable of the signal processing device 110 can be integrated to the glove. Advantageously, the glove is easy to wear, stays in place, and can be easily removed when the user is not in need of opioid overdose monitoring. The glove 690 can fasten at the wrist with a strap, hook and loop fastener, and the like. The sensor 110 can be wireless and communicates with the mobile device 120 using wireless technology, such as Bluetooth®, and the like.

Figure 6J:
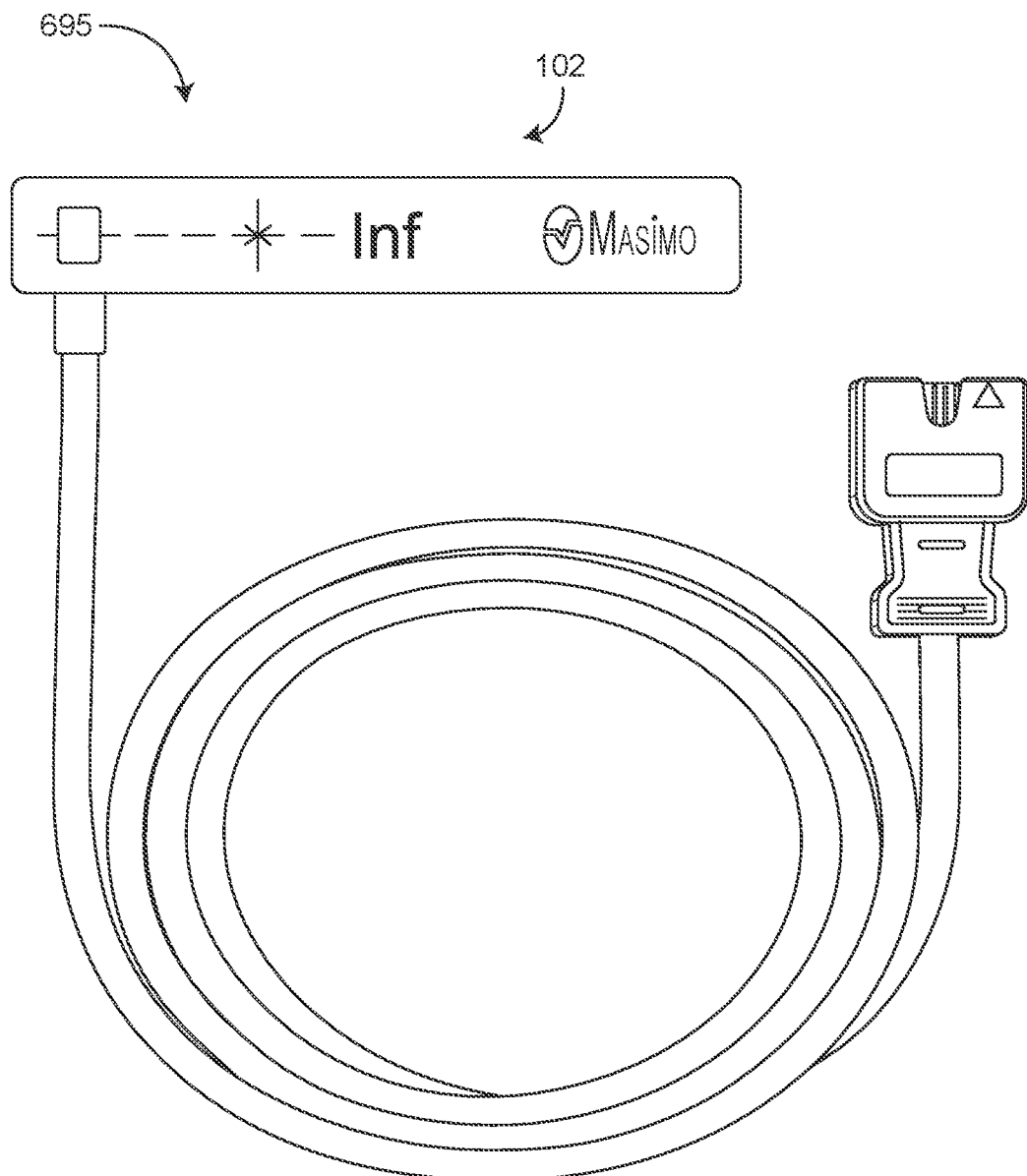

FIG. 6J illustrates a physiological parameter assembly 695 comprising a sensor 102 and a cable for connection to a signal processing device. The sensor 102 can be a disposable sensor. The sensor 102 can be placed around a finger. The sensor 102 can communicate sensor data wirelessly.

Instrumentation-Mobile Computing Device

Any mobile computing device 120 that is compatible with the physiological parameter assembly that includes the sensor 102 and the signal processing device 110 can be used. A compatible mobile computing device can be one of a wide range of mobile devices such as, but not limited to a mobile communications device (such as a smartphone), laptop, tablet computer, netbook, PDA, media player, mobile game console, wristwatch, wearable computing device, or other microprocessor based device configured to interface with the signal processing device 110 and provide notifications based at least in part on the monitored physiological parameters 118.

Referring to FIG. 2A, the mobile computing device 120 can include a display 122 for display of the physiological parameters, for example in a user interface and/or software application, as discussed in more detail below. The display 122 can include a display screen such as an LED or LCD screen, and can include touch sensitive technologies in combination with the display screen. Mobile computing device 120 can include software configured to display some or all of the output measurement data on the display screen. The data display can include numerical or graphical representations of blood oxygen saturation, heart rate, respiration rate, pleth variability, perfusion index, and/or a respiratory efforts index, and may simultaneously display numerical and graphical data representations.

The mobile computing device 120 can include a user interface 126 that can receive user input. The user interface 126 can include buttons, a key pad, the touch sensitive technologies of the display screen 122, and other user input mechanisms typically found on the various example mobile computing devices 120.

The mobile computing device 120 can also include data storage 124, which can be configured for storage of the physiological parameters 118 and parameter history data and/or software applications that monitor the physiological parameters for an overdose indication and provide notifications. The storage 124 can be physical storage of the mobile computing device 120, and the storage 124 can be remote storage, such as on a server or servers of a data hosting service.

The mobile computing device 120 can also include a network connectivity feature 128 that provides network connection capabilities such as one or more of a cellular network, satellite network, Bluetooth, ZigBee, wireless network connection such as Wi-Fi or the like, and a wired network connection. The mobile computing device 120 can also include a data transfer port.

Application Functionality Overview

The mobile computing device 120 can include software such as an application 130 configured to manage the physiological parameters 118 from the physiological parameter monitoring device 110. The application functionality can include trend analysis, current measurement information, alarms associated with above/below threshold readings, reminders to take measurement data at certain times or cycles, display customization, iconic data such as hearts beating, color coordination, bar graphs, gas bars, charts, graphs, or the like, all usable by a caregiver or application user to provide medical monitoring of specified physiological parameters. The display 122 can display the physiological parameters 118 as numerical values, graphs, charts, dials and the like.

The application 130 via the mobile computing device 120 can also alert the user and/or person(s) designated by the user to an abnormal data reading. For example, an abnormally low blood oxygen saturation reading can cause the mobile computing device 120 to buzz, vibrate or otherwise notify the user of an abnormal reading, and to transmit a notification or alert to the user, the designated person(s) or medical personnel to a network via the network connectivity 128.

In addition, the application 130 includes one or more processes to monitor the physiological parameters 118 for the condition of the user, and in particular for signs of an opioid overdose. The application 130 can be set up by the user or a caregiver to notify another of the overdose event. This increases the likelihood that the opioid user, their immediate personal networks, and first responders are able to identify and react to an overdose by administrating medication used to reverse the effects of an opioid overdose, such as naloxone. Naloxone is an overdose-reversal drug. In some states, people who are or who know someone at risk for opioid overdose can go to a pharmacy or community-based program to get trained on naloxone administration and receive naloxone by "standing order," which means a patient-specific prescription is not required. When administered in time, naloxone can restore an overdose victim's breathing long enough for trained medical assistance to arrive. In some instances, other overdose reversal drugs can be used, such as buprenorphine, and combination of buprenorphine and naloxone, and the like.

The application 130 can include processes and information to monitor and provide care to opioid users, such as, but not limited to an overdose detection process 131 configured to determine the condition of the user and whether medical care is indicated based at least on the physiological parameters 118, an alert management process 132 configured to manage alerts to the user and others in the user's network based at least in part on condition of the user, and information for the care/treatment for opioid use, such as a critical care instruction video 133.

Opioid Overdose Monitoring

Figure 2B:
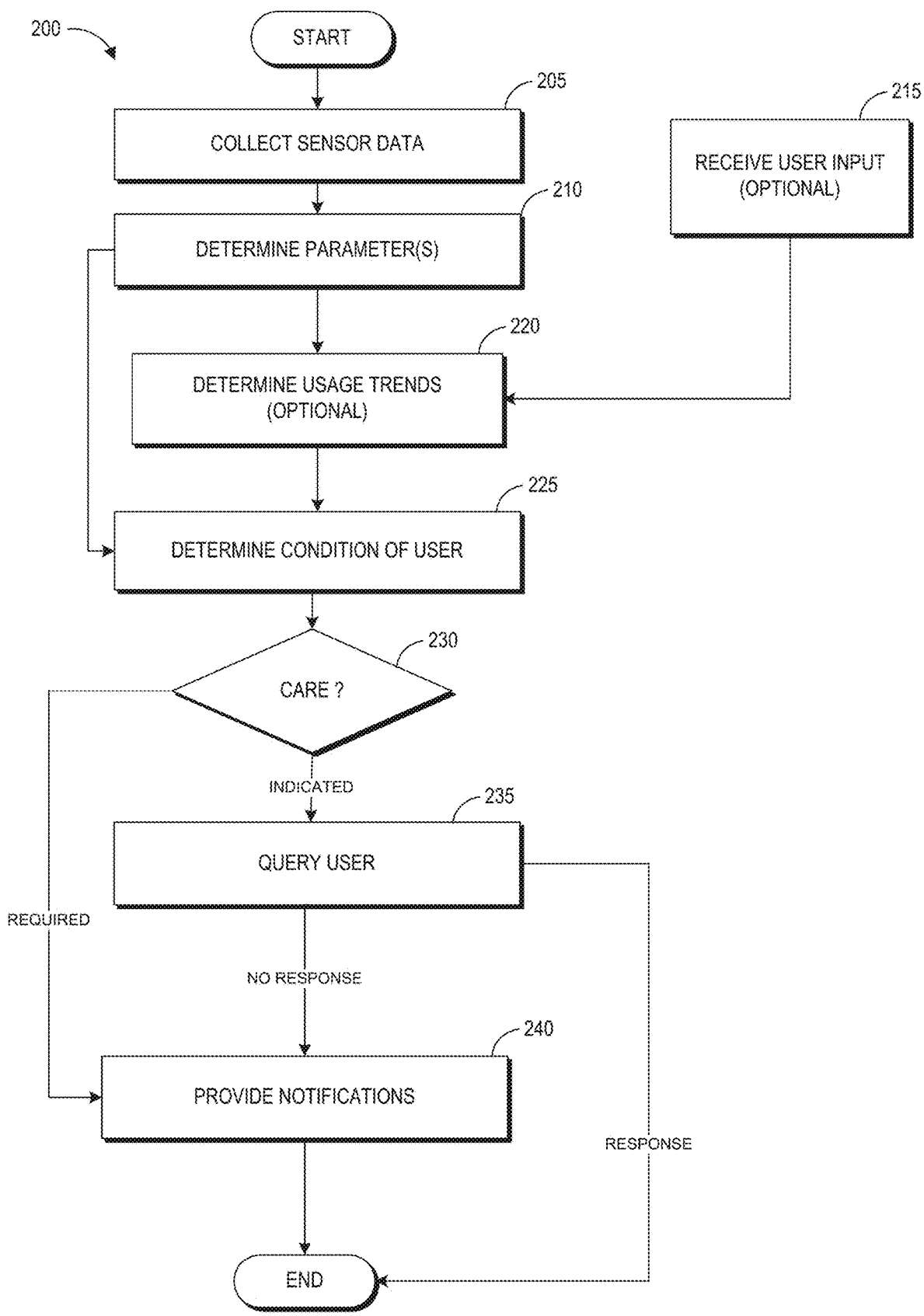
FIG. 2B is a flow chart of an example process to monitor physiological parameters for opioid use and provide notifications.

FIG. 2B illustrates an example process 200 to monitor physiological parameters 118 for opioid use and provide notifications. At block 205, the sensor 102 collects the raw data 104 from the user. In the case of a pulse oximeter sensor, the sensor 102 passes light, such as red and infrared light through a body part to a photodetector. The raw data 104 from the sensor 102 provides respiration information due to the absorbance of the light in the pulsating arterial blood.

At block 210, the signal processing device 110 receives the raw data 104 from the sensor 102, processes the raw data 104 to provide one or more parameters 118 to the mobile computing device 120. In the case of pulse oximetry, the signal processing device 110 generates a blood-volume plethysmograph waveform from which at least the peripheral oxygen saturation of arterial blood ($SpO_2$), respiration, pulse rate, and perfusion index (PI) may be determined. Other physiological parameters that may be determined are, for example, oxygen content (SpOC), blood glucose, total hemoglobin (SbHb), methemoglobin (SbMet), carboxyhemoglobin (SpCO), bulk tissue property measurements, water content, pH, blood pressure, cardiac information, and pleth variability indices (PVI). Sensor data 104 can provide information regarding physiological parameters 118 such as, for example, EEG, ECG, heart beats per minute, acoustic respiration rate (RRa), breaths per minute, end-tidal carbon dioxide ($EtCO_2$), respiratory effort index, and return of spontaneous circulation (ROSC).

User Input

At block 215, the application 130 via the mobile computing device 120 can query the user and receive user input. The mobile computing device 120 can present questions on the display 122 and the user can reply using the user interface 126. For example, the user can be asked for the information on the prescription label, the dosage and/or frequency of the opioid being consumed and any other drugs the user is consuming. The mobile computing device 120 can ask the user to input his weight, age, and other physical attributes that may be factors in the user's reaction to the opioid and dosages of the medication, such as naloxone and the like, used to reverse the effects of an overdose. The mobile computing device 120 can ask whether the user is OK or in need of assistance. A response from the user can indicate that the user is conscious and not overdosed. The application 130 can ask the user for a response when the analysis of the parameters 118 indicates an overdose event, and if a response is received, indicating the user is conscious and not overdosed, the application 130 can refine the threshold used to determine an overdose event. The mobile computing device 120 can confirm the users name and location.

Trends

At block 220, the application 130 can develop trends in the user's opioid usage using the physiological parameters 118 from past monitoring stored in the storage 124 as well as user input relating to weight, age, dosage, frequency, and additional drugs being consumed. The trends can be based on the parameters 118 and the user input, if any is received.

For example, opioid users that are also marijuana users can develop a greater tolerance for opioids. Further, opioids initially cause the perfusion index to increase due to vasodilation, then to decrease due to vasoconstriction. The increase and decrease of the perfusion index creates a perfusion profile. A user with a greater tolerance to opioids can have a different perfusion profile than a user that does not use marijuana in conjunction with opioids.

The application 130 can use the user input, if available, and stored physiological parameters, such as the perfusion profile, for example, and current physiological parameters to develop trends in the user's opioid usage and/or tolerance for opioids that can more accurately anticipate an overdose event. The application 130 can use past occurrences of "near misses" to further refine the conditions that may foreshadow an overdose event. A "near miss" is an event that provided indications of an overdose, such as an indication of respiration below a threshold, but did not result in an overdose event. The opioid dosage associated with a near miss can provide an indication of the user's tolerance to opioids and can be used by the application 130 to refine the determination of an imminent or occurring opioid overdose event.

By using the history of the physiological parameters 118 including the near-misses, and the user input, if available, the application 130 can learn which combination of events and parameter values indicate an overdose event may be imminent. Because time is of the essence in administrating medication, such as naloxone and the like, to reverse or reduce the effects of an overdose to an overdose victim, it is desirable to err in over-reporting, but too many false-positives of opioid notifications may desensitize responders. It is important that the application 130 learn the specific triggers for a specific user to increase accuracy in determining an overdose event for the specific user. The application 130 can learn the conditions leading up to an overdose event and refine its algorithm in order to notify others when help is needed and to discriminate against false-positive events.

The user's tolerance, as well as the user's physical attributes, such as weight and age, can be used by the application 130 to refine the quantity of medication that reverses or reduces the effects of an overdose, such as naloxone and the like, that should be administered to revive the user in an overdose event. The application 130 can monitor doses of the medication and report the dosages to clinicians who can determine whether the dosage is too high or too low.

The process 200 uses one or more of the user input, current physiological parameters, stored physiological parameters, "near miss" events, overdose events, to refine the indications of an overdose event so as to be able to more accurately determine the occurrence of an overdose event without notifying others of an overdose event that turns out to be false. Because time is of the essence in responding to an overdose victim, the application 130 may err on the side of over notification, but can learn the triggers for the specific user to avoid "crying wolf", which may result in others ignoring the notifications.

Data Analysis

At block 225, the application 130 determines the condition of the user based on one or more of the physiological parameters, user input, and trends. For example, the application 130 can compare the physiological parameters 118 against a threshold to determine is an overdose event is occurring or will soon occur. For example, opioids depress the user's breathing. If the one or more of the oxygen saturation, breaths per minute, perfusion index and respiratory effort index indicate respiratory failure but being less that a threshold, the application may determine that an overdose event has occurred. The threshold can be a predetermined threshold that is adjusted as the application 130 learns the overdose triggers associated with the user. As the application 130 develops the trends, the application can refine the thresholds for one or more of the physiological parameters 118.

The application 130 can use the user's perfusion index to determine the likelihood of an overdose event. For example, opioids initially cause the perfusion index to increase due to vasodilation, then to decrease due to vasoconstriction. This can be an identifiable perfusion profile that anticipates an overdose event.

The application 130 can use one or more physiological parameters 118 to determine the condition of the user. The application 130 can use one or more of the perfusion index (PI), respiration, and peripheral oxygen saturation ($SpO_2$) to determine the condition of the user. For example, the application 130 can use, but is not limited to, each of the perfusion index (PI), respiration, and peripheral oxygen saturation ($SpO_2$) alone; a combination of the PI, respiration, and $SpO_2$ together; a combination of PI and respiration; a combination of PI and $SpO_2$; or a combination of respiration and $SpO_2$ to determine the condition of the user. The analysis of the physiological parameters 118 may show that the physiological parameters are within normal ranges and the user is not in need of assistance or the analysis may indicate that an overdose event is imminent, is occurring, or has occurred.

Other physiological parameters 118 can be analyzed individually or in other combinations can be analyzed to determine whether the physiological parameters 118 of the user are within normal ranges or whether an overdose event is imminent, is occurring, or has occurred.

The application 130 can query the user to determine the condition of the user. No response from the user can indicate that the user is unconscious and can trigger an overdose event notification or alarm. As indicated above, a response from the user can indicate that the user is conscious and the information can be used by the application 130 to refine the changes in the user's physiological parameters 118 that indicate an opioid overdose is occurring or will occur soon.

As described above, the mobile computing device 120 can include an accelerometer that can detect user motion. A lack of user motion sensed by the accelerometer can indicate that the user in unconscious and can trigger an overdose event notification or alarm. Motion sensed by the accelerometer can indicate that the user is conscious and the information can be used by the application 130 to refine the changes in the user's physiological parameters 118 that indicate an opioid overdose is occurring or will occur soon.

As described above, the mobile computing device 120 can include an accelerometer that can sense vibrations from the user indicative of the user's heart rate. A lack of vibrations sensed by the accelerometer can indicate no heart rate and reduced occurrences of vibrations sensed by the accelerometer can indicate cardiac distress, which can trigger an overdose event notification or alarm. Heart rate within normal parameters can indicate that the user is not in need of assistance due to an overdose event.

At block 230, the application 130 can determine whether care is useful based on the condition of the user. If care is indicated, such that the physiological parameters indicate depressed respiration, but not at a life-threatening level, the application moves to block 235. At block 235, the application 130 queries the user. If a response is received, the process 200 moves to the END block. A response indicates that the user is conscious and not in need if immediate aid.

If, at block 230, the application 130 determines that care is required because the evaluation of the physiological parameters 118 indicate a life-threatening condition, the process 200 moves to block 240. In addition, if no response is received from the user query at block 235, the process 200 moves to block 240.

Notifications

At block 240, the application 130 provides notifications based at least in part of the condition of the user. For example, the application 130 can display on the display 122 the user's physiological parameters, such as one or more of oxygen saturation, heart beats per minute, breaths-per-minute, pleth variability, perfusion index, and respiratory effort. The physiological parameters 118 can be displayed as charts, graphs, bar charts, numerical values, and the like. The application 130 can display trends in the physiological parameters 118.

The application 130 can provide notifications to selected friends indicating that there are no overdose conditions. The "everything is OK" notifications can be sent periodically or upon request. The "everything is OK" notifications can be sent during known exposure times. For example, the "everything is OK" notifications can be sent every 30 minutes from 6:00 PM when the user typically returns from work, to 11:00 PM when the user typically goes to sleep.

The application 130 can also report "near misses" to the caregiver. As described above, a "near miss" is an event that provided indications of an overdose, such as an indication of respiration below a threshold, but did not result in an overdose event.

Once the application 130 has determined that an overdose condition is imminent, is occurring, or has occurred, the application 130 can provide notification of the overdose to selected family, friends, caregivers, clinicians, and medical personnel. The notification can be sent to a crowd sourced community of users, friends, and medical personnel that look out for one another. The application 130 can provide the location of the user and/or directions to the user's location. The notification can include the location of the closest medical care and/or the location of the closest medication that reduces or reverses the effects of an overdose. Examples of such medications are, but not limited to, naloxone, buprenorphine, a combination of naloxone and buprenorphine, Narcan®, Suboxone®, Subutex®, and the like. The application 130 can indicate whether the overdose victim is conscious or unconscious.

The notification can include protocol for a first responder to render aid to the user. The application 130 can provide the user data to the medical personnel to aid them in administrating the correct dose of medication that reduces or reverses the effects of an overdose, such as naloxone and the like to the user. For example, if the overdose victim is also a heroin or marijuana user, the overdose victim may need a larger dosage of naloxone to reverse the effects of the opioid overdose than an overdose victim that does not also use heroin or marijuana. Further, the naloxone dosage may also need to be adjusted for the weight and age of the overdose victim. For example, a greater dosage on naloxone may be needed to reverse the depressed respiration effects of opioid overdose for an adult than is needed for a small child.

The application can provide trend data to medical personnel or to designated caregivers on a continual basis or may provide the trend data with the overdose notification. The dosage of medication to reduce or reverse the effects of the overdose, such as naloxone and the like, can be adjusted based at least in part on the trend data.

The application 130 can notify the user and request an acknowledgement for the user. For example, the application 130 can provide a visual notification on the display 122, and then cause the mobile computing device 120 to provide an audible notification, such as an audible alarm which can escalate to an increasing louder piercing sound in an attempt to wake up the user. The audible notification can include the name of the user. The application 130 can interact with a home system, such as Alexa®, Amazon Echo®, and the like, to create the alarm. The application 130 can cause the mobile computing device 120 or the home system, for example, to contact a live person who can provide immediate care instructions to the first responder.

The application 130 can provide the notifications to others in the user's community that have downloaded the application 130 on their mobile computing device. The application 130 can cause the mobile computing device 120 to send, for example, but not limited to text messages, emails, and phone calls to selected contacts in the user's mobile device 120, who may or may not have downloaded the application 130 to their mobile computing device 120. The mobile computing device 120 can automatically dial 911 or other emergency response numbers. The application 130 can transmit the location of the user to one or more selected ambulances and paramedics.

FIGS. 3A-3E illustrate various example software applications to provide information, notifications, and alerts to opioid users, first responders, medical personnel, and friends.

Figure 3A:
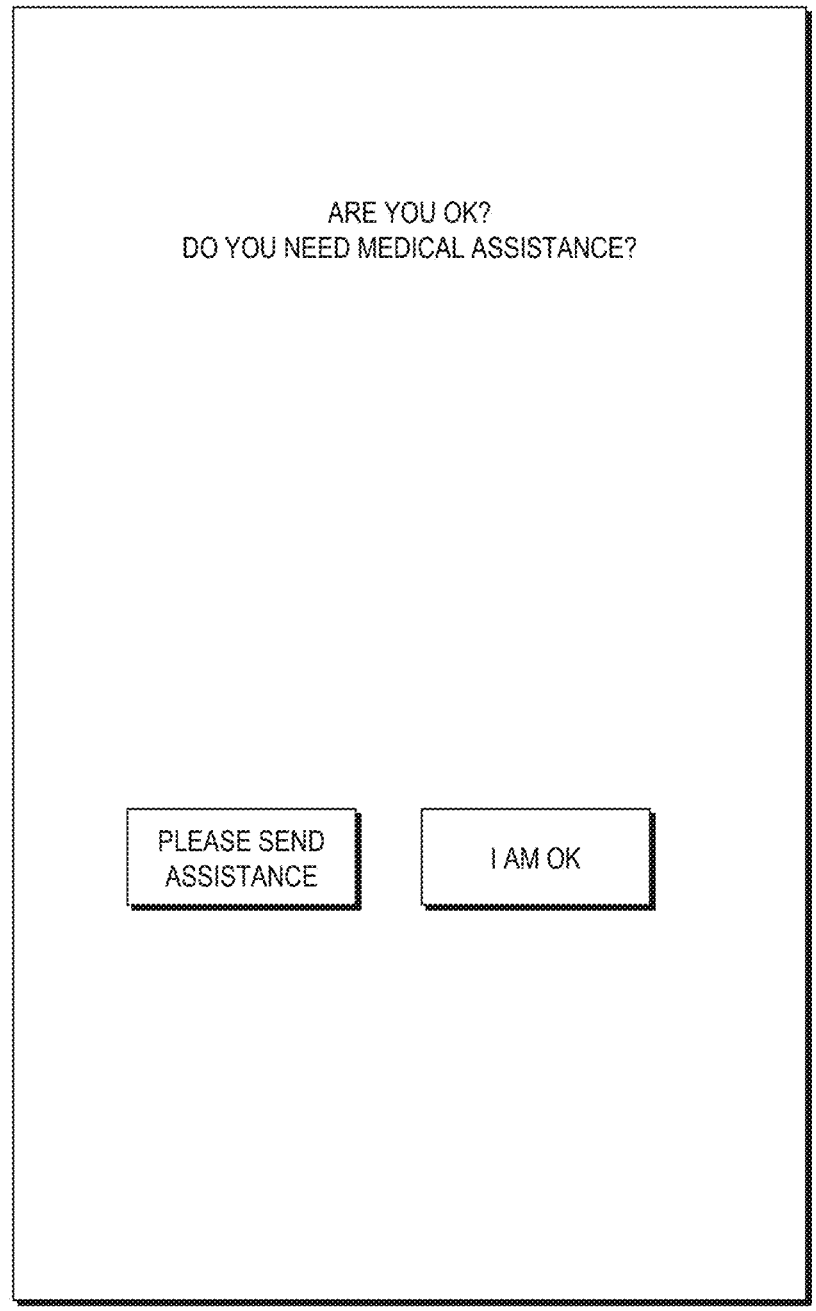

FIG. 3A is a screenshot 300 illustrating a request for user input. The illustrated screenshot 300 displays a question "ARE YOU OK? DO YOU NEED MEDICAL ASSISTANCE?" and selections for the user's response. If no response is received, the user may be assumed to be unconscious. If a response is received, the application 130 can use the physiological parameters 118 associated with the response to refine the algorithm to determine an overdose event for the specific user. The refinements can include refinements to the overdose threshold for the physiological parameters 118 or can include refinements to the parameter trends associated with an overdose event.

Figure 3B:
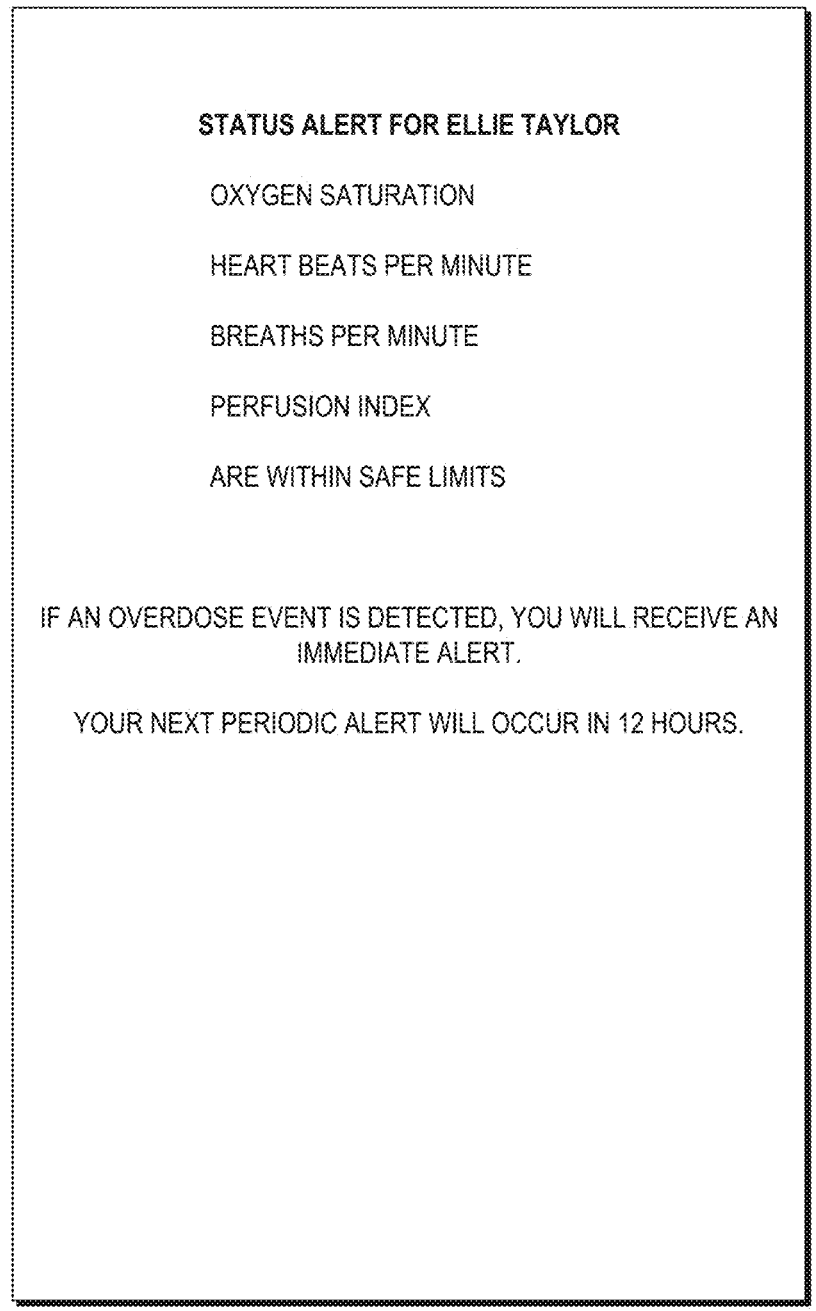

FIG. 3B is a screenshot 310 illustrating a periodic status alert that can be send via text message or email to friends or family that have set up periodic well checks for the user in the user's application 130. The illustrated screenshot 310 also indicates when the next well check will occur.

Figure 3C:
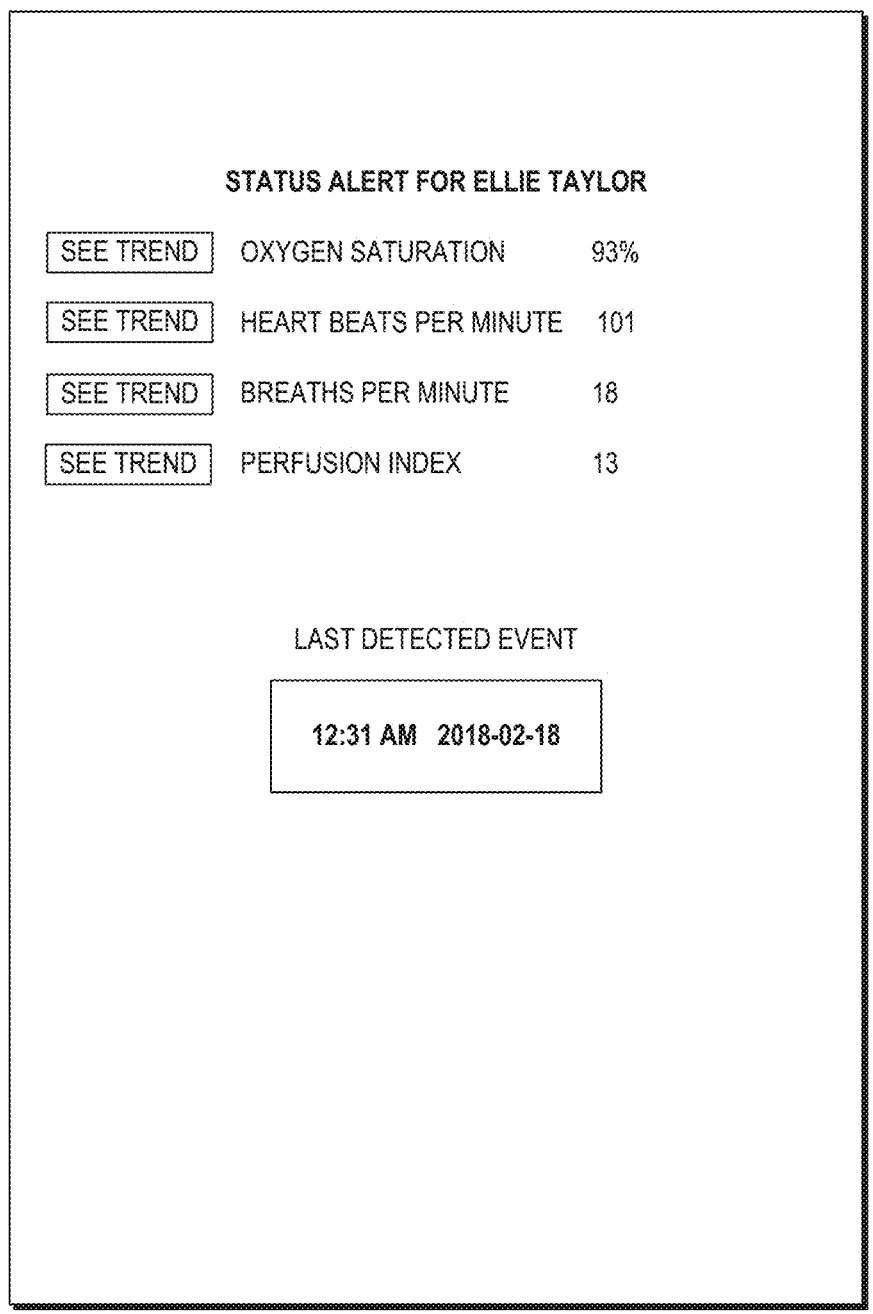

FIG. 3C is a screenshot 320 illustrating a status alert that can be send via text message or email to friends or family that have set up periodic well checks for the user in the user's application 130. The illustrated screenshot 320 indicates current values for monitored physiological parameters and provides a section SEE TRENDS to view the trend data for the physiological parameters. The illustrated screenshot 320 also indicates the date and time of the most recent overdose event.

FIG. 3D is a screenshot 330 illustrating first responder protocols. The illustrated screenshot 330 displays resuscitation information for the person(s) responding to the overdose notification.

Figure 3E:
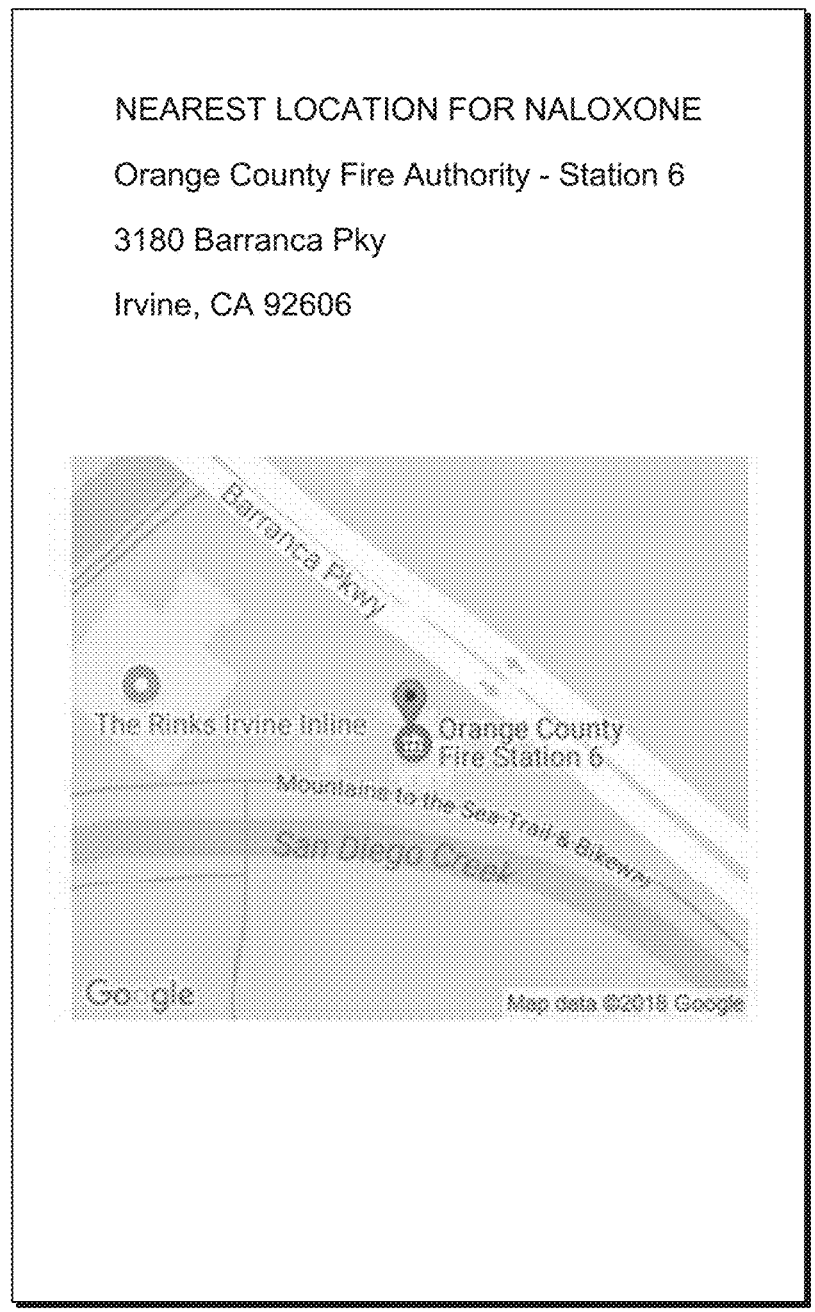

FIG. 3E a screenshot 340 illustrating the nearest location to the user that has available naloxone. The illustrated screenshot 340 displays an address and a map of the location.

Notify a Friend

Figure 4:
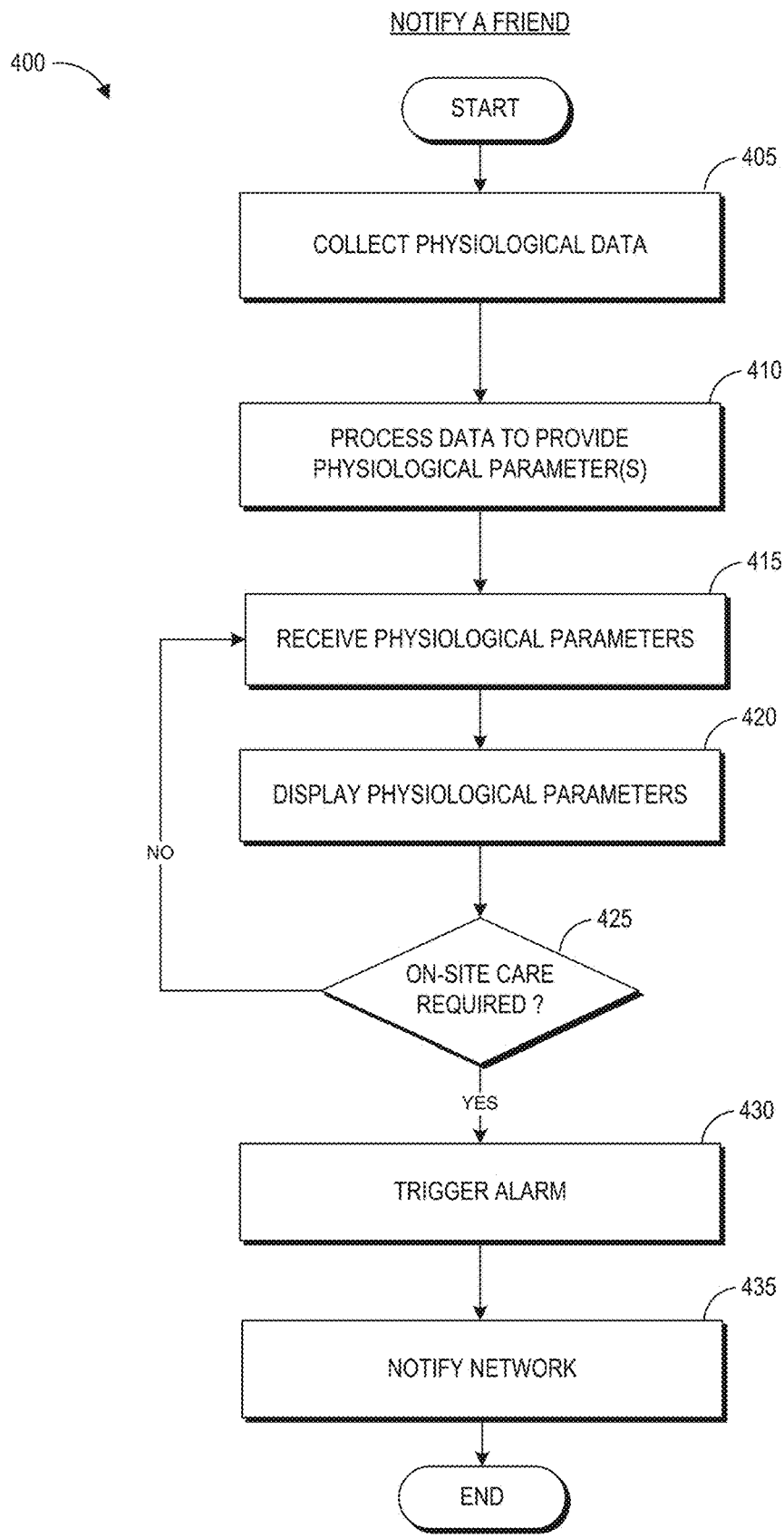
FIG. 4 is a flow chart of an example process to monitor for opioid overdose.

FIG. 4 illustrates an example process 400 to monitor for opioid overdose using the mobile physiological parameter monitoring system 100 including the sensor 102 and the signal processing device 110, and the mobile computing device 120. The user or the caregiver downloads the application 130 into the mobile computing device 120. The user or caregiver can select a person or persons to be notified by the mobile computing device 120 when the application 130 determines an opioid overdose event is occurring. The mobile computing device 120 can comprise a mobile communication device, such as a smartphone. The user attaches the sensor 102 to a body part, such as clipping the sensor 102 onto a finger, a toe, the forehead, for example, and connects either wirelessly or via a cable to the mobile computing device 120 that includes the application 130.

At block 405, the mobile physiological parameter monitoring system 100 collects raw data 104 from the sensor 102. At block 410, signal processing device 110 processes the raw data and provides the mobile computing device 120 with physiological parameters 118.

At block 415, the mobile computing device 120 receives the physiological parameters 118 from the physiological parameter monitoring device 110.

At block 420, the application 130 displays on the display 122 of the mobile computing device 120 the physiological parameters 118. The mobile computing device 120 can display numerical indications, graphs, pie charts, dials, and the like. The displays can include acceptable and unacceptable ranges for the physiological parameters 118. The display can be color coded. For example, acceptable ranges can be colored green and unacceptable ranges can be colored red. The application 130 can display on the mobile computing device 120 the physiological parameters 118 as the physiological parameters 118 are received (in real time) or at approximately the same time (near real time) as the physiological parameters 118 are received.

At block 425, the application 130 can monitor the physiological parameters 118 for indications of an opioid overdose. The monitored physiological parameters 118 can include the physiological parameters that are most likely affected by an overdose condition. The physiological parameters 118 can be one or more of the oxygen saturation, heart rate, respiration rate, pleth variability, perfusion index, and the like of the user.

The application 130 can determine whether the physiological parameters 118 indicate that the user needs on-site care. A blood oxygen saturation level below a threshold can indicate an opioid overdose condition. For example, the application 130 can monitor the oxygen saturation of the user and trigger an alarm when the oxygen saturation falls below a threshold. The application 130 can compare the user's current oxygen saturation level with a threshold that can indicate a minimum acceptable blood oxygen saturation level. An oxygen saturation level below the minimum acceptable blood oxygen saturation level can be an indication of an overdose event. For example, an oxygen saturation level below approximately 88 can indicate respiratory distress.

The application 130 can compare each of the monitored physiological parameters 118 with a threshold that indicates a minimum or maximum acceptable level for the physiological parameter 118. For example, the application 130 can compare the user's heart rate in beats per minute with the acceptable range of approximately 50 beats per minute to approximately 195 beats per minute. The application 130 can compare the user's respiration rate in breaths per minute with the acceptable range of approximately 6 breaths per minute to approximately 30 breaths per minute. The application 130 can compare the user's pleth the acceptable range of approximately 5 to approximately 40 and the user's perfusion index to a minimum acceptable perfusion index of approximately 0.3.

One or more physiological parameters 118 can be weighted and when the combination of weighted parameters falls below a threshold, the application 130 can trigger the notification of an opioid overdose event. One or more physiological parameters 118 can be weighted based on trends in the user's physiological parameters during opioid use and when the combination of weighted parameters falls below a threshold, the application 130 can trigger the notification of an opioid overdose event.

When the measured physiological parameters 118 are within acceptable ranges, the process 400 can return to block 415 and the mobile computing device 120 can continue to receive the physiological parameters 118 from the sensor 102 via the physiological parameter monitoring device 110. The application 130 can compare one, more than one, or all of the measured physiological parameters 118 to determine an overdose event.

When an overdose is indicated as imminent or occurring, the process 400 moves to block 430. For example, when the user's blood oxygen saturation level is at or below the threshold, the application 130 triggers an alarm at block 430. When at least one of the monitored parameters 118 is below an acceptable threshold, the process 400 can trigger an alarm. The alarm can be an audible alarm that increases in loudness, frequency, or pitch. The alarm can be the user's name, a vibration, or a combination of audible sound, vibration, and name.

The mobile computing device 120 can vibrate, audibly alarm, display a warning, visibly flash, and the like to notify the user or someone at the same physical location as the mobile computing device 120 to the overdose event. The alarm can be an audible alarm that increases in loudness, frequency, or pitch. The alarm can be the user's name, a vibration, or a combination of audible sound, vibration, and name.

The mobile computing device 120 can display the location of and/or direction to naloxone or other medication to reverse or reduce the effects of an overdose closest to the user. The mobile computing device 120 can display the phone number of the person associated with the closest medication to reverse or reduce the effects of an overdose, such as naloxone. The mobile computing device 120 can display resuscitation instructions to the first responder. The mobile computing device 120 can request an acknowledgement from the first responder. The mobile computing device 120 can display the resuscitation instructions to the first responder, call medical personnel, and facilitate questions and answers between the first responder and the medical personnel.

If the user is alone, this may not be enough to avoid a life-threatening overdose condition. At block 435, the application 130 can send a notification to the user's network, such as the person(s), emergency personnel, friends, family, caregivers, doctors, hospitals selected to be notified. The notification can be sent in conjunction with the network connectivity 128 of the user's mobile computing device 120. The notification informs the selected person(s) of the user's opioid overdose. For example, the selected person(s) can receive a notification on their mobile computing device. The selected person(s) can be a friend, a group of friends, first responders, medical personnel, and the like. The mobile computing device 120 can automatically dial 911 or other emergency response numbers.

The notification can be sent to a crowd sourced community of opioid users that look out for one another, such as a community of individuals and/or organizations associated with one or more opioid users. The community functions to provide help to opioid users and can includes not only other opioid users, but friends, family, sponsors, first responders, medics, clinicians, and anyone with access to medication to reverse or reduce the effects of an overdose, such as naloxone.

The notification can be one or more of text message, an automatically dialed phone call, an email, or the like. The notification can include one or more of a graphical representation, a numerical value or the like of the user's unacceptable or out-of-acceptable-range physiological parameter 118, the time of the overdose, the location of the user, directions to the location, and the phone number of the user's mobile computing device 120. The notification can also provide the location of and/or direction to medication to reverse or reduce the effects of an overdose, such as naloxone, closest to the user, as well as the phone number of the person associated with the closest medication to reverse or reduce the effects of an overdose, such as naloxone.

FIGS. 5A-5F illustrate various example software applications to trigger an alarm and notify a friend when an opioid overdoes is indicated.

Figure 5A:
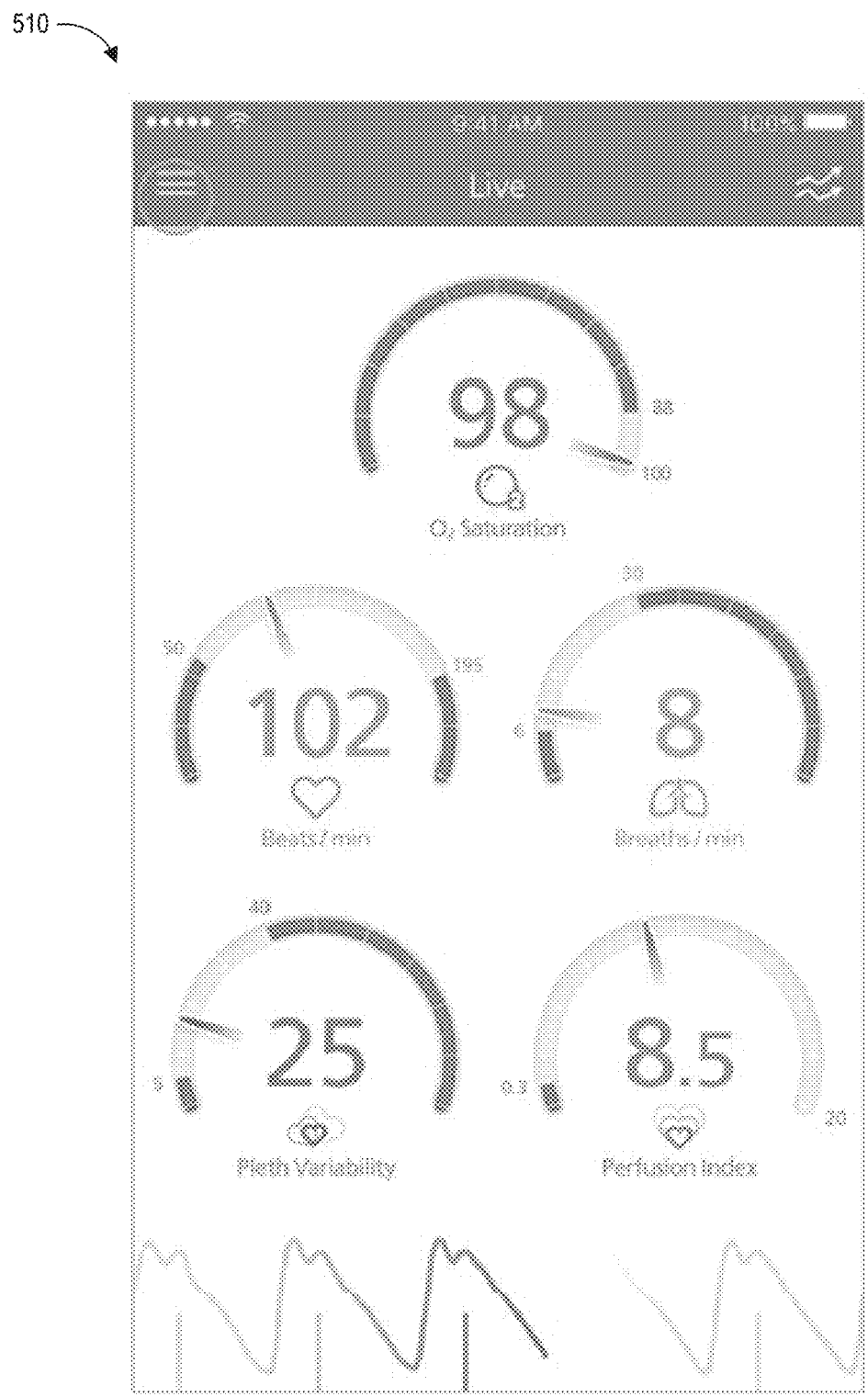
FIGS. 5A-5F illustrate various example software applications to trigger an alarm and notify a friend when an opioid overdose is indicated.

FIG. 5A is an example screenshot 510 illustrating active monitoring of physiological parameters 118. The illustrated monitoring screenshot 510 displays the user's oxygen saturation, heart rate as beats per minute, respiration rate as breaths per minute, pleth variability and perfusion index. The physiological parameters 118 are represented as dials. The dials indicate a normal range and unacceptable ranges that can be above, below or both above and below the normal range. A needle within the dial points to the current value of the physiological parameter and a numerical indication of the current value is displayed in the center of the dial.

Figure 5B:
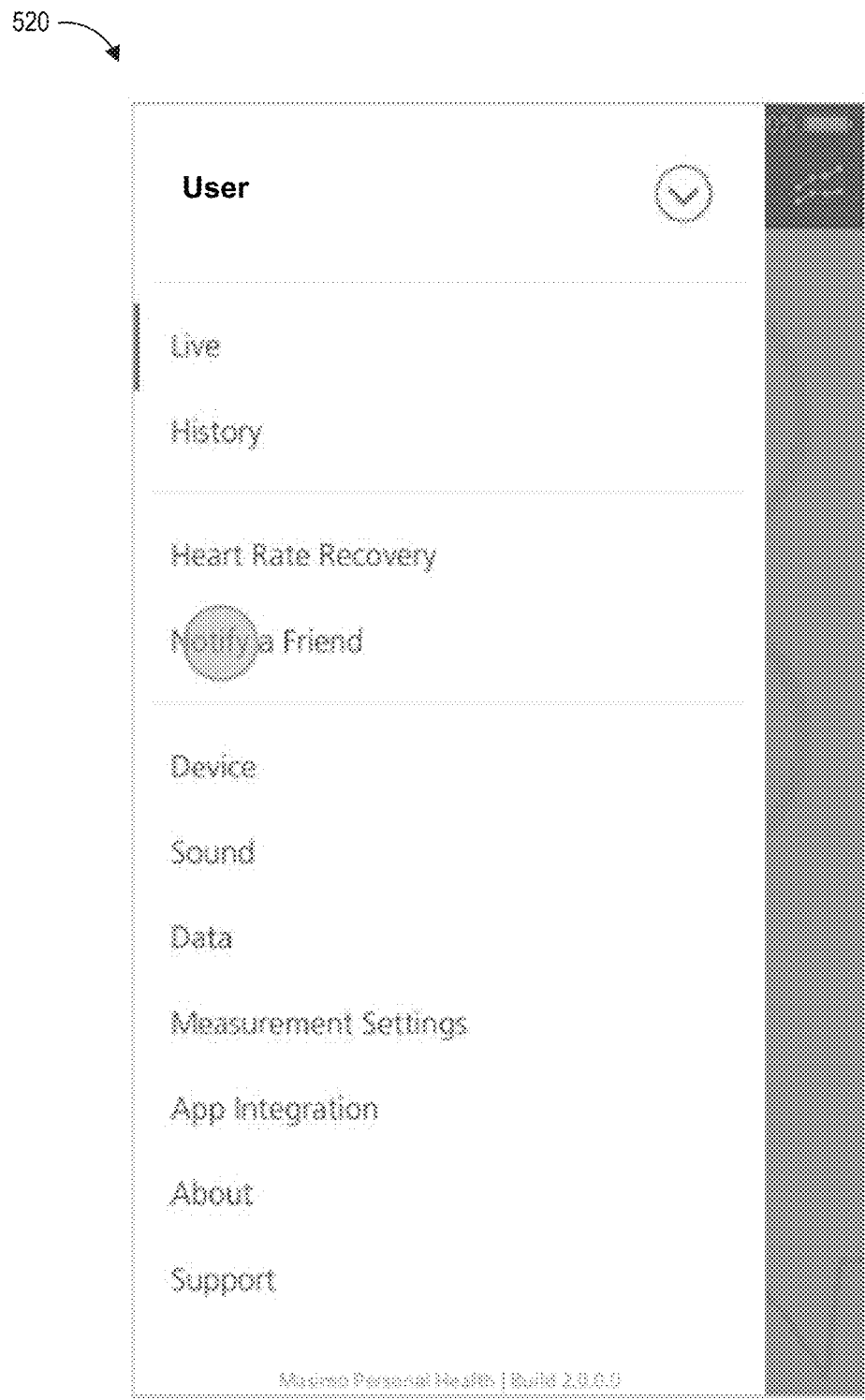

FIG. 5B is an example screenshot 520 illustrating a home screen with the main menu. The illustrated home screen 520 includes a selection LIVE to display physiological parameters being monitored in real time or near real time, such as shown on the monitoring screenshot 510. The home screen 520 further includes a selection for HISTORY, HEART RATE RECOVERY, and NOTIFY A FRIEND.

Selecting HISTORY can display the past physiological parameters stored in storage 124 as one or more of graphs, charts, bar graphs, and the like. The application 130 can use the HISTORY to develop trends for the specific opioid user to more accurately determine when an opioid overdose event is imminent.

Heart rate is the speed of the heartbeat measured by the number of contractions of the heart per minute (bpm). The heart rate can vary according to the body's physical needs, including the need to absorb oxygen and excrete carbon dioxide. Selecting HEART RATE RECOVERY can display the recovery heart rate of the user after a near opioid overdose or overdose event.

Selecting NOTIFY A FRIEND allows the user or a caregiver to select a contact from the mobile computing device 120 to be notified in the event that the user's physiological parameters 118 indicate that the user is experiencing or will soon experience an overdose event.

The home screen 530 further includes a setup section that includes DEVICE, SOUND, DATA, MEASUREMENT SETTINGS, APP INTEGRATION, ABOUT, AND SUPPORT. The user can receive information, such as device data, for example, or select setting, such as what measurements are displayed, change alarm volume, and the like.

Figure 5C:
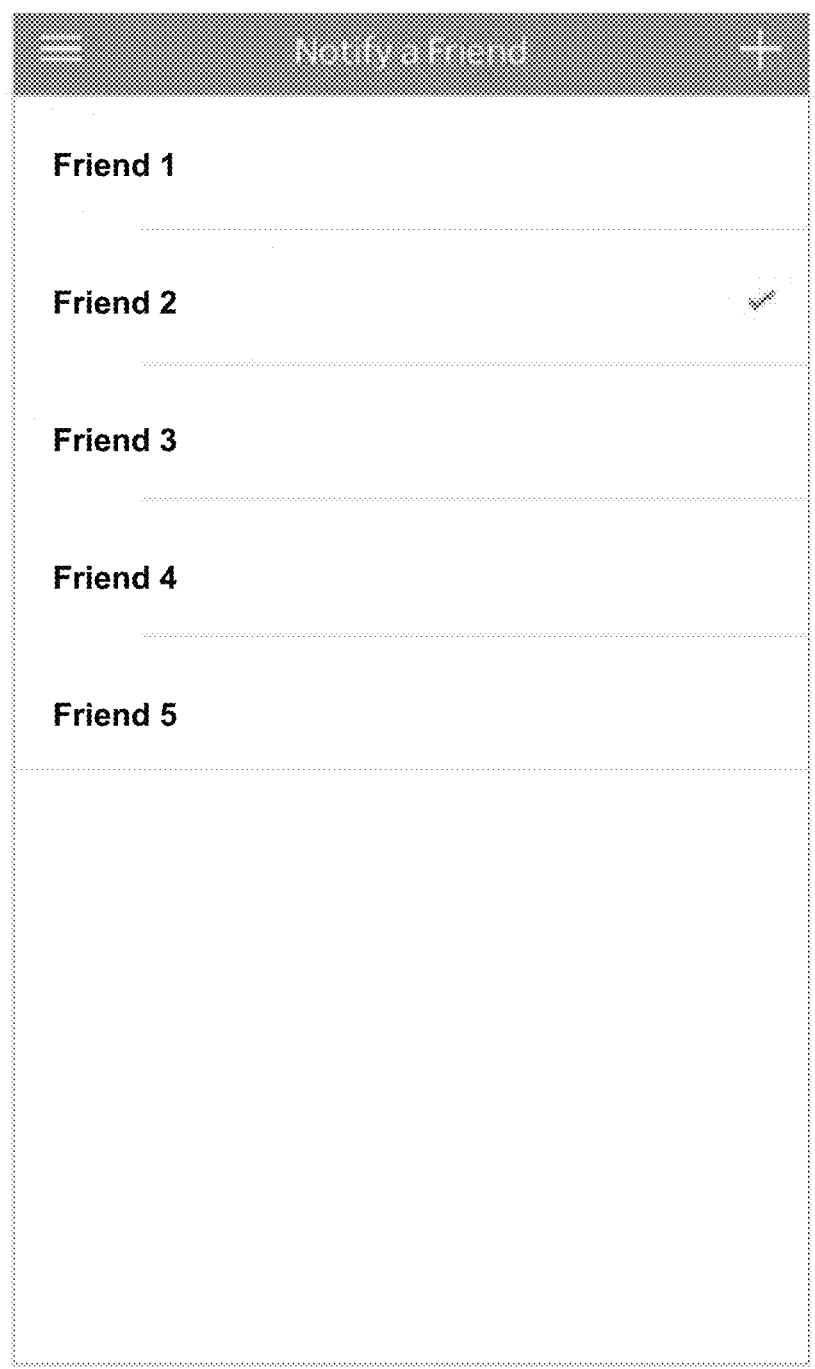

FIG. 5C is an example screenshot 530 illustrating the NOTIFY A FRIEND screen. The illustrated NOTIFY A FRIEND screen 530 allows the user or caregiver to select a person from the contacts stored on the mobile computing device 120 to be contacted when an overdose event occurs. In the illustrated NOTIFY A FRIEND screen 530, the second person on the contact list has been selected.

Figure 5D:
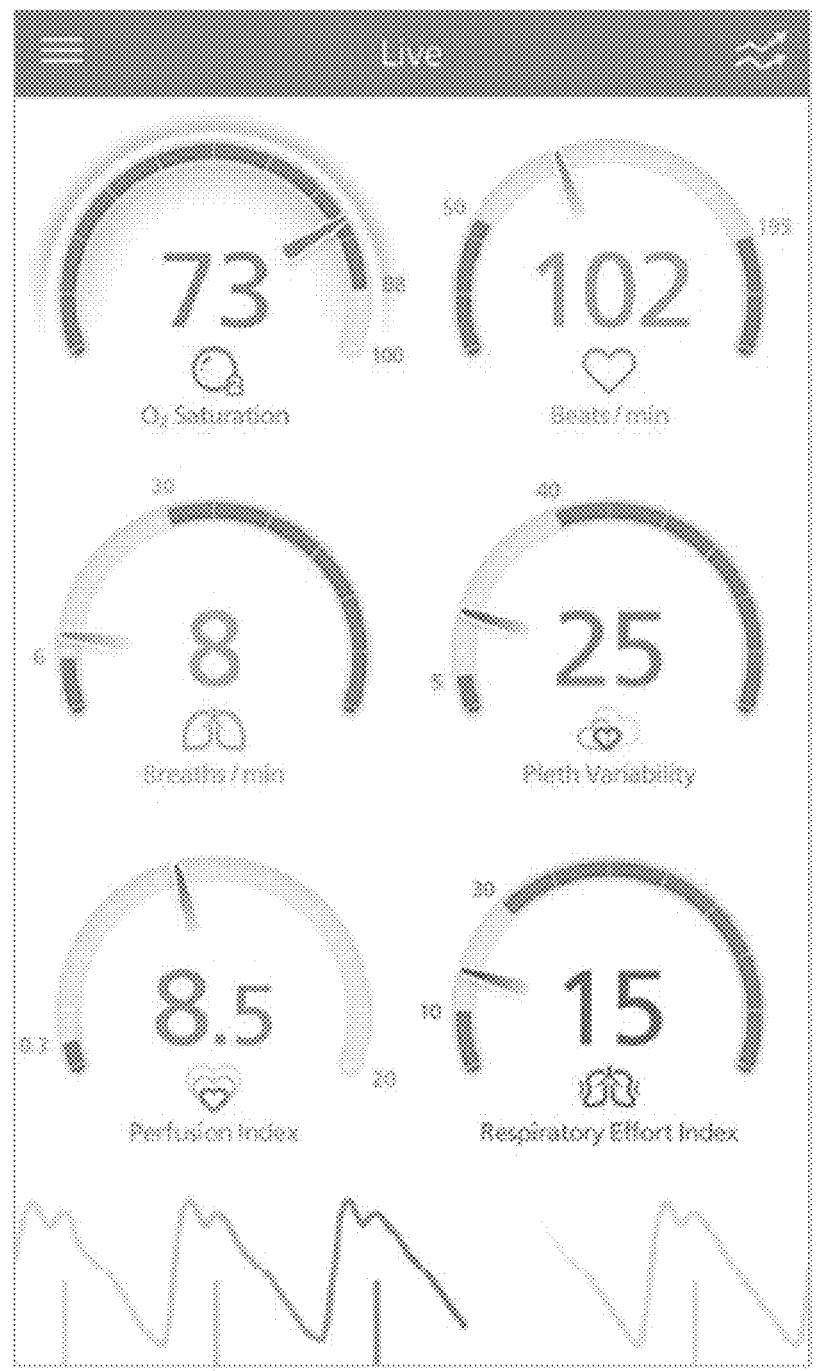

FIG. 5D is an example screenshot 540 illustrating live or active monitoring of the user having an alarm condition. The illustrated parameter monitoring screen 540 shows that the user's oxygen saturation level has dropped below an acceptable threshold of 88 to a value of 73. This indicates an overdose event may be occurring. The user's heart rate, respiration rate, pleth variability and perfusion index have not changed from the values displayed on the live monitoring screen 510.

FIG. 5D also includes a RESPIRATORY EFFORT INDEX, which provide an indication of whether breathing is occurring or is suppressed.

Figure 5E:
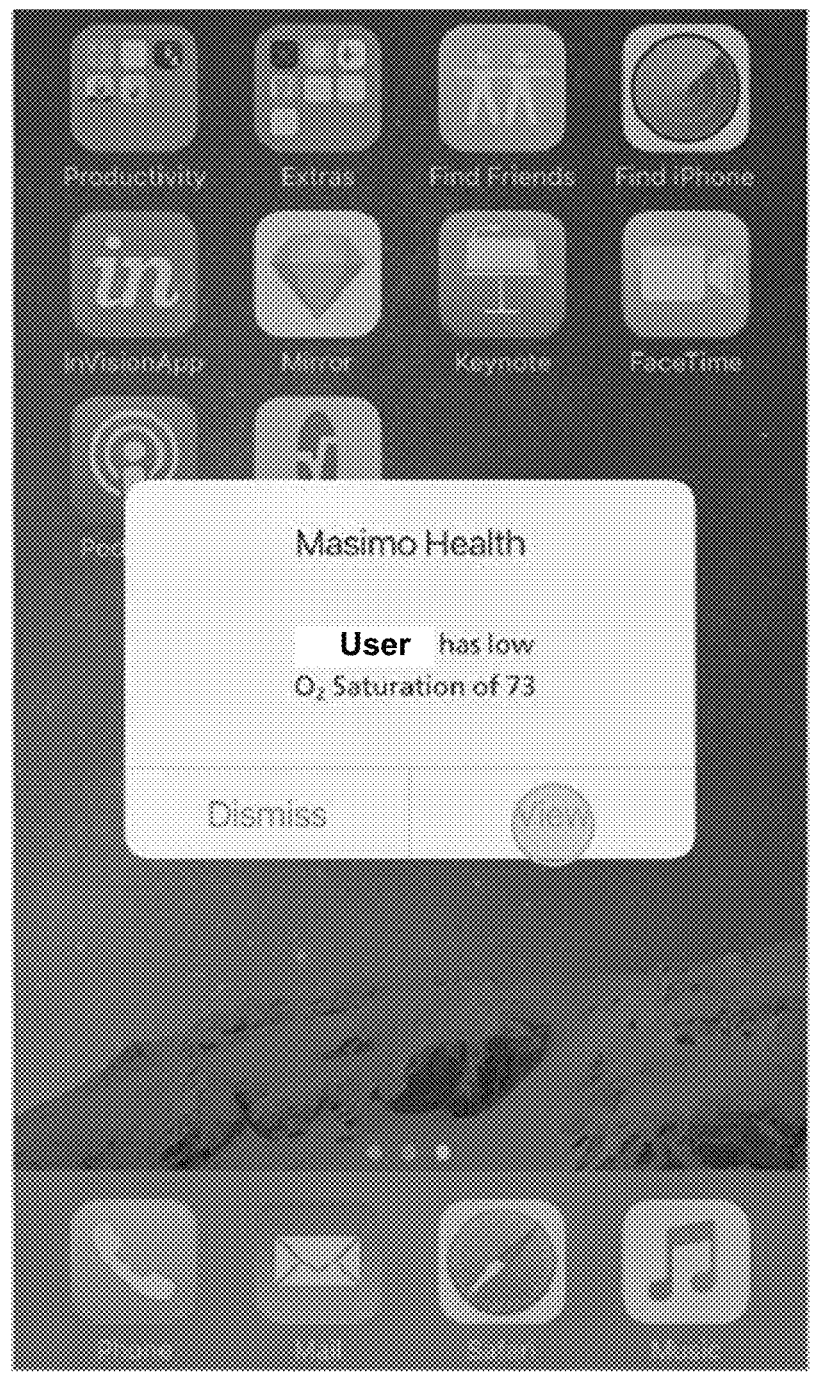

FIG. 5E is an example screenshot 550 illustrating a notification screen sent to the friend/selected contact to notify the friend of the user's overdose event. Once the alarm is triggered on the user's mobile computing device 120, the selected person is notified of the alarm status. The notification screen 550 can display the user's name and the alarm condition. The illustrated notification screen 550 informs the friend that Ellie Taylor has low oxygen saturation of 73. Selecting or touching the VIEW selection provides additional information.

Figure 5F:
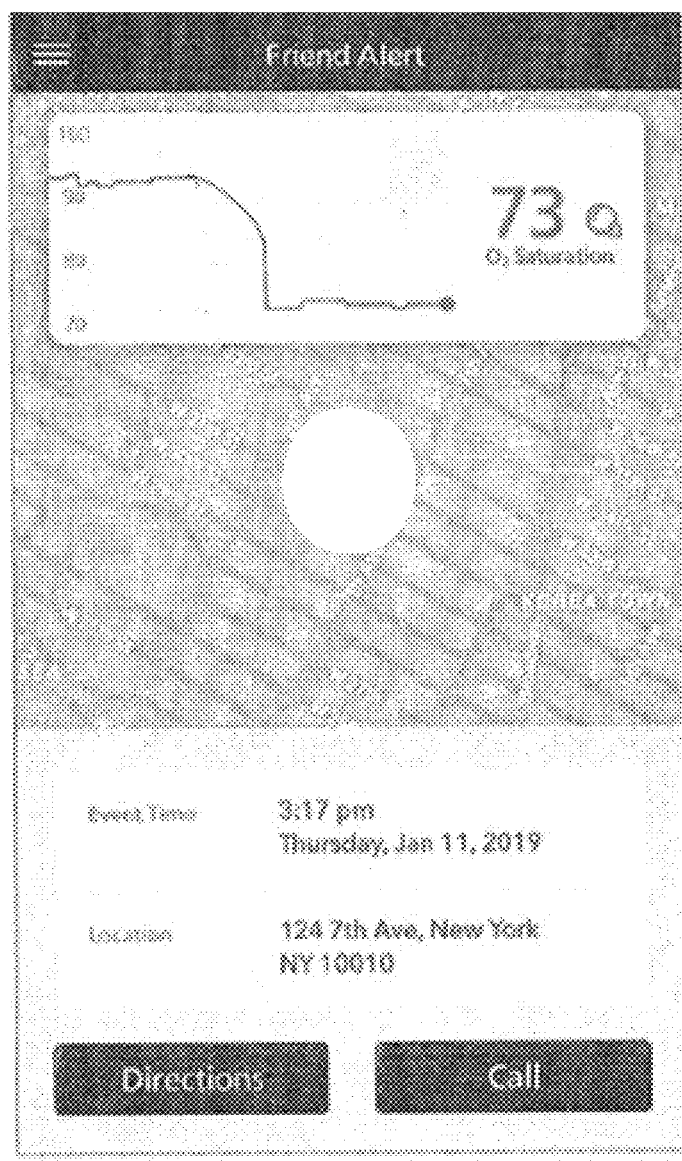

FIG. 5F is an example screenshot 560 illustrating the friend alert including additional information provided to the selected person. The friend alert screen 560 can include the trend and current value of the alarming parameter. For example, the illustrated friend alert screen 560 displays the graph and current value of the user's oxygen saturation. The friend alert screen 560 can also display the user's location on a map, display the time of the initial alarm event, provide access to directions to the user from the friend's current location in one touch, and provide access to call the user in one touch. The friend has the knowledge that the user is overdosing and the information to provide help.

Assistance for Responders and Caregivers

It is critical to administer an opioid receptor antagonist, such as Naloxone, to victims of opioid overdoses as soon as possible. Often it can be a matter of life or death for the overdose victim. As described herein, self-administrating delivery devices can administer the opioid receptor antagonist without user or responder action. Opioid overdose victims without a self-administrating delivery device rely on the responders, friends, or caregivers that are first on the scene to administer the opioid receptor antagonist. Assistance that can be provided to the first responders can be useful and the assistance can take many forms. The assistance can be visual or auditory indicators and/or instructions. The user can wear a band, such as a wrist band, for example, that changes color to indicate an opioid overdose event. A display, such as a display on a mobile device, can change color, or flash to draw attention when an opioid overdose event is detected. The mobile or other device can transmit a notification or transmit the flashing display to other devices within range to notify others of the opioid overdose event. The display can display instructions that explain how to administer the opioid receptor antagonist, such as Naloxone. The display can display instructions to wake the overdose victim using smelling salts, shaking, escalation of painful stimulation, loud noises, or any combination of these. The responder can be instructed to incrementally increase aggressive actions to wake the overdose victim. An example of incrementally increasing aggressive action can be loud sound, followed by a small amount of painful stimulation, followed by administration of a small amount of Naloxone or other opioid receptor antagonist, followed by an increased amount of painful stimulation. The first responder can be instructed to induce pain using acupuncture. The mobile or other device can speak the instructions to get the attention of others that are nearby. The mobile or other device can speak "Please inject Naloxone" to indicate urgency. The mobile or other device can beep to attract attention. The mobile or other device can buzz and/or provide voice directions to help in directionally finding the overdose victim.

The mobile or other device can provide codes to emergency personnel within proximity. The mobile or other device can send a signal to emergency personnel or police indicating that the Naloxone needs to be delivered as soon as possible.

The first responder can also administer medication to induce vomiting once the overdose victim is awake and upright. The user may regurgitate any opioid substances, such as pills, for example, that are still in the user's stomach.

Network Environment

Figure 7A:
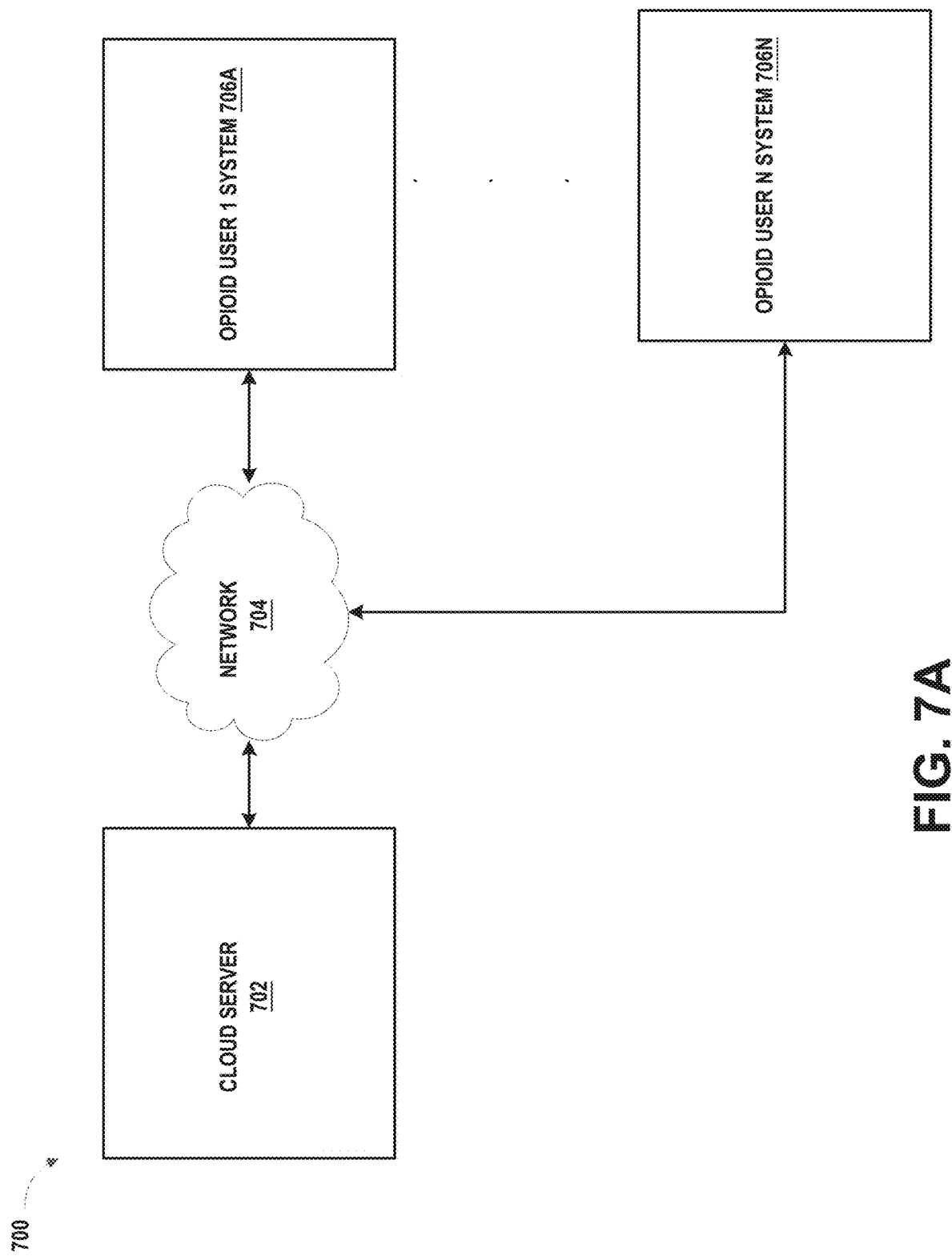
FIG. 7A is a block diagram of an example opioid user system environment and an example cloud environment.

FIG. 7A illustrates an example network environment 700 in which a plurality of opioid user systems 706, shown as opioid user systems 706A . . . 706N, communicate with a cloud environment 702 via network 704. The components of the opioid user systems 706 are described in greater detail with respect to FIG. 7C.

The network 704 may be any wired network, wireless network, or combination thereof. In addition, the network 704 may be a personal area network, local area network, wide area network, over-the-air broadcast network (e.g., for radio or television), cable network, satellite network, cellular telephone network, or combination thereof. For example, the network 704 may be a publicly accessible network of linked networks such as the Internet. Protocols and components for communicating via the Internet or any of the other aforementioned types of communication networks are well known to those skilled in the art and, thus, are not described in more detail herein.

For example, the opioid user systems 706A . . . 706N and the cloud environment 702 may each be implemented on one or more wired and/or wireless private networks, and the network 704 may be a public network (e.g., the Internet) via which the opioid user systems 706A . . . 706N and the cloud environment 702 communicate with each other. The cloud environment 702 may be a cloud-based platform configured to communicate with multiple opioid user systems 706A . . . 706N. The cloud environment 702 may include a collection of services, which are delivered via the network 704 as web services. The components of the cloud environment 702 are described in greater detail below with reference to FIG. 7B.

Figure 7B:
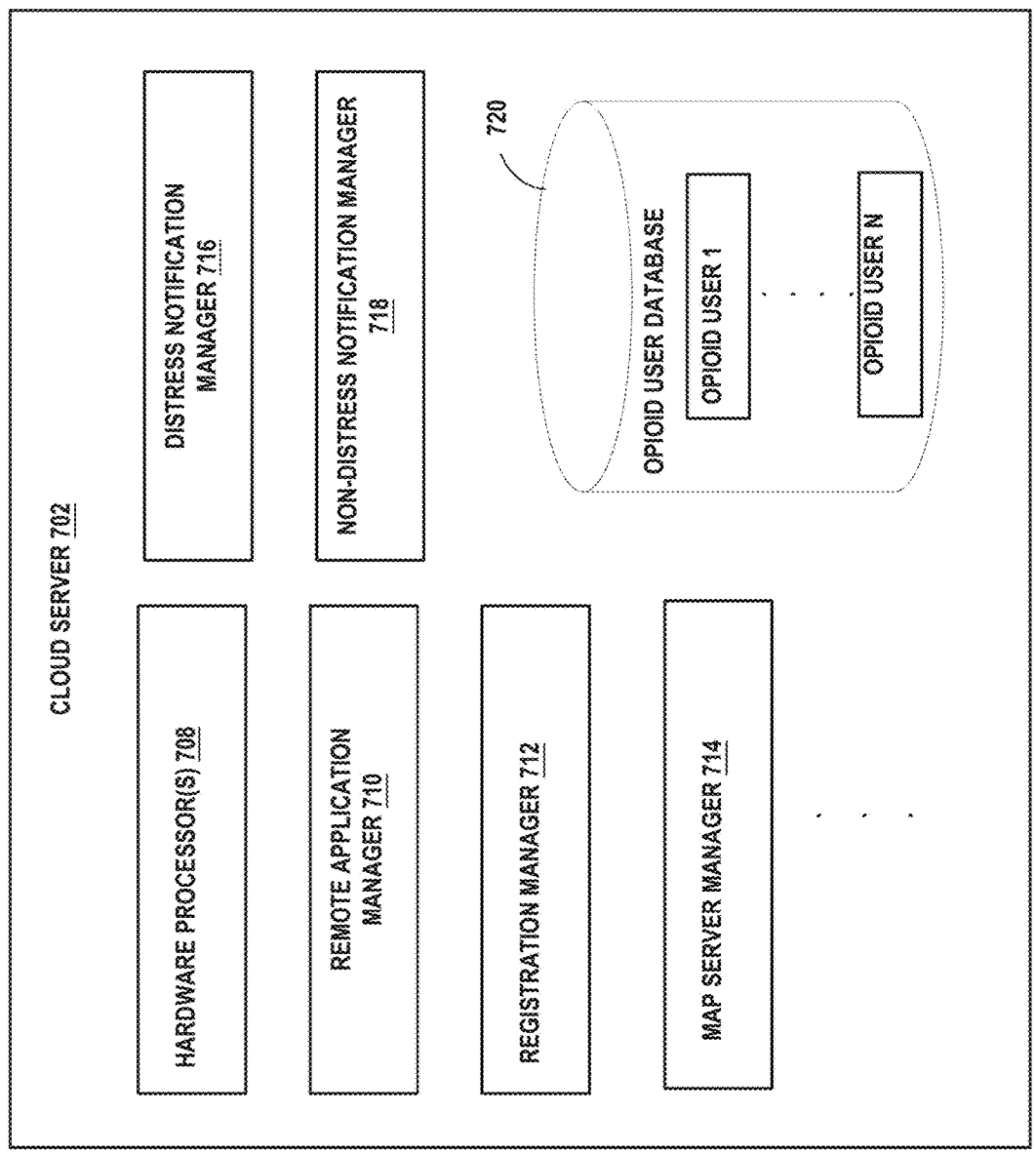
FIG. 7B is a block diagram illustrating example components of a cloud environment.

FIG. 7B illustrates an example of an architecture of an illustrative server for opioid user monitoring. The general architecture of the cloud environment 702 depicted in FIG. 7B includes an arrangement of computer hardware and software components that may be used to implement examples of the present disclosure. As illustrated the cloud environment 702 includes one or more hardware processors 708, a remote application manager 710, a registration manager 712, a map server manager 714, a distress notification manager 716, a non-distress manager 718, and an opioid user database 720, all of which may communicate with one another by way of a communication bus. Components of the cloud environment 702 may be physical hardware components or implemented in a virtualized environment. The remote application manager 710, the registration manager 712, the map server manager 714, the distress notification manager 716, and the non-distress 718 manager may include computer instructions that the one or more hardware processors execute in order to implement one or more example processes. The cloud environment 702 may include more or fewer components than those shown in FIG. 7B.

The remote application manager 710 may oversee the monitoring and notifications of associated with the plurality of opioid user systems 706A . . . 706N. The remote application manager 710 is remote in the sense that it is located in a centralized environment as opposed to each opioid user's local environment. The remote application manager 710 may oversee the registration manager 712, the map server manager 714, the distress notification manager 716, and the non-distress notification manager 718. The remote application manager 710 may perform one or more of the steps of FIG. 2B, 4.

The registration manager 712 may manage the information associated with each opioid user registrant and the contact information supplied by each opioid user registrant during registration for the opioid overdose monitoring system. The contact information may include the names, phone number, email addresses, etc. of individuals and/or organizations to contact on behalf of the opioid user when an overdose event is predicted or detected, or for status check information, as well as the name, address, phone number, email address, etc. of the opioid user registrant. Examples of individuals and organizations are illustrated in FIG. 1B. The opioid user information and the contact information associated with each opioid user registrant may be stored in database 720. FIGS. 5B, 5C illustrate examples of interface screens that may be used during registration.

The map server manager 714 may locate maps and directions, such as those illustrated in FIGS. 3E and 5F to display on devices associated with first responders, friend and family, and other individuals from the opioid user's contact information to display maps or directions to the opioid user, to the location of the closest naloxone or other such medication to the opioid user, and the like, in the event of an overdose. FIGS. 5E, 5F illustrate examples of distress notifications. The map server manager 714 may interface with third party map sites via the network 704 to provide the maps and directions.

The distress notification manager may receive an alert from the opioid user's mobile device that an overdose event may soon occur or has occurred. For example, the mobile device 120 or the monitoring device 110 may process the sensor data from the sensors 102 and determine that an overdose event is occurring. The mobile device 120 may communication the occurrence of overdose event with the distress notification manager 716. The distress notification manager 716 may retrieve contact information from the database 720 and provide notification of the overdose event or a soon to occur overdose event to the individuals and organizations indicated by the opioid user during registration so that assistance can be provided to the opioid user. FIG. 5F illustrates an example of a distress notification.

The non-distress notification manager 714 may receive the status of the opioid user as monitored by the mobile device 120 and/or the monitoring device 110. The non-distress notification manager 718 may receive the status periodically. After determining that the status of the opioid user indicates that the opioid user is not in distress, the non-distress notification manager may access the database 720 to retrieve the contact information for the individual and organizations that are to be notified of the well-being of the opioid user. FIGS. 3B, 3C, 5D illustrate examples of non-distress notifications.

Figure 7C:
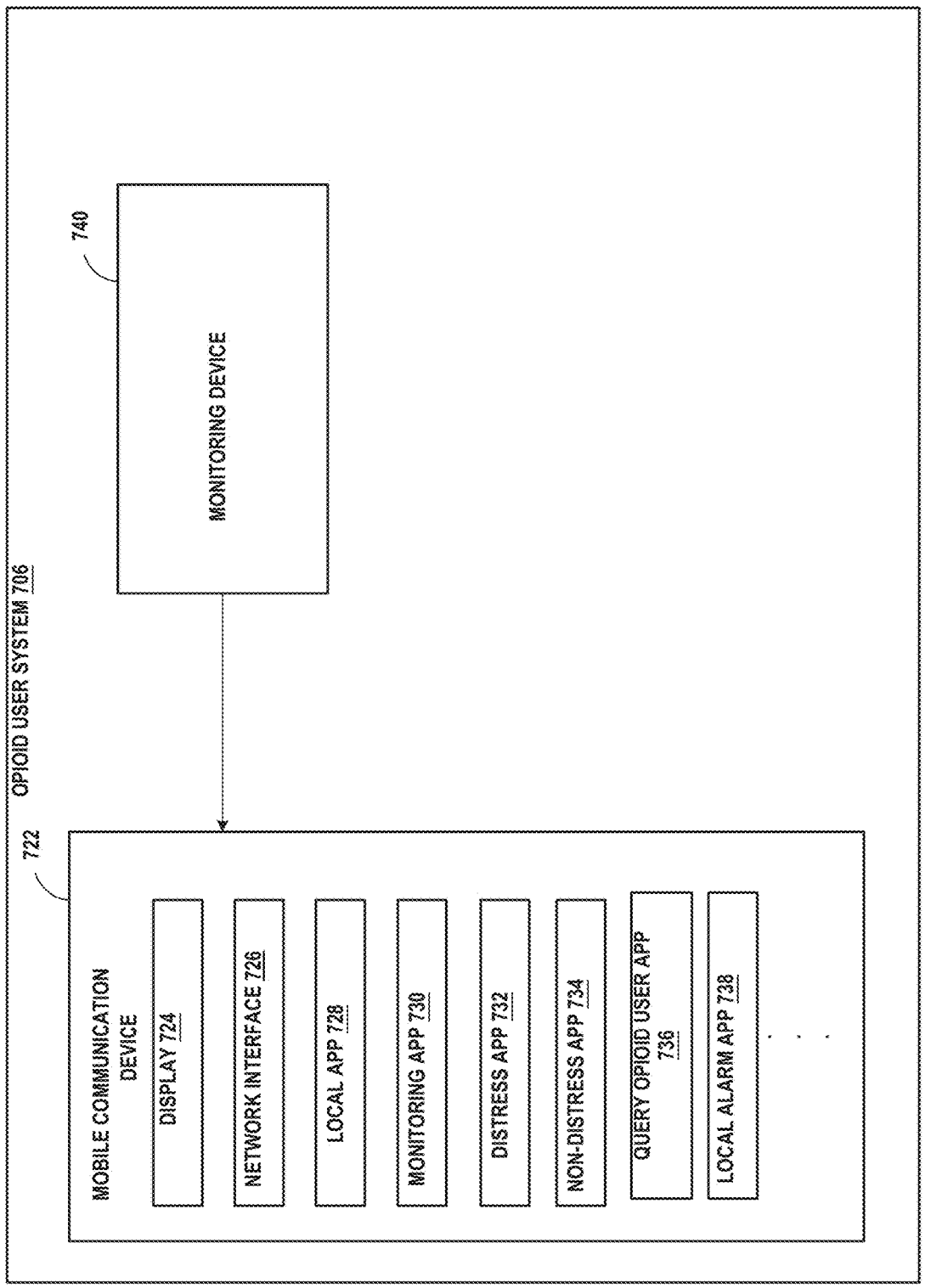
FIG. 7C is a block diagram illustrating example components of an opioid user system of an example opioid user system environment.

FIG. 7C illustrates an example opioid user system 706, which includes the monitoring device 740 and the mobile communication device 722. The monitoring device can include the sensor(s) 120 that are sensing physiological state of the opioid user and the signal processing device 110 that is processing the raw sensor data from the sensor(s) 110 to provide the mobile communication device 722 with the physiological parameters 118. The raw sensor data 104 from the sensor(s) 102 can be input into the mobile communication device 722, which processes the raw sensor data 104 to provide the physiological parameters 118 of the opioid user.

The illustrated mobile communication device 722 includes a display 724, similar to display 122, described herein, a network interface 726 that is configured to communication at least with the cloud environment 702 via the network 704, a local application 728, a monitoring application 730, a distress application 732, a non-distress application 734, a query opioid user application 736, and a local alarm application 738. The local application 728, the monitoring application 730, the distress application 732, the non-distress application 734, the query opioid user application 736, and the local alarm application 738 may be software instructions stored in memory within the mobile communication device 722 that are executed by the computing devices within the mobile communication device 722. The applications 728-738 can be downloaded onto the mobile communication device 722 from a third party or from the cloud environment 702. The mobile communication device 722 may include more or fewer components than those illustrated in FIG. 7C.

The local application 728 may oversee the communication with the remote monitoring manager of the cloud environment and may oversee the monitoring application 730, the distress application 732, the non-distress application 734, the query opioid user application 736, and the local alarm application 738. The local application 728 is local in the sense that it as well as its associated applications 730-738, are located on the mobile communication device 722 associated with the opioid user, devices associated with organizations to assist opioid users, and devices associated with individuals that are associated with the opioid user.

The monitoring application 730 may receive the physiological parameters 118 and process the physiological parameters according to one or more of the steps of FIGS. 2B, 4. The monitoring application 730 may cause the display of the physiological parameters 118 on the display 724 mobile communication device 722. FIGS. 5A, 5D illustrate examples of displays of the physiological parameters.

The distress application 732 may be called when the monitoring application 730 determines that the opioid user is experiencing an overdose event or an overdose event is imminent. The distress application 732 may perform one or more steps of FIGS. 2B, 4, such as send out distress notifications. Further, the distress application 732 may communicate with the distress notification manager 716 in the cloud environment 702 to cause the distress notification manager to provide distress notifications as described above.

The non-distress application 734 may be called when the monitoring application 730 determines that the opioid user is not experiencing an overdose event or an overdose event is not imminent. The non-distress application 734 may perform one or more steps of FIGS. 2B, 4, such as send status notifications. Further, the non-distress application 734 may communicate with the non-distress notification manager 718 in the cloud environment 702 to cause the non-distress notification manager to provide status notifications as described above.

The query opioid user application 736 may be called when the monitoring application 730 determines that care is indicated. The query opioid user application 736 queries the user to determine whether the user is conscious in order to reduce false alarms. The query opioid user application 736 may perform step 235 of FIG. 2B. FIG. 3A illustrates a display to query the user that may be caused by the query opioid user application 736.

The local alarm application 738 may be called when the monitoring application 730 determines that on-site care of the opioid user is required. The local alarm application 738 may perform step 430 of FIG. 4. The local alarm application 738 may cause the mobile communication device 722 to display first responder instruction, a map or directions to the nearest facility with medication to reverse or reduce the effects of an overdose, such as naloxone, and the like. The local alarm application 738 may cause the mobile communication device 722 to audibly alarm and/or visually alarm to alert anyone near the mobile communication device 722 of the overdose event. FIG. 3D illustrates an example of a first responder instructions and FIG. 3E illustrates an example of a display displaying the location of naloxone.

Figure 8:
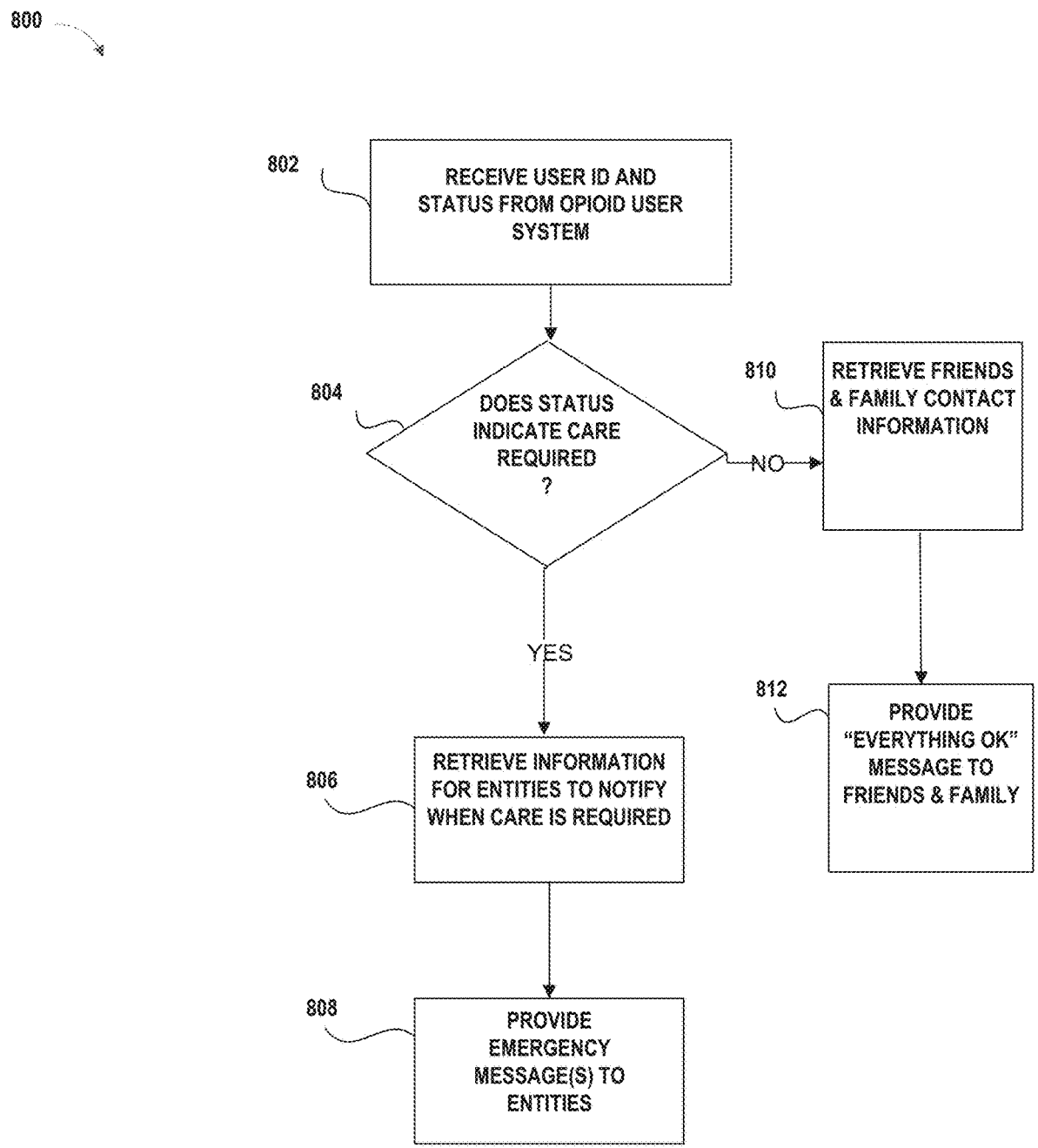
FIG. 8 is a flowchart of an example process to notify an opioid user's notification network of the status of the opioid user.

FIG. 8 is a flowchart of an example process 800 to notify an opioid user's notification network of the status of the opioid user. The process 800 can be performed by the cloud environment 702. At block 802, the cloud environment 702 receives a user identification and user status from the opioid monitoring system 706. For example, the remote application manager 710 retrieves the user information from the database 720 based on the user identification.

At block 802, the cloud environment 702 may determine, based on the status of the user, whether care is indicated. The status information may comprise the physiological parameters 118 from the monitoring application 730. The status may be an indication of whether care is indicated or not indicated. Remote application manager 710 may analyze the physiological parameters 118 to determine whether care is indicated.

If care is indicated at block 804, the process 800 moves to block 806. At block 806, the distress notification manager 716 may retrieve the contact information stored in the database and associated with the user identification.

At block 808, the distress notification manager 716 may notify the individuals and organizations of the contact information of the need for care.

If care is not indicated at block 804, the process 800 moves to block 810. At block 810, the non-distress notification manager 718 may retrieve the contact information stored in the database and associated with the user identification.

At block 812, the non-distress notification manager 718 may notify the individuals and organizations of the contact information of the status of the opioid user. The non-distress notification manager 718 can send an "Everything OK" message.

Communication Between Opioid Overdose Monitoring Application and Transportation/Ride Sharing Services A mobile device or other computing device executing the opioid monitoring application can communicate with one or more transportation services such as, a ride sharing service, such as Lyft® or Uber®, for example, a taxi service, or any commercial transportation service, when an overdose event is occurring or imminent. This is illustrated in FIG. 1B as "Rideshare network" that is within the representation of the location of naloxone message. The opioid monitoring application may communicate, via the mobile computing device, with servers associated with the ridesharing services over a network such as the Internet. The communication can be entered into the transportation service system the same as a person would normally call for a taxi, Lyft, or Uber, for example.

The transportation service can receive a notification from the mobile device or other computing device that is deploying the opioid overdose monitoring application. The notification can be an alert. The alert may be for an ongoing or an imminent opioid overdose event. The notification may include the address of the opioid user, the address of the nearest facility with medication to reverse or reduce the effects of an overdose, such as naloxone, buprenorphine, combination of buprenorphine and naloxone, and the like, and the address of the nearest caregiver, emergency service, treatment center, and other organizations or individuals that can provide life-saving care to for the opioid user.

The transportation service can transport the opioid user to receive care, transport the opioid user to a location having the medication, transport the medication to the opioid user, to pick up the medication and transport the medication to the opioid user, and the like.

The transportation service or ride sharing service can bill for the transportation that occurs after receiving an alert or notification generated by the opioid overdose monitoring application as a special billing or a charitable billing. The transportation service or ride sharing service can bill for the transportation in the same manner that its transportation services are billed for a typical customer.

The transportation service or ride sharing service can participate in a community outreach program to provide transportation responsive to receiving an alert or notification generated by the opioid monitoring application.

Figure 9A:
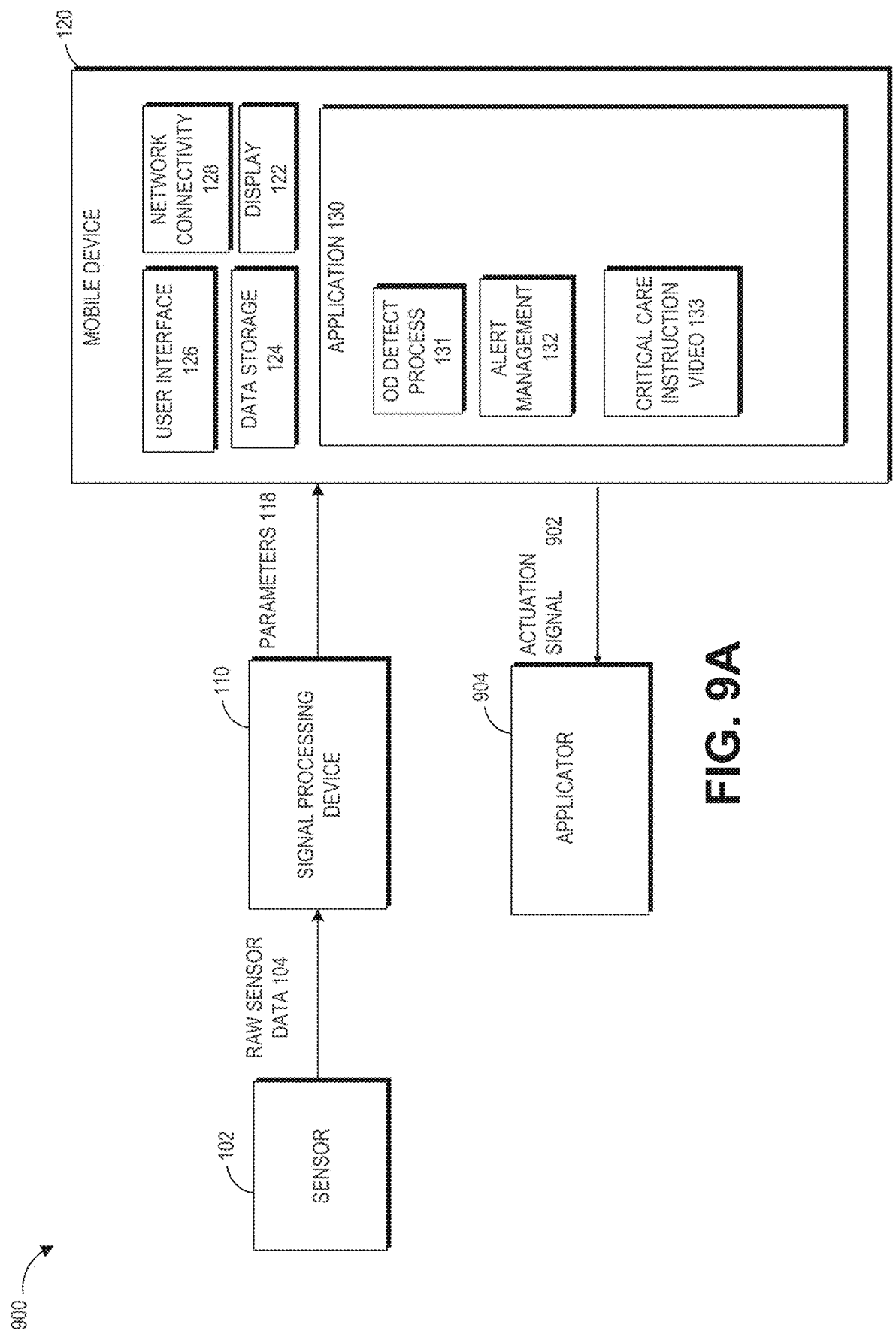
FIG. 9A is a block diagram of an example physiological monitoring and medication administration system.

Physiological Monitoring and Medication Administration System Including Activation Circuitry FIG. 9A is a block diagram of an example physiological monitoring and medication administration system 900. The illustrated physiological monitoring and medication administration system 900 is like the physiological monitoring system 100 of FIG. 2A except that an applicator 904 having medication to reverse or reduce the effects of an opioid overdose, such as an opioid receptor antagonist, and at least signal 902 from the mobile communication device 120 to actuate the applicator 904 are included in the physiological monitoring and medication administration system 900.

Figure 13:
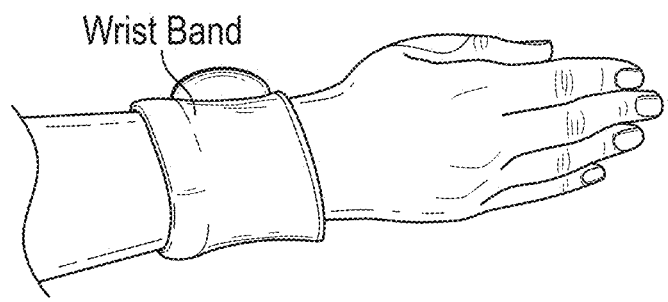
FIG. 13 is a schematic diagram of an example wearable self-administrating medication applicator.

The applicator 904 can be worn by the user in a manner that facilitates the application of the medication. For example, the applicator 904 can be strapped to the user's wrist, as illustrated in FIG. 13, and the medication can be applied through the skin, intramuscularly, or intravenously. The applicator can be configured as a watch band, a bracelet, a vest-like garment worn next to the user's skin, or the like. The applicator can be configured to apply the medication intranasally, sublingually, or other methods of application.

Figure 9B:
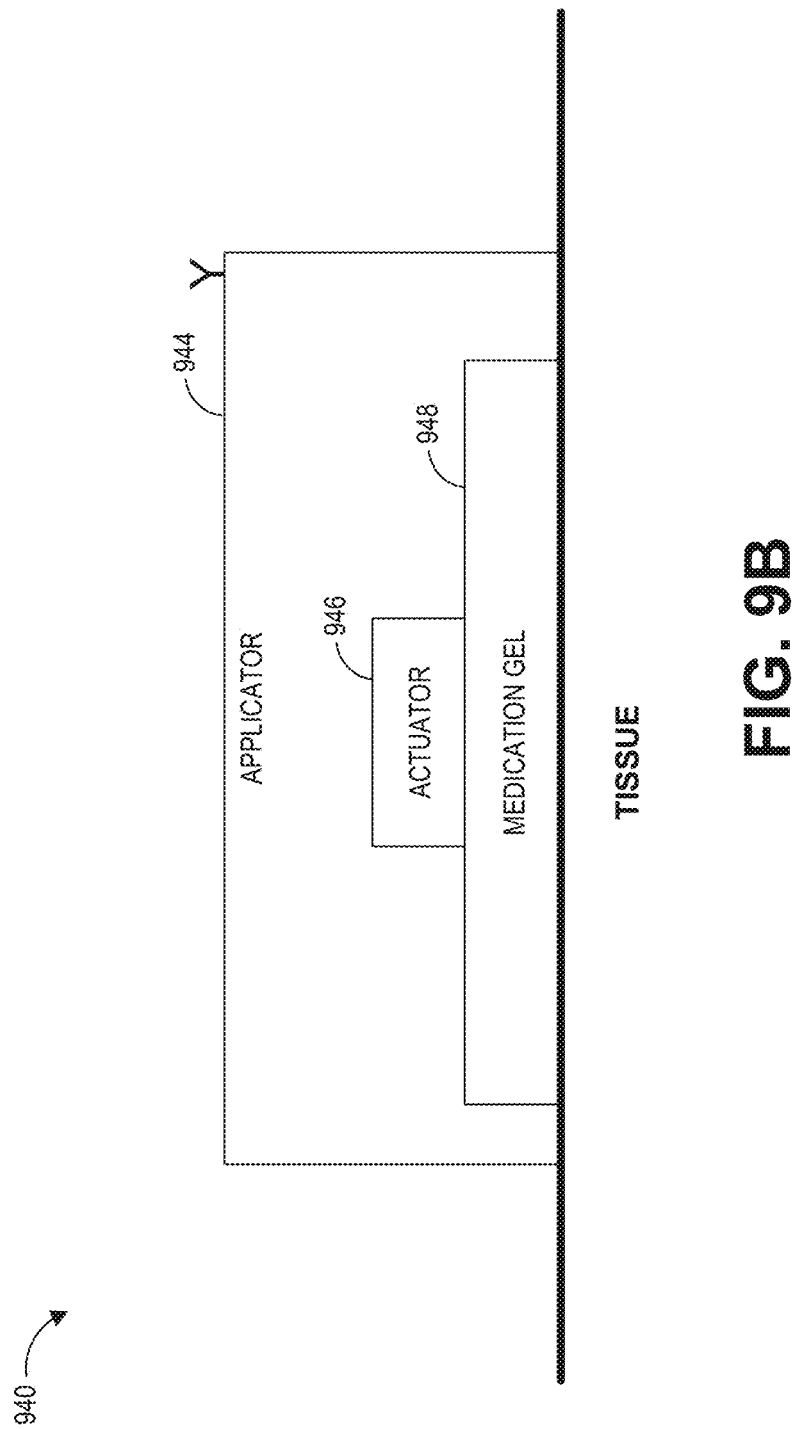
FIGS. 9B and 9C are schematic diagrams of example self-administrating medication applicators.
Figure 9C:
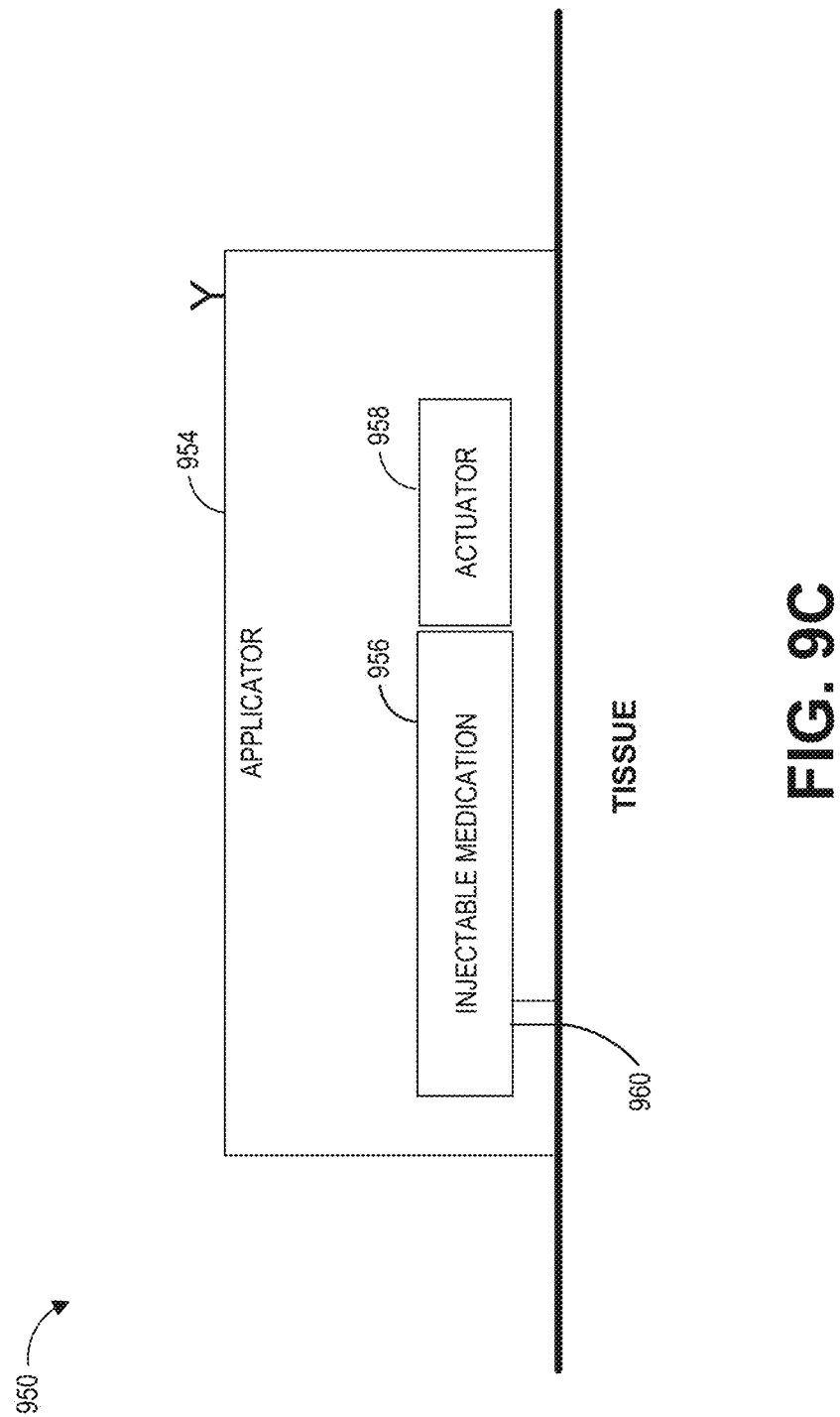

FIGS. 9B and 9C are schematic diagrams 940, 950 of example self-administrating medication applicators. FIG. 9B illustrates an applicator 944 configured to apply topical medication to reverse or reduce the effects of an opioid overdose. The applicator 944 includes an actuator 946 and medication in gel form 946. The gel 946 may be contained in a pouch or container with frangible seals, for example. The actuator 946 can receive the actuation signal 902 from the mobile device 120 to initiate the actuation process. In the illustrated applicator, the actuation signal 902 is received via an antenna. The actuation signal 902 can be in electrical communication with the applicator 944 via one or more wires. Once the applicator 944 receives the actuation signal 902, the actuator can actuate to dispense the gel 948 onto the skin or tissue of the user. For example, the actuator can include a gas squib, that when activated, creates a pressurized gas or fluid that is in fluid contact with the gel 948, via one or more conduits, for example. The pressurized fluid forces the gel 948 to break frangible seals next to the tissue, causing the gel 948 to be applied to the surface of the tissue.

FIG. 9C illustrates an applicator 954 configured to inject medication to reverse or reduce the effects of an opioid overdose into the tissue of the user. The applicator 954 includes a vial or container of injectable medication, an actuator, and a needle 960. The needle 960 can be a microneedle. The actuator can receive the actuation signal from the mobile communication device 120 to initiate the actuation process. In the illustrated applicator, the actuation signal 902 is received via an antenna. The actuation signal 902 can be in electrical communication with the applicator 944 via one or more wires. Once the applicator 944 receives the actuation signal 902, the actuator 958 can actuate to force, by using pressure as described above, for example, the injectable medication 956 through the needle 960. The needle 960 can be configured to inject the medication 956 into the tissue under the pressure generated by the actuator 958.

Figure 10:
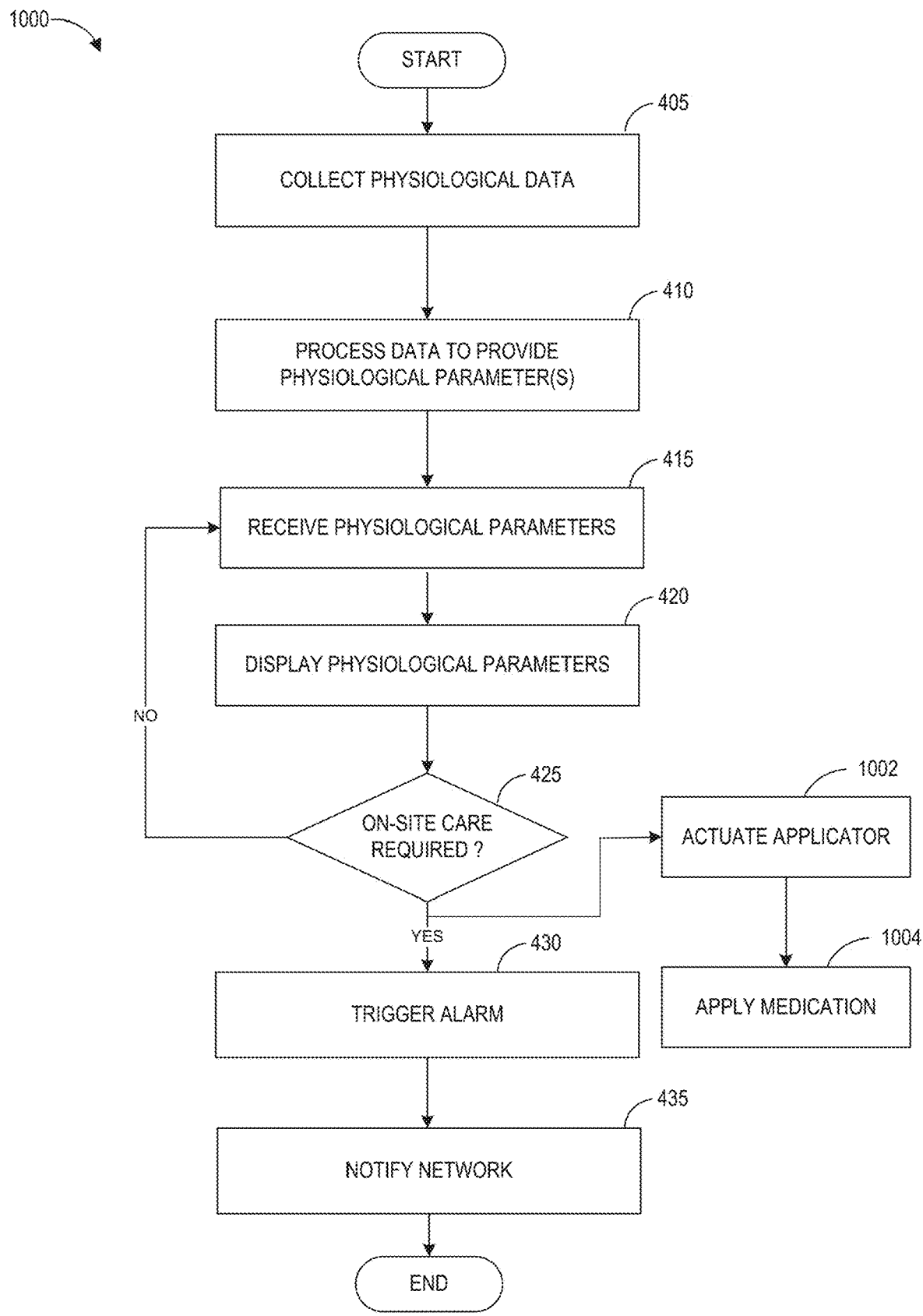
FIG. 10 is a flow diagram of an example process to monitor for opioid overdose and to apply medication to reverse the effects of an overdose.

FIG. 10 is a flow diagram of an example process 1000 to monitor for opioid overdose and to apply medication to reverse the effects of an overdose. The process 1000 is like the process 400 of FIG. 4 except that the process 1000 includes steps activate an applicator worn on the body of the user, such applicator 904, 944, 954, and the like, to apply the medication to revere or reduce the effects of an opioid overdose. Once the need for on-site care is determined at block 425, the process 1000 moves to block 430 to trigger an alarm and also to block 1002. At block 1002, the applicator 904, 944, 954 receives an actuation signal 902, which actuates the applicator 904, 944, 954. At block 1004, the medication is dispensed from the application 904, 944, 954, and applied to the user. The medication can be applied topically, through intramuscular injection, through intravenous injection, and the like, to the user to reverse or reduce the effects of the opioid overdose.

Figure 11A:
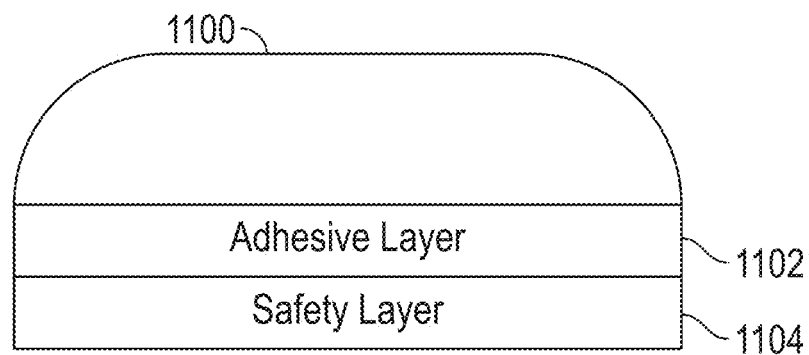
FIGS. 11A-11C are schematic diagrams of example needle-free injection multi-dose self-administrating medication applicators.
Figure 11B:
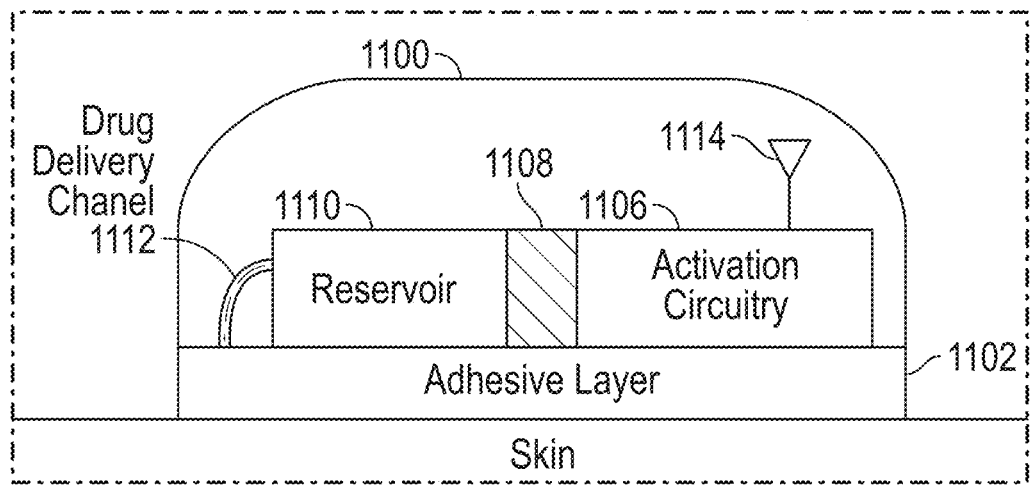
Figure 11C:
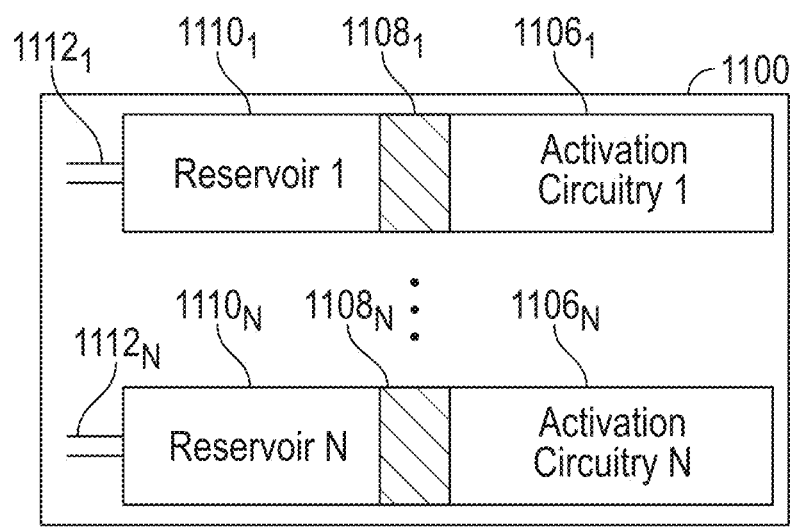

FIGS. 11A-11C are schematic diagrams of an example needle-free injection, multi-dose, self-administrating medication applicator 1100. The applicator 1100 can be configured to inject, without a hypodermic needle, one or more doses of medication to reverse or reduce the effects of an opioid overdose into the tissue of the user. FIG. 11A illustrates a side view of the needle-free injection, multi-dose, self-administrating medication applicator 1100 comprising an adhesive layer 1102 configured to adhere the applicator 1100 to the skin and a protective or safety layer 1104 configured to inhibit inadvertent dispensing of the medication. Other safety mechanism, such as a latch or safety catch can be used to prevent inadvertent dispensing of the medication. To prepare the applicator 1100 for use, the user or caregiver removes the safety layer 1104 and adheres the applicator 1100 to the opioid user's skin.

FIG. 11B illustrates a cut-away side view of the applicator 1100 further comprising one or more activation circuitry 1106, antenna 1114, plunger or other dispensing mechanism 1108, reservoir 1110, and drug delivery channel 1112. The activation circuitry 1106 is configured receive an activation signal via the antenna 1114 and activate a delivery mechanism 1108 to dispense medication in the reservoir 1110 through the drug delivery channel 1112 through the skin, intramuscularly or intravenously. The medication can be naloxone, an opioid receptor antagonist, or the like to reduce the effects of an opioid overdose event. The delivery mechanism 1108 can be a plunger propelled forward by a propellant such as a $CO_2$ cartridge, gas squib, compressed air, and $N_2$ gas cartridge, a pump motor, spring, and the like. The drug delivery channel 1112 can be a small bore tube that forces the medication through the adhesive 1102 and the skin as a high pressure spray like a jet spray. The applicator 1100 deposits the medication in the tissue under the administration site.

FIG. 11C illustrates a top cut away view of an example of the needle-free injection multi-dose self-administrating medication applicator 1100. The applicator 1100 further comprises multiple doses of the medication. In the illustrated example, the applicator comprises 1 to N applications, where each application is administered by activation circuitry activating a plunger or other dispensing mechanism to dispense the medication in the reservoir through the drug delivery channel as described above in FIG. 9B. Each activation circuitry 1106 can receive an activation signal via the antenna 1114, where each antenna 1114(1) to 1114(N) can be tuned to receive a unique activation signal such that only one activation circuit activates. More than one of antenna 1114(1) to 1114(N) can be tuned to activate with the same signal to dispense medication from more than one reservoir upon receipt of the activation signal.

Figure 12A:
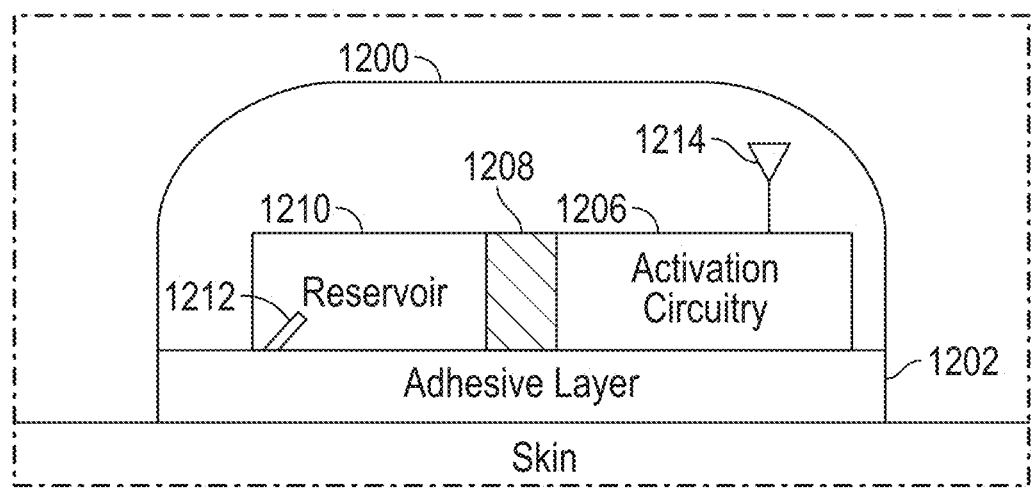
FIGS. 12A and 12B are schematic diagrams of example injection multi-dose self-administrating medication applicators having a hypodermic needle for injection.
Figure 12B:
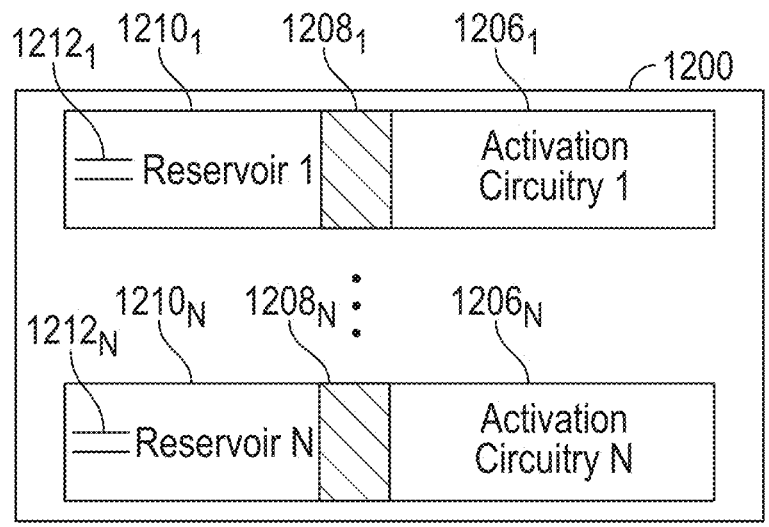

FIGS. 12A-12B are schematic diagrams of an example injection, multi-dose, self-administrating medication applicator 1200. The applicator 1200 is configured to inject, using a hypodermic needle, one or more doses of medication to reverse or reduce the effects of an opioid overdose into the tissue of the user. FIG. 12A illustrates a cut-away side view of the injection multi-dose self-administrating medication applicator 1200 comprising an adhesive layer 1202 configured to adhere the applicator 1200 to the skin, one or more activation circuitry 1206, antenna 1214, plunger or other dispensing mechanism 1208, reservoir 1210, and needle 1212, which is shown in the retracted state. In the illustrated example, a safety layer configured to inhibit inadvertent dispensing of the medication has been peeled away and the applicator 1200 is adhered to the skin of the user at the dispensing site. Other safety mechanisms, such as a latch, safety catch, or cap over the needle 1212 can be used to prevent inadvertent dispensing of the medication. To prepare the applicator 1200 for use, the user or caregiver removes the safety layer and adheres the applicator 1200 to the opioid user's skin. The needle 1212 can be a microneedle.

The activation circuitry 1206 is configured receive an activation signal via the antenna 1214 and activate a delivery mechanism 1208 to dispense medication in the reservoir 1210 through the needle 1212 through the skin, intramuscularly or intravenously. The medication can be naloxone, an opioid receptor antagonist, or the like to reduce the effects of an opioid overdose event. The delivery mechanism 1208 can be a plunger propelled forward by a propellant such as a $CO_2$ cartridge, gas squib, compressed air, and $N_2$ gas cartridge, a pump motor, spring, and the like. The pressure from the delivery mechanism 1208 pushes the medication through the needle and causes the needle 1212 to move forward through the adhesive layer 1202 and into the skin, muscle, vein or the like at the deliver site. The needle 1212 can be a hypodermic needle or any sharp configured to inject substances into the body. The applicator 1200 deposits the medication in the tissue under the administration site.

FIG. 12B illustrates a top cut away view of an example of the injection multi-dose self-administrating medication applicator 1200. The applicator 1200 further comprises multiple doses of the medication. In the illustrated example, the applicator 1200 comprises 1 to N applications, where each application is administered by activation circuitry activating a plunger or other dispensing mechanism to dispense the medication in the reservoir through the needle as described above in FIG. 9B. Each activation circuitry 1206 can receive an activation signal via the antenna 1214, where each antenna 1214(1) to 1214(N) can be tuned to receive a unique activation signal such that only one activation circuit activates. More than one of antenna 1214(1) to 1214(N) can be tuned to activate with the same signal to dispense medication from more than one reservoir upon receipt of the activation signal.

Figure 14:
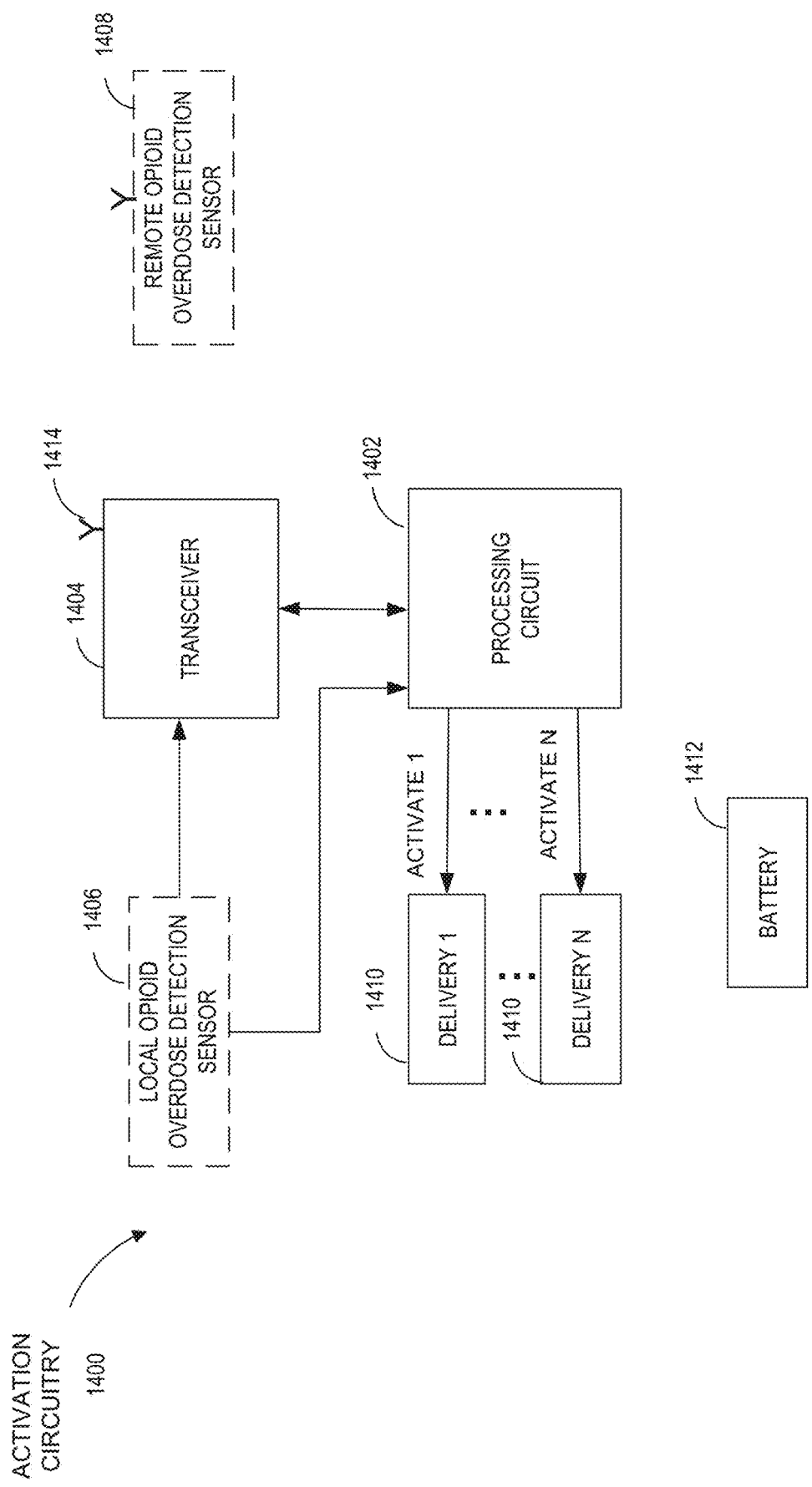
FIG. 14 is a block diagram of example activation circuitry for multi-dose self-administrating medication applicators.

FIG. 14 is a block diagram of example activation circuitry 1400 for multi-dose, self-administrating medication applicators, such as applicators 1100 and 1200. The illustrated activation circuitry 1400 comprises one or more antenna 1414, processing circuitry 1402, and a plurality of delivery circuitry and mechanisms 1410. A battery 1412 can be used to power the activation circuitry 1400.

The applicator 1100 can further comprise an opioid overdose detection sensor 1406, which can be considered a local opioid overdose detection sensor because it is local to the user. The local opioid overdose detection sensor 1406 can receive sensor data from the opioid user. Local opioid overdose detection sensor 1406 sends the sensor data to the processing circuitry 1402. The processing circuitry 1402 receives the sensor data from the local opioid overdose detection sensor 1406, processes the sensor data, and determines whether an opioid overdose event is occurring or will soon be occurring. The local opioid overdose detection sensor 1406 can send the sensor data to the transceiver 1404. The transceiver 1404 sends the sensor data via the one or more antenna 1414 to at least one of the mobile device 120, the server, and the hub for processing. Once the data is processed, the transceiver 1404 can receive via one or more antenna 1414 a signal indicating that the opioid overdose event is occurring or soon will be occurring. The transceiver 1404 sends the processing circuitry 1402 an indication that the opioid overdose event is occurring or soon will be occurring.

The applicator 1100, 1200 may not include an opioid overdose detection sensor 1408, such that the opioid overdose detection sensor 1408 can be considered remote from the applicator 1100, 1200. The remote opioid detection sensor 1408 can send the sensor data to at least one of the mobile device 120, the server, and the hub and when the processed sensor data indicates that an opioid overdose event is occurring, the transceiver 1404 receives via one or more antenna 1414 a signal indicating that an opioid overdose event is occurring or soon will be occurring. The transceiver 1404 sends the processing circuitry 1402 an indication that the opioid overdose event is occurring or soon will be occurring. The remote opioid detection sensor 1408 can send sensor data wirelessly or through a wired connection to the processing circuitry 1402.

The processing circuitry 1402 can determine that the opioid overdose event is occurring or will soon occur by processing the sensor data from the local opioid overdose detector sensor 1406 or can receive an indication from the transceiver 1404 that the opioid overdose event is occurring or will soon occur. The processor 1402 can generate one or more activate signals ACTIVATE(1) to ACTIVATE(N) to the delivery systems DELIVERY(1) to DELIVERY(N), respectively, to dispense one or up to N doses of the medication. For example, if the physiology of the user is such that a single dose of medication is insufficient, the processing circuitry 1402 may be programmed to deliver multiple doses at approximately the same time.

The processing circuitry 1402 can generate more than one activate signal at approximately the same time to deliver more than one dose of the medication to the user at approximately the same time. The processing circuit 1402 can generate successive activate signals in response to successive indications of an overdose event. For example, if the application of a first dose of medication does not reverse the effects of an opioid overdose, the processing circuitry 1402 can generate a second activation signal to provide a second dose of medication to the user. The activation circuitry 1400 can count the number of doses dispensed and provides an alert when the applicators 1100, 1200 are empty.

Figure 15:
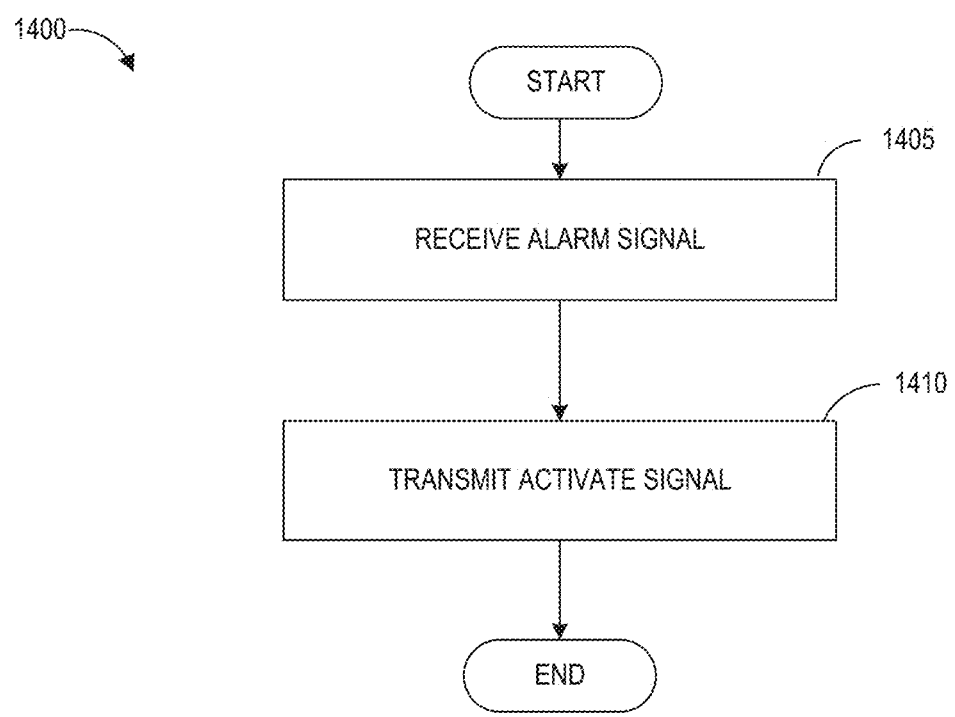
FIG. 15 is a flow diagram of an example process to administer medication from a self-administrating medication applicator.

FIG. 15 is a flow diagram of an example process 1500 to administer medication from a self-administrating medication applicator 1100, 1200. At step 1415, the activation circuitry 1400 receives an indication that an opioid overdose event is occurring or soon will be occurring. At step 1420, the processing circuitry 1402 transmits at least one activate signal to the at least one delivery circuit DELIVERY(1) to DELIVERY(N) to dispense at least one dose of the medication.

Figure 16A:
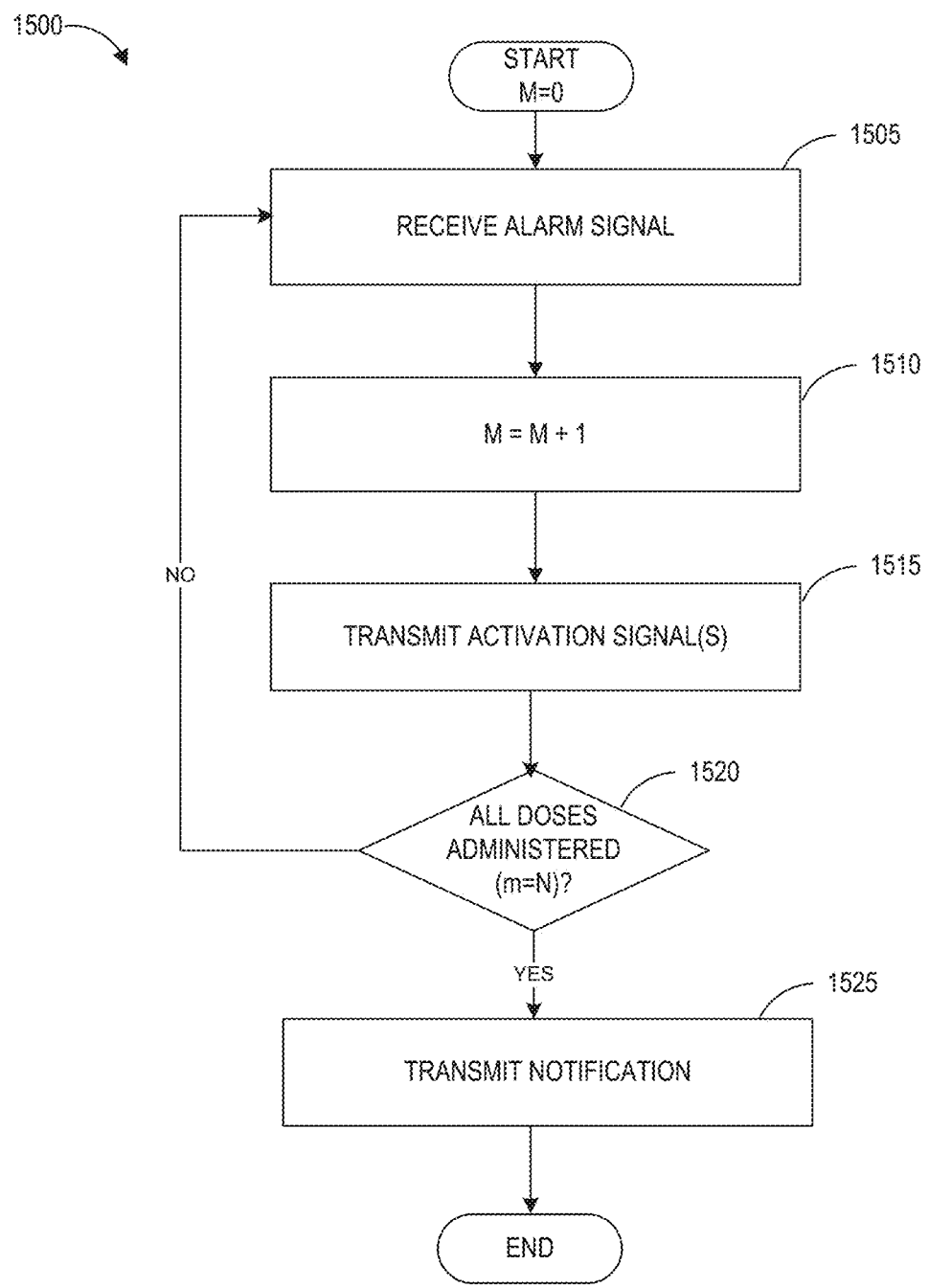
FIGS. 16A and 16B are flow diagrams of example processes to administer multiple doses of medication from a self-administrating medication applicator.
Figure 16B:
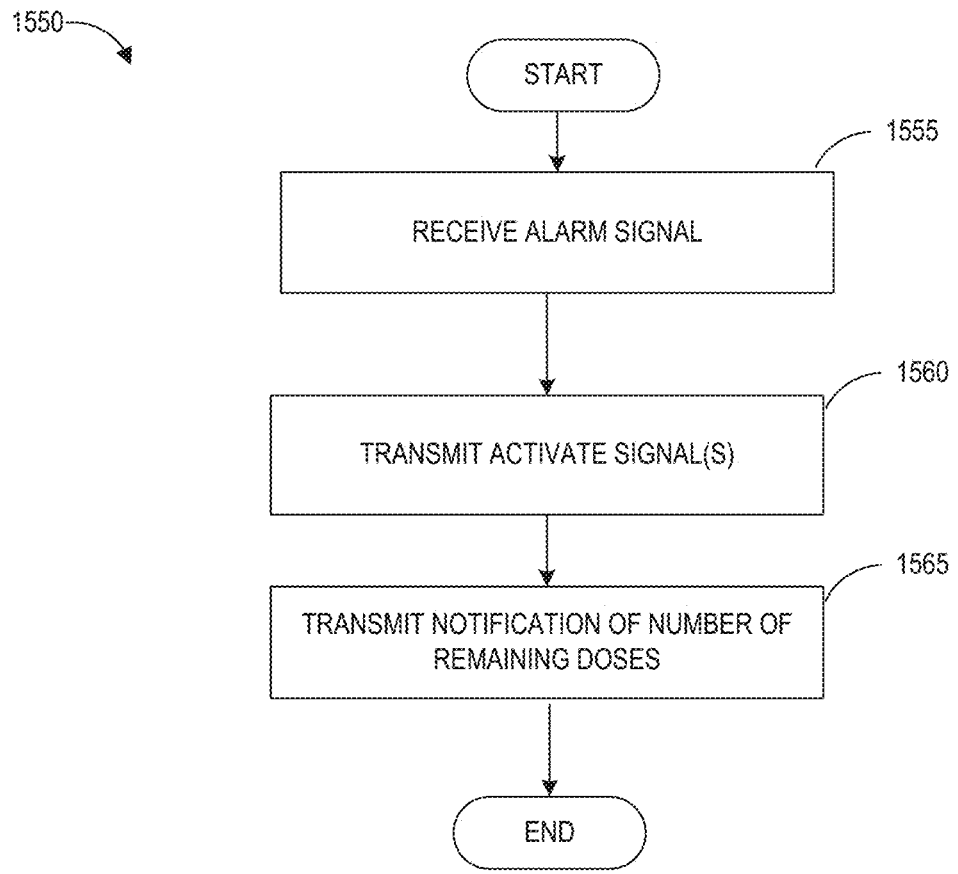

FIGS. 16A and 16B are flow diagrams of example processes 1500, 1550 to administer multiple doses of medication from a self-administrating medication applicator. Processes 1500, 1550 utilize a bi-directional communication link between the activation circuitry 1400 and at least one of the mobile device 120, the server, and the medical monitoring hub.

Referring to FIG. 16A, at the start of process 1500 a counter m can be initialized to zero. At step 1505, the activation circuitry 1400 receives an alarm signal indicting an overdose event. At step 1505, the counter is incremented.

At step 1515, the processing circuitry 1402 transmits activation signal to the delivery circuitry to deliver the medication to the user. At step 1520, the processing circuitry 1402 determines whether all of the doses in the multi-dose self-administrating medication applicators 1100, 1200 have been activated. The count m can be compared to the number of doses N in the applicator 1100, 1200. When there are doses remaining in the applicator 1100, 1200 (m<N), the process 1500 returns to step 1505. When there are no more doses of the medication in the applicator 1100, 1200, (m=N), then the process 1500 moves to step 1525. At step 1525, the processing circuitry 1402 transmits, via the transceiver 1404 and one or more antenna 1414, a notification that the applicator 1100, 1200 is empty.

Referring to FIG. 16B, at process 1550, the activation circuitry 1400 receives an alarm signal that an opioid event is occurring or will soon occur. At step 1560, the processing circuitry 1402 transmits the activate signal to one or more of the delivery circuitry 1410 to deliver the medication to the user. At step 1465, the activation circuitry 1400 transmits, via the transceiver 1404 and the one or more antenna 1414, an indication of the number of remaining doses in the applicator 1100, 1200.

Patch with Pressurized Reservoir

Figure 17:
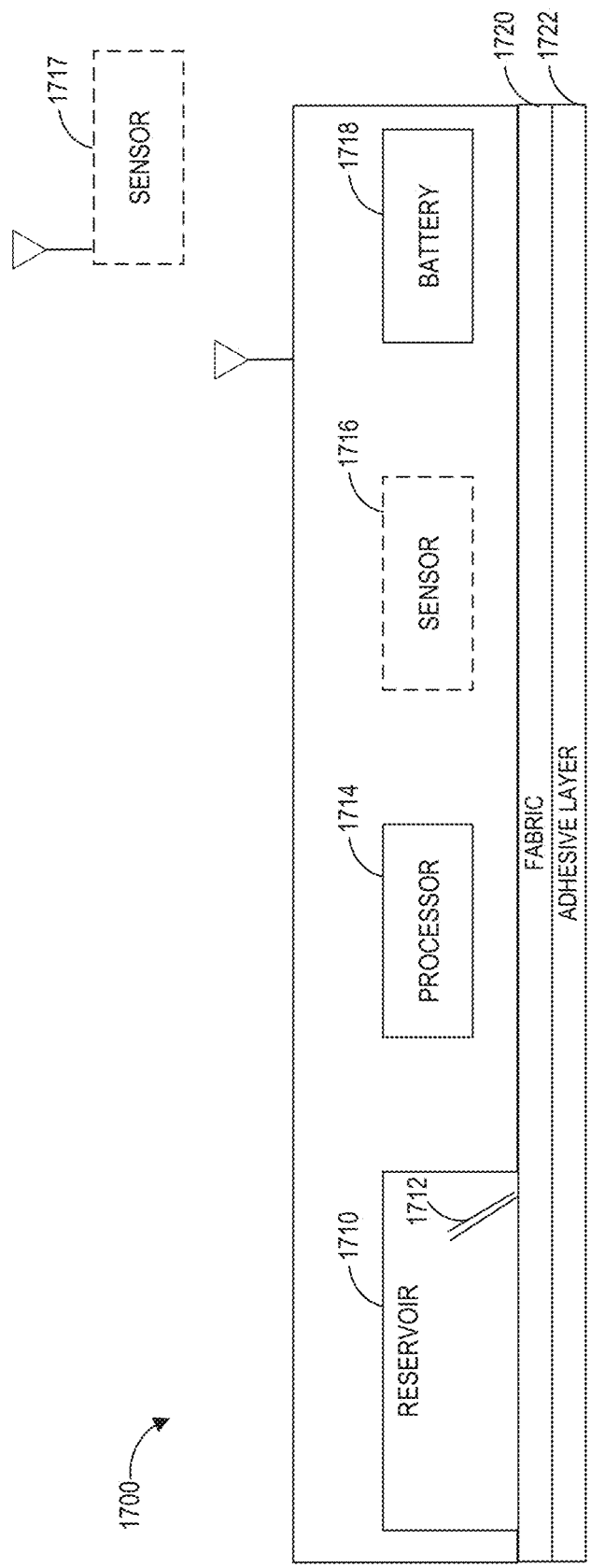
FIG. 17 is a schematic diagram of another example wearable self-administrating medication applicator.

FIG. 17 a schematic diagram of an example wearable self-administrating medication applicator 1700 that includes an antenna, a reservoir 1710, a needle 1712, a processor 1714, a sensor 1716, a battery 1718, a fabric layer 1720, and an adhesive layer 1722. The self-administrating medication application can be configured as a patch 1700 that is adhered to the user's skin by the adhesive layer 1722. The patch 1700 can provide opioid overdose monitoring and administration of an opioid receptor antagonist. The patch 1700 can be a single use, preloaded, disposable device.

The reservoir 1710 can include an opioid receptor antagonist, such as Naloxone which is dispensed via the needle 1712 into the user. The needle 1712 can be a microneedle. Sensor 1716 can be internal to the patch 1700 and monitors the user's physiological parameters. Instead of the patch 1700 including an internal sensor 1716, an external sensor 1717 can monitor the user's physiological parameters and can wirelessly communicate with the patch 1700 via the antennas. The external sensor 1717 can be wired to the patch 1700 and provide the sensor data via wires. External sensor 1717 can be a finger sensor that wraps around or over a finger or a toe a Sensor 1716 or sensor 1718 can include pulse oximeters, respiratory monitors, and other sensor devices disclosed herein that monitor the user's physiological parameters. The processor 1714 can process the sensor data to detect an overdose event. The patch 1700 can transmit the sensor data to an external processing device, such as a mobile device or a hub device for detection of an opioid overdose event.

The needle 1712 can be spring-loaded (e.g., in a switchblade like manner). Fabric layer 1720 can hold the spring-loaded needle 1712 in a compressed state without the spring-loaded needle puncturing the fabric layer 1720. When an opioid overdose event is detected, the battery 1718 can release a charge that passes through at least a portion of the fabric layer 1720. The fabric layer 1720 receives the electrical charge from the battery 1718, which can cause the fabric layer 1720 to burn or shrink and the spring-loaded needle to be no longer restrained. The needle 1712 releases and can inject the user with the opioid receptor antagonist, such as Naloxone, stored in the reservoir. The reservoir 1710 can be pressurized to assist in the injection of the opioid receptor antagonist when the needle is released. An external pump can pressurize the reservoir 1710. The patch 1700 can have no mechanical triggers. The battery 1718 can be sized to provide operating power for approximately one week. The battery 1718 can be sized to provide operating power for more than one week, more than two weeks, more than one month, or greater periods of time.

Hub Based Opioid Monitoring System

Figure 18A:
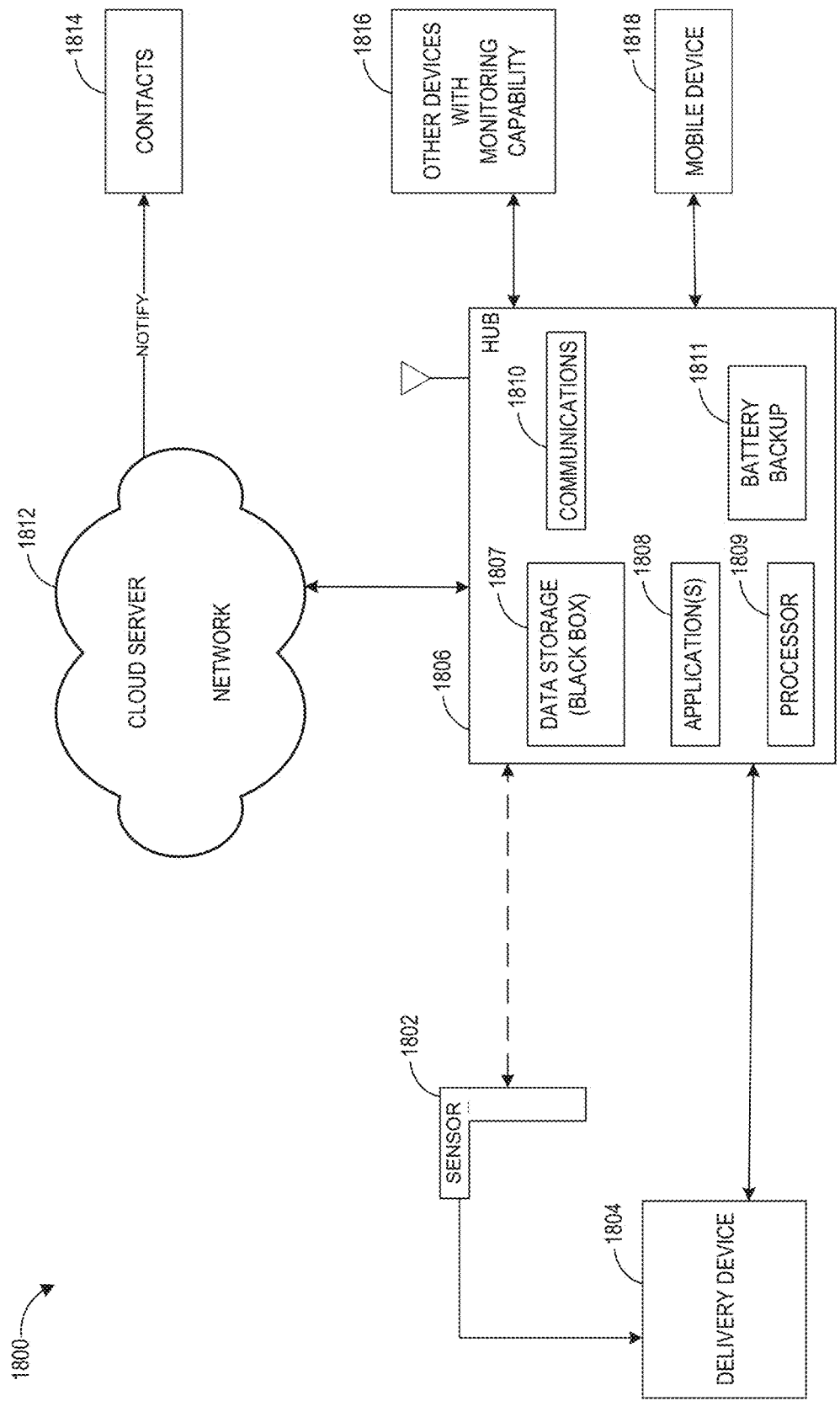
FIG. 18A is a block diagram of an example opioid use monitoring system.

FIG. 18A is a block diagram of an example opioid use monitoring system 1800 that includes a sensor 1802, a delivery device 1804, a medical monitoring hub device 1806, and a network 1812, such as the Internet hosting a cloud server, which can be considered a remote server because it is remote form the user. Sensor 1802 is configured to monitor the user's physiological parameters and deliver device 1804 is configured to deliver a dose of an opioid receptor antagonist, such as Naloxone or the like, when an opioid overdose event is detected. Sensor 1802 can be an oximetry device, respiration monitor, devices described herein to obtain the user's physiological parameters, and the like. The sensor 1802 can be an acoustic sensor, a capnography sensor or an impedance sensor to monitor the user's respiration rate. The sensor 1802 can includes the signal processing device 110 to process the raw sensor data.

Delivery device 1804 can be a self-administrating device, such as devices 940, 950, 1100, 1200, 1700. The delivery device can be a device that is user or responder activated. The sensor 1802 can be internal to the delivery device 1804. The sensor 1802 can be external to the delivery device 1804.

The hub device 1806 can be configured to collect data and transmit the data to a cloud server for evaluation. The hub device 1806 can comprise communications circuitry and protocols 1810 to communication with one or more of the delivery device 1804, the sensor 1802, network 1812, mobile communication device 1818, such as a smart phone and the like, and other devices with monitoring capabilities 1816. Communications can be Bluetooth or Wi-Fi, for example. The hub device 1806 can further comprise memory for data storage 1807, memory for application software 1808, and a processor 1809. The application software can include a reminder to put on the patch before sleeping. The hub device 1806 is powered by AC household current and includes battery backup circuitry 1818 for operation when the power is out. The hub device 1806 can be powered through a USB port, using a charger connected to an AC outlet or connected to an automobiles USB charging port. The hub device 1806 can annunciate a battery-low condition.

The hub device 1806 can be a Radius-7® by Masimo, Irvine, Calif. The hub 1806 can comprise at least the memory for data storage 1807 and the battery backup circuitry 1818 can physically interface and communicate with the Radius-7®. The hub device 1806 can interface with the phone cradle of the Radius-7®.

The sensor 1802 can monitor the user's physiological parameters and transmit the raw sensor data to the delivery device 1804, via wired or wireless communication. Optionally, the sensor 1802 can transmit the raw sensor data to the hub device 1806, via wired or wireless communication. The delivery device 1804 can process the raw sensor data to determine when an opioid overdose event occurs. The hub device 1806 can process the raw sensor data to determine when an opioid overdose event occur. The hub device 1806 can transmit the raw sensor data to a cloud server for processing to determine when an opioid overdose event occurs. When an opioid overdose event is imminent or occurring, the cloud server can transmit to the delivery device 1804 via the hub device 1806 instructions to activate and deliver the opioid receptor antagonist, such as Naloxone. The cloud server can further transmit messages to contacts 1814, such as friends, family emergency personnel, caregivers, police, ambulance services, other addicts, hospitals and the like. The hub device 1806 can send the delivery device 1804 instructions to activate.

It is important to avoid false-positive indications of an overdose event. Users may not wear the self-administrating delivery device 1804 if the user experiences delivery of the opioid receptor antagonist when an overdose event is not occurring or imminently going to occur. To avoid false-positive indications, the wearable delivery device 1804 can induce pain before administrating the opioid receptor antagonist when an overdose event is detected to inform the user that the antagonist will be administered. The wearable delivery device 1804 can provide electric shocks to the user to induce pain. The induced pain can escalate until a threshold is reached. The user can employ a manual override to indicate that the user is conscious and not in need of the opioid receptor antagonist. The override can be a button, switch, or other user input on the delivery device 1804, the mobile communication device 722 and/or the hub device 1806. The delivery device 1804, the mobile communication device 722 and/or the hub device 1806 can wait for the user input for a period of time before triggering the release of the opioid receptor antagonist to avoid false-positive indications. The period of time can be less than 1 minute, less than 5 minutes, less than 10 minutes, between 1 minute and 5 minutes, between 1 minute and 10 minutes, and the like.

The memory for data storage 1807 can store the raw sensor data. The memory for data storage can act as a "black box" to record data from a plurality of sources. It is critical to administer the opioid receptor antagonist to a user as soon as an opioid overdose event is detected. The opioid overdose event can be cessation of respiration or an indication that respiration will soon cease. The administration can be by a responder, such as a friend or emergency personnel, by a self-administrating device worn by the user, or by the user. To avoid missing any signs that lead to an opioid overdose event, the hub device 1806 can receive data from any devices with a monitoring capability. For example, many homes have household cameras which provide a video feed. Cell phones can provide text messages and also include microphones to record voice. The cell phone or smart phone can be configured to listen to breathing and transmit the breathing data. Intelligent personal assistants, such as Amazon's Alexa® controlled Echo speaker, Google's Google Assistant®, Apple's Siri®, and the like, for example, also include microphones and have the ability to interface with the Internet. Many household appliances, such as refrigerators, washing machines, coffee makers, and the like, include Internet of Things technology and are also able to interface with the Internet. Medical monitoring devices that are being used by the opioid user for medical conditions, such as ECG's may also provide additional data. Data from one or more of these devices can be stored in the memory 1807 and used by the hub device 1806 or sent to the cloud server and used by the cloud server to detect an opioid overdose event. The hub device 1806 can determine what monitoring and Internet-connected devices are available and connect wirelessly to the available monitoring and Internet connected devices to receive data.

The hub device 1806 can interface with an internet filter, such as a Circle® internet filter that connects to a home network to monitor content. The hub device 1806 can determine which network data is directed to the user's well-being and store the well-being data.

The data can comprise text messages, voice recordings, video, and the like. Because of privacy concerns, the hub device 1806 can determine which small portions of data are helpful to determining the user's physical condition and store only those portion of data.

Because devices can fail to connect to the Internet, it is important to have redundant systems to report the sensor data for overdose detection. In the event that the hub device 1806 fails to connect to the Internet 1812, the mobile device or other internet-connected devices found in the home can provide an internet connection. For example, the hub device 1806 can transmit the sensor data to the mobile device 1818 and the mobile device 1818 can transmit the sensor data to the cloud server for processing. The sensor 1802 or delivery device 1804 can communicate with the mobile device 1818 when the hub device to Internet connection fails. Intelligent personal assistants and IoT devices can also provide redundant (backup) internet communication. The hub device 1806 can annunciate when its internet connection fails.

The mobile device 1818 can monitor respiration rate, SPO2, or ECG in parallel with the sensor 1802 and hub device 1806 monitoring of the user's physiological parameters to increase the likelihood that an imminent overdose will be detected. The sensor 1802 can monitor the concentration of an opioid in the user's bloodstream. The measured concentration can be a factor in determining an opioid overdose event to reduce instances of false positives.

A home security monitoring system can include the hub device 1806 and a home security company can monitor the user's health via the hub device 1806 and sensor 1802.

The opioid overdose monitoring application can be integrated into intelligent personal assistants, such as Amazon's Alexa®, for example.

The delivery device 1804 can include medication to induce vomiting. The opioid user can ingest the vomit-inducing medication, if desired, to regurgitate any opioid substance remaining in the user's stomach. The delivery device 1804 can include reservoirs containing the vomit-inducing medication and a position-sensing sensor. The vomit-inducing medication can be automatically dispensed after receiving sensor input indicating that the user is in an upright position.

The position-sensing sensor can monitor the user's movements to determine that the user is upright. The delivery device 1804 can include one or more sensors configured to obtain position, orientation, and motion information from the user. The one or more sensors can include an accelerometer, a gyroscope, and a magnetometer, which are configured to determine the user's position and orientation in three-dimensional space. The delivery device 1804 or the hub device 1806 can be configured to process the received information to determine the position of the user.

Figure 18B:
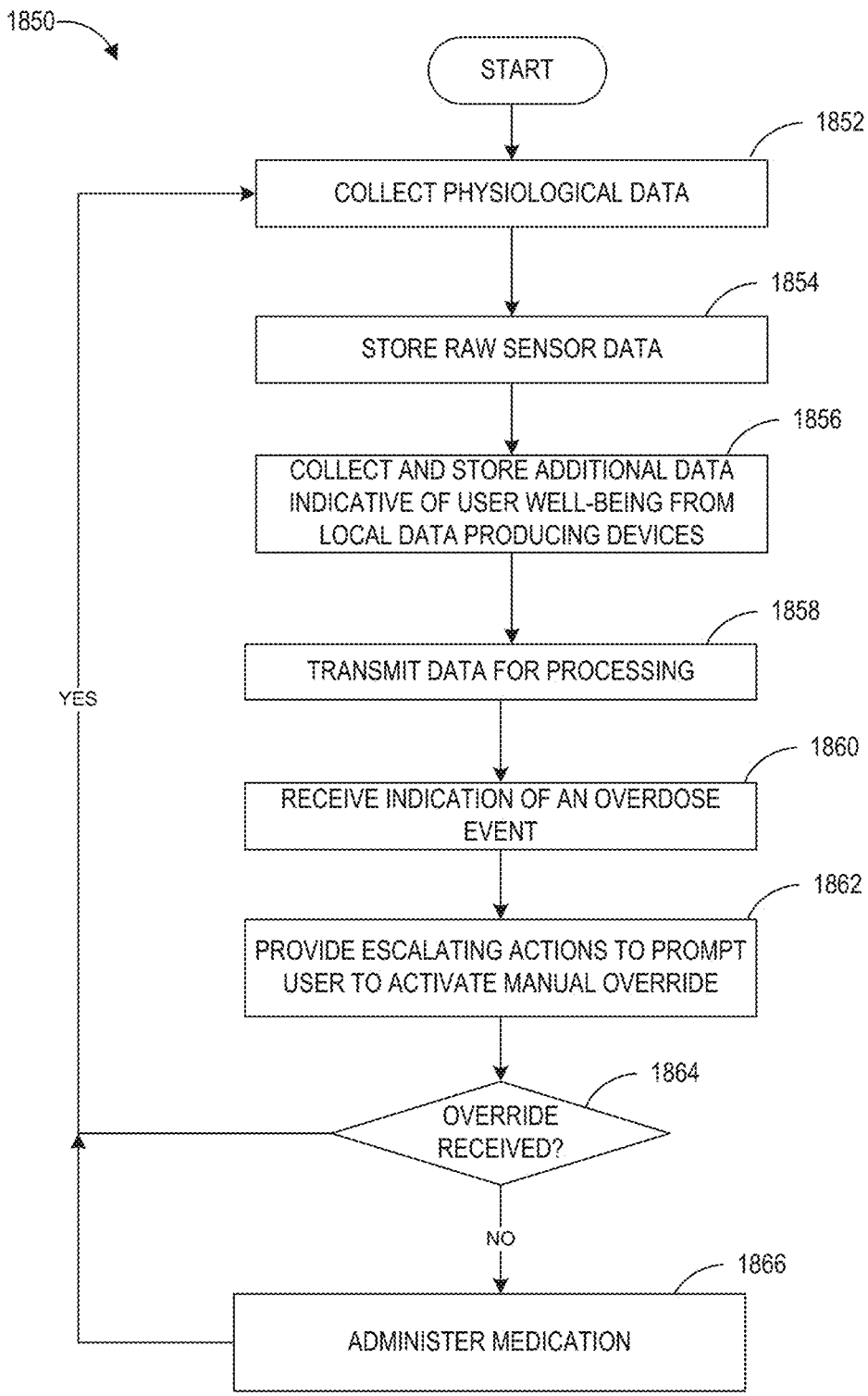
FIG. 18B is a flow diagram of an example process to administer the opioid receptor antagonist using the system of FIG. 18A.
Figure 19:
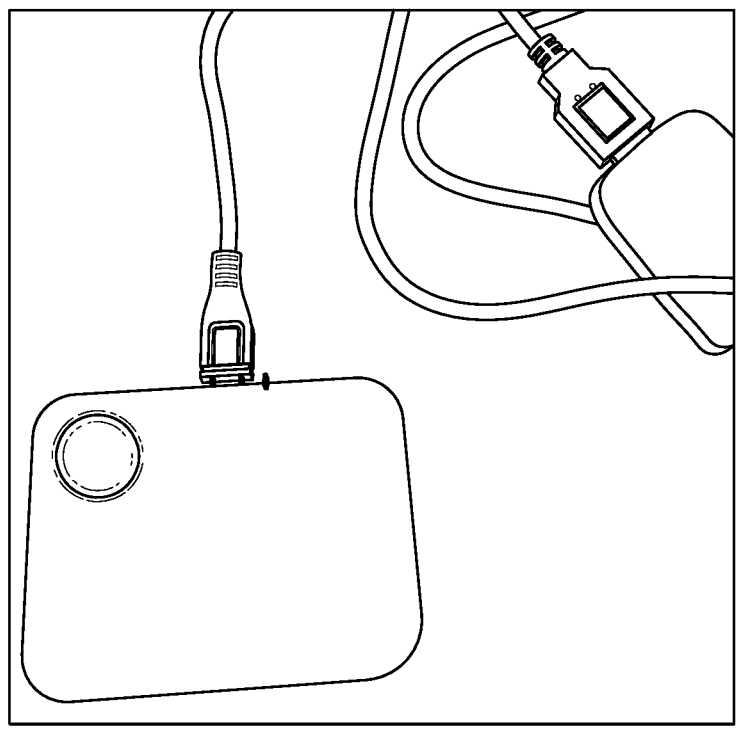
FIG. 19 is an example of a medical monitoring hub device used on the opioid use monitoring system of FIG. 18.

FIG. 19 illustrates an example hub device 1900 of the opioid overdose monitoring system of FIG. 18A. FIG. 18B is a flow diagram of a process 1850 to administer the opioid receptor antagonist using the system of FIG. 18A. At block 1852, the sensor 1802 can collect raw sensor data that comprises physiological data. The sensor 1802 can transmit the raw sensor data to the delivery device 1804 and the delivery device 1804 can transmit the raw sensor data to the hub device 1806. Alternately, the sensor 1802 can transmit the raw sensor data to the hub device 1806.

At block 1854, the hub device 1806 can store the raw sensor data. At block 1856, the hub device 1806 can collect and store data associated with the user's well-being from other devices local to the user. For example, the hub device can receive data from one or more home cameras, data from microphones and cameras of intelligent home assistants, such as Alexa®, for example, internet data from a home internet filter, and the like.

At block 1858, the hub device 1806 can transmit via the network 1812, the stored data to a cloud server for processing. The cloud server can process the data to determine whether an opioid overdose event is occurring or will be imminent. At block 1860, the hub device 1806 can receive from the cloud server an indication that an opioid overdose event is occurring or imminent. The hub device 1806 can transmit the indication to the delivery device 1804.

At block 1862, the delivery device 1804 can provide the user with escalating actions to prompt the user to activate a manual override to indicate that the opioid overdose event is not occurring. For example, the delivery device can provide increasing electric shocks to the user, up to a threshold.

At block 1864, the delivery device 1804 can determine whether an override from the user has been received. When an override is indicated, such as from a user activated button or switch on the delivery device 1804, the process 1850 returns to block 1852 to continue collecting physiological parameters. When an override is not indicated, the process 1850 moves to block 1866. At block 1866, the delivery device 1804 administers the medication, such as Naloxone or other opioid receptor antagonist and returns to block 1852 to continue monitoring the physiological parameters.

FIGS. 18A1-18A25 illustrate various example software applications to trigger an alarm and notify a friend when an opioid overdose is indicated. The software application can be downloaded onto the user's smart mobile device 1818.

FIG. 18A1 is an example screenshot illustrating a welcome message to a new user of the opioid overdose monitoring application. The illustrated screenshot of FIG. 18A1 displays an illustration of a hand wearing an example sensor and signal processing device 1802. The user can create an account for the overdose monitoring application. Once account registration is successful, the example application 1808 can instruct the user to set up the communications between the mobile device 1818, the sensor and signal processing device 1802, the medical monitoring hub device 1806, and the home Wi-Fi network.

FIG. 18A2 is an example screenshot illustrating instructions to the user to power the medical monitoring hub device 1806 to wireless connect to the mobile device 1818. For example, the medical monitoring hub device 1806 can be Bluetooth enabled. FIG. 18A3 is an example screenshot illustrating that the medical monitoring hub device 1806 is successfully connected.

FIGS. 18A4-18A6 are example screenshots illustrating instructions to power the sensor and signal processing device 1802 in order to wirelessly connect to the medical monitoring hub device 1806. The illustrated screenshot of FIG. 18A4 displays an illustration of the signal processing portion of the sensor and signal processing device 1802 in an open state to receive an integrated circuit ("chip"). The illustrated screenshot of FIG. 18A5 displays an illustration of the signal processing portion of the sensor and signal processing device 1802 in a closed state. The illustrated screenshot of FIG. 18A6 displays an illustration of the sensor portion of the sensor and signal processing device 1802 in a powered state.

FIG. 18A7-18A8 is are example screenshots illustrating instructions to pair the powered sensor and signal processing device 1802 with the medical monitoring hub device 1806. For example, the sensor and signal processing device 1802 can be Bluetooth enabled.

The user can allow the software application to access Wi-Fi settings for a router on a local network, such as a home network. The user can access the Wi-Fi hub setup and choose a network from a list of available networks local to the user. The illustrated screenshot of FIG. 18A9 is an example screenshot displaying an indication that the medical monitoring hub device 1806 is connecting to the local network.

FIG. 18A10 is an example screenshot asking the user to allow the software application to access location information. When the software application has access to the user's location information such as the location information found on the user's mobile device 1818, the software application can provide the user's location to emergency personnel, caregivers, friends, and family, etc. when they are notified of an overdose event.

FIG. 18A11 is an example screenshot displaying an indication that the medical monitoring hub device 1806 is connecting to the cloud server 1812 via the local network. After the setup is complete, the medical monitoring hub device 1806 can communicate with the sensor and signal processing device 1802, the mobile device 1818 running the software application, and the could server 1812.

FIG. 18A12 is an example screenshot displaying a prompt to the user to add contact information for the respondents to be notified of an opioid overdose event that is occurring or will soon occur. the user can select, for example, from the list of contacts found in the mobile device 1818.

FIG. 18A13 is an example screenshot illustrating a selected respondent to be notified in the event of an opioid overdose event, where the opioid overdose event can be an overdose that is presently occurring or, based on the user's physiological parameters sensed by the sensor and signal processing device 1802, will soon occur. The selected respondent can also be notified of situations that may cause the opioid monitoring system to fail if not corrected, such as when the user is not wearing the sensor or the sensor battery is low. The illustrated screenshot of FIG. 18A13 displays the selected respondent's name and phone number and provides a selection of alerts that the user can choose the respondent to receive. The example selections include a parameter alert, a sensor off alert, and a battery low alert. The parameter alert can be sent when the monitored physiological parameter falls outside a range of acceptable values. The sensor off alert can be sent when the user is not wearing the sensor and signal processing device 1802. The batter low alert can be sent when the battery voltage in the sensor and signal processing device 1802 fall below a threshold value.

FIG. 18A19 is an example screenshot illustrating a selection of parameter notifications to be sent to the selected respondent. In the illustrated screenshot of Figure A19, the user can select to send the respondent any combination of a red alarm, an orange alarm, and a yellow alarm. For example, for the oxygen saturation parameter, a red alarm can be sent when the user's oxygen saturation falls within the range of 0-88; an orange alarm can be sent when the user's oxygen saturation falls within the range of 89-90, and a yellow alarm can be sent when the user's oxygen saturation falls within the range of 91-95 to provide an indication of the severity of the overdose event to the respondent.

FIGS. 18A14-18A15 are example screenshots illustrating the real time monitoring of the user's physiological parameters. The illustrated screenshots of FIGS. 18A14-18A15 display representation of dials indicating the monitored oxygen saturation, heart rate in beats per minute, and perfusion index. The illustrated screenshot of FIG. 18A14 indicates that the monitored oxygen saturation (96), heart rate 102), and perfusion index (8.5) are acceptable values. The illustrated screenshot of FIG. 18A15 indicates that the monitored oxygen saturation (86) is no longer within an acceptable range.

FIG. 18A16 is an example screenshot displaying a warning message to the user that the sensor is disconnected.

FIG. 18A17 is an example screenshot illustrating historical averages of the user's monitored physiological parameters. The illustrated screenshot of FIG. 18A17 displays the average oxygen saturation, heart rate, and perfusion index for the period of time the sensor and signal processing device 1802 collected data for two dates, March 11, and March 12.

FIG. 18A18 is an example screenshot illustrating session data for oxygen saturation, heart rate, and perfusion index on March 7. The displayed information in the illustrated example includes the minimum, maximum and average of the monitored physiological parameter.

FIG. 18A20 is an example screenshot illustrating sound options available for the software application. In the illustrated screenshot of FIG. 18A20, the software application can cause the mobile device 1818 to play a sound, such as a beep, that coincides with the user's pulse, play a sound, such as a beep, when a measurement value breaches its threshold range, and play a beep sound even when the software application is running in the background.

FIG. 18A21 is an example screenshot illustrating customizable alarm values. Some users may have a higher tolerance for opioids and an opioid event may not be occurring when the user's physiological parameters fall within a range that typically signals an opioid overdose event. It is desirable to avoid false alarms that may desensitize respondents to notifications. In the illustrated screenshot of FIG. 18A21, the ranges for a red, orange, and yellow alarms for oxygen saturation can be customized for the user by, for example, sliding the indicators along the green-yellow-orange-red bar until the desired values are displayed. Selecting beats/minute and pleth variability permits the user to customize the alarm ranges for heart rate and perfusion index, respectively.

FIG. 18A22 is an example screenshot illustrating that the user's physiological parameter data can be shared with other health monitoring applications, such as Apple Health.

FIG. 18A23 is an example screenshot illustrating a reminder to put on the sensor and signal processing device 1802 before going to bed. The software application may provide other reminders, such as time to replace the sensor battery, turn on notifications, and the like.

FIGS. 18A24-18A25 are example screenshots illustrating a request for user input when the user's physiological parameters indicate an opioid overdose event is occurring or will soon occur. To avoid sending false alarms, the software application requests user input to confirm that the user is not unconscious or otherwise does not want alarm notifications to be send to respondents. In the illustrated screenshot of FIG. 18A24, the user is asked to swipe the screen to confirm safety. In the illustrated screenshot of FIG. 18A25, the user is asked to enter an illustrated pattern on the screen to confirm safety. Different user inputs can be used to confirm different cognitive abilities of the user. For example, it is more difficult to enter the illustrated pattern of FIG. 18A25 than to swipe the bottom of the screen in FIG. 18A24.

Opioid Monitoring Kits

Figure 20A:
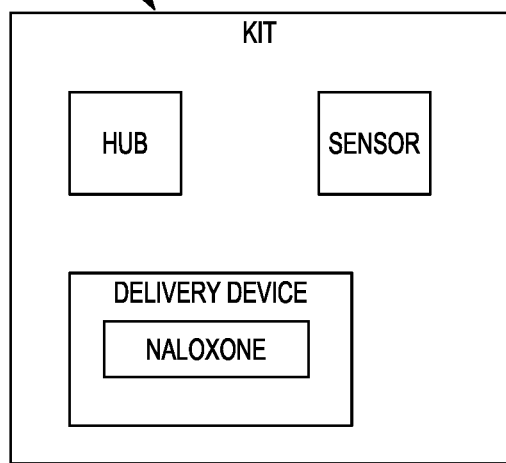
FIGS. 20A and 20B are schematic diagrams of example prescription and non-prescription opioid overdose monitoring kits.
Figure 20B:
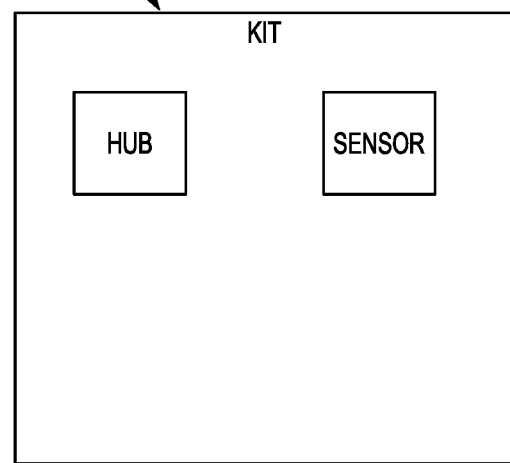

FIGS. 20A and 20B are schematic diagrams of example prescription and non-prescription opioid overdose monitoring kits 2000 and 2050. FIG. 20A is an example of the opioid overdose monitoring kit 2000 that may be available by prescription only, per the applicable state or country law. Kit 2000 can comprise a hub device 1806, a sensor 102, 610-640, 1802, and a delivery device 940, 950, 1100, 1200, 1702 that includes one or more doses of an opioid receptor antagonist receptor, such as Naloxone. FIG. 20B is an example of the opioid overdose monitoring kit 2050 that may be available without a prescription. Kit 2050 can comprise the hub device 1806 and a sensor 102, 610-640, 1802. Kits 2000, 2050 may include additional components to assist in opioid overdose monitoring.

Other Delivery Methods/Mechanisms

As discussed herein, opioid receptor antagonists can be delivered by intravenous injection, intramuscular injection, and intranasal application, where a liquid form of the medication is sprayed into the user's nostrils. Administration of the medication can also occur via an endotracheal tube, sublingually, where a gel or tablet of the medication is applied under the tongue, and transdermally, where the medication can be a gel applied directly to the skin or within a transdermal patch applied to the skin.

Other methods of administrating the opioid receptor antagonist can be via rectal capsule or suppository. The capsule can also monitor respiration rate and/or pulse rate and rupture the capsule when an opioid overdose event is imminent or occurring. A Bluetooth® signal can activate the capsule.

The opioid receptor antagonist can be included in an inhaler, by first injecting the user with an antiseptic and then with the opioid receptor antagonist, or in administered in an ear or other body orifice. The opioid receptor antagonist can be delivered through a cannula for a ventilator or breathing machine, for example.

The opioid receptor antagonist can be stored in a dental retainer that is crushed to release the stored drug.

An implantable delivery device can deliver the opioid receptor antagonist for chronic opioid users. The device can be implanted in a similar location as a pacemaker. The device can monitor one or more of respiration rate, pulse rate, ECG and SPO2 and release a dose of opioid receptor antagonist when an opioid overdose event is detected. The implantable device can comprise multiple doses and/or can be refillable by injecting the opioid receptor antagonist into the implantable delivery device. Such as delivery device can be implanted for one or more months. Another example of an implantable delivery device comprises a capsule containing the opioid receptor antagonist and an external device, such as a strap over the capsule that transmits a resonant frequency. The resonant frequency causes the capsule to rupture and the released opioid receptor antagonist is absorbed by the body.

The opioid receptor antagonist is contained in a pill that is activated when needed. The opioid receptor antagonist can be encased in a gel pack that is ingested or worn on the skin. An ultrasonic device, worn as a wrist strap, for example, can rupture the gel pack, adhered to the skin, for example, when an opioid overdose event is detected. The body can absorb the opioid receptor antagonist from the ruptured gel pack.

TERMINOLOGY

The embodiments disclosed herein are presented by way of examples only and not to limit the scope of the claims that follow. One of ordinary skill in the art will appreciate from the disclosure herein that many variations and modifications can be realized without departing from the scope of the present disclosure.

The term "and/or" herein has its broadest least limiting meaning which is the disclosure includes A alone, B alone, both A and B together, or A or B alternatively, but does not require both A and B or require one of A or one of B. As used herein, the phrase "at least one of "A, B, "and" C should be construed to mean a logical A or B or C, using a non-exclusive logical or.

The description herein is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to claims.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed is:

1. A system to monitor for indications of opioid overdose event, the system comprising:
    a memory of a medical monitoring hub storing software instructions, the software instructions executable by one or more hardware processors of the medical monitoring hub to cause the one or more hardware processors of the medical monitoring hub to:
        continuously receive data indicative of one or more physiological parameters of a first user that is being monitored by one or more sensors;
        continuously compare each of the one or more physiological parameters with a corresponding threshold;
        continuously receive input from devices local to the first user, the local devices capable of monitoring an environment local to the first user, the input from the local devices indicative of motion or sound in the local environment;
        determine an opioid overdose event is occurring or will soon occur based on at least one of the comparisons and the input from the local devices;
        transmit an alarm message to a first mobile communication device to cause an alarm on the first mobile computing device based on the determination; and
        transmit a notify message to a server storing contact information of a second user to notify the second user of the alarm by causing a display of a second mobile computing device associated with the second user to display a status of an alarming physiological parameter of the first user; and
    a memory of a first mobile computing device storing software instructions, the software instructions executable by one or more hardware processors of the first mobile computing device to cause the one or more hardware processors of the first mobile computing device to:
        trigger the alarm on the first mobile computing device in response to receiving the alarm message from the medical monitoring hub.
2. The system of claim 1 wherein the one or more hardware processors of the medical monitoring hub further cause a display of the first mobile computing device to continuously update graphical representations of the one or more physiological parameters in response to the continuously received data.
3. The system of claim 1 wherein the one or more hardware processors of the medical monitoring hub further cause a display of a user-selectable input to view additional information associated with the first user.
4. The system of claim 3 wherein selecting the user-selectable input causes the display of the second mobile computing device to display one or more of trends and current value of the alarming physiological parameter.
5. The system of claim 3 wherein selecting the user-selectable input causes the display of the second mobile computing device to display a location of the first mobile computing device on a map.
6. The system of claim 3 wherein selecting the user-selectable input causes the display of the second mobile computing device to display a time of an initial alarm.
7. The system of claim 3 wherein selecting the user-selectable input causes the display of the second mobile computing device to provide access to directions to the first mobile computing device from a location of the second mobile computing device.
8. The system of claim 3 wherein selecting the user-selectable input causes the display of the second mobile computing device to provide access to call the first mobile computing device.
9. The system of claim 1 wherein the one or more physiological parameters are represented as dials on the display of the first mobile computing device.
10. The system of claim 1 wherein the one or more physiological parameters include one or more of oxygen saturation, heart rate, respiration rate, pleth variability, perfusion index, and respiratory effort index.
11. A method to monitor for indications of an opioid overdose event, the method comprising:
    continuously receiving, with a medical monitoring hub, data indicative of one or more physiological parameters of a first user that is being actively monitored by one or more sensors;
    continuously comparing, with the medical monitoring hub, each of the one or more physiological parameters with a corresponding threshold;
    continuously receiving, with the medical monitoring hub, input from devices local to the first user, the local devices capable of monitoring an environment local to the first user, the input from the local devices indicative of motion or sound in the local environment;
    determining, with the medical monitoring hub, an opioid overdose event is occurring or will soon occur based on at least one of the comparisons and the input from the local devices;
    transmitting, with the medical monitoring hub, an alarm message to a first mobile computing device, to cause an alarm on the first mobile computing device based on the determination; and
    transmitting, with the medical monitoring hub, a notify message to a server storing contact information of a second user to notify the second user of the alarm by causing a display of a second mobile computing device associated with the second user to display a status of an alarming physiological parameters of the first user; and
    triggering, with the first mobile computing device, the alarm on the first mobile computing device in response to receiving the alarm message from the medical monitoring hub.

12. The method of claim 11 further comprising causing a display of the first mobile computing device to continuously update graphical representations of the one or more physiological parameters in response to the continuously received data.

13. The method of claim 11 further comprising displaying a user-selectable input to view additional information associated with the first user.

14. The method of claim 11 wherein the alarm is an audible and visual alarm.

15. The method of claim 11 wherein each of the corresponding thresholds is adjustable based on characteristics of the first user to inhibit false-positive alarms.

16. The method of claim 11 further comprising transmitting indications of the one or more physiological parameters to a remote server.

17. The method of claim 11 further comprising transmitting indications of the one or more physiological parameters to a medical monitoring hub for storage in memory of the medical monitoring hub.

18. The method of claim 11 further comprising communicating wirelessly with a local Internet of Things connected device to receive additional data for use in the determination of the opioid overdose event.

19. The method of claim 11 further comprising notifying emergency services of the alarm.

20. The method of claim 11 wherein the first and second mobile computing devices are smart phones.

* * * * *